United States Patent

Bech-Hansen et al.

(10) Patent No.: US 6,670,465 B1
(45) Date of Patent: Dec. 30, 2003

(54) RETINAL CALCIUM CHANNEL (ALPHA)$_{1F}$-SUBUNIT GENE

(76) Inventors: Torben Bech-Hansen, 526 - 37 Street NW., Calgary, AB (CA), T2N 3B8; Margaret Jane Naylor, 2905 - 6th Avenue NW., Calgary, AB (CA), T2N0Y5

( * ) Notice: Subject to any disclaimer, the term of this patent is extended or adjusted under 35 U.S.C. 154(b) by 0 days.

(21) Appl. No.: 09/495,714

(22) Filed: Feb. 1, 2000

Related U.S. Application Data

(63) Continuation of application No. PCT/CA99/00514, filed on Jun. 2, 1999.
(60) Provisional application No. 60/087,635, filed on Jun. 2, 1998.

(51) Int. Cl.$^7$ .......................... C07K 1/00; C07H 21/04; C12N 1/20; C12P 21/06; G01N 33/566
(52) U.S. Cl. .......................... 536/23.5; 435/6; 435/7.2; 435/7.21; 435/69.1; 435/252.3; 435/320.1; 435/325; 436/501; 530/350; 514/2
(58) Field of Search .......................... 536/23.5, 24.31, 536/501; 435/252.3, 6, 320.1, 69.1, 325, 7.2, 7.21; 530/350; 514/2

(56) References Cited

U.S. PATENT DOCUMENTS

| | | |
|---|---|---|
| 5,407,820 A | 4/1995 | Ellis et al. |
| 5,618,720 A | 4/1997 | Ellis et al. |
| 5,643,750 A | 7/1997 | Spreyer et al. |
| 5,686,241 A | 11/1997 | Ellis et al. |
| 5,710,250 A | 1/1998 | Ellis et al. |
| 5,846,757 A | 12/1998 | Harpold et al. |
| 5,851,824 A | 12/1998 | Harpold et al. |
| 5,874,236 A | 2/1999 | Harpold et al. |

FOREIGN PATENT DOCUMENTS

| | | |
|---|---|---|
| CA | 02074719 | 2/1991 |
| CA | 02113203 | 8/1992 |
| CA | 02166982 | 8/1994 |
| WO | WO9504144 | 2/1995 |

OTHER PUBLICATIONS

Nakamura et al., Invest. Ophthal. Vis. Sci. 42:7(1610–1630)2001.*
Bowie et al., Science 247:1306–1310.*
Ngo et al., The Protein Folding Problem and Tertiary Structure, pp 492–495, 1994.*
Heon and Musarella., "Congenital stationary night blindness: a critical Review for molecular approaches", in Molecular Genetics of Inherited Eye Disorders (eds. Wright, A.F. & Jay, B..) pp 277–301 (Harwood Academic Publishers, London, 1994).
Miyake, et al., "Congenital stationary night blindness with negative electroretinogram", Arch. Ophthalmol. 104, 1013–1020 (1986).
Weleber, et al., "Aaland Island Eye Disease (Forsius–Eriksson syndrome) associated with Contiguous deletion syndrome at Xp21", Arch. Ophthalmol 107:1170–1179.

(List continued on next page.)

*Primary Examiner*—Elizabeth Kemmerer
*Assistant Examiner*—Michael Brannock
(74) *Attorney, Agent, or Firm*—Bennett Jones LLP

(57) ABSTRACT

This present invention relates to calcium channel compositions. In particular, this invention relates to a mammalian gene, herein referred to as CACNA1F, encoding an (alpha)$_1$F-subunit of a retinal calcium channel. Mutations of CACNA1F may cause a type of X-linked congenital stationary night blindness known as incomplete CSNB, and may also cause Aaland Island Eye Disease, which may be clinically indistinguishable from incomplete CSNB.

7 Claims, 32 Drawing Sheets

Seventeen *CACNA1F* Mutations Identified in 31 Families Diagnosed with Incomplete CSNB and Four familes with Åland Island Eye Disease[a]

| Exon/Mutation[b] | Family | Nucleotide Change | Consequence[c] |
|---|---|---|---|
| 2  R50X | 590[e], 710 | C to T | LOF, NS – Arg to Stop |
| 2  R82X | 670 | C to T | LOF, NS – Arg to Stop |
| 4  S156(del4nt/ins34bp) | M10, HM | net 30 bp insert | MS, Del/Ins - additional 10 aa |
| 7  delF316[d] | 600 | CTT deleted | MS, Del - Phe |
| 8  G369A | 720 | G to A | MS, Gly to Asp |
| 9  D406delC | 70 | C deleted | LOF, frameshift, Stop in E11 |
| 19  E797V | 533[e] | A to T | MS, Glu to Val |
| 21  R895X | 513, 520 | C to T | LOF, NS - Arg to Stop |
| 23  A928N | 230 | C to A | MS, MS - Ala to Asp |
| 27  Exon27AS | 530[e] | G to A | LOF, SS mutation, skip exon |
| 27  G1042de G | 8003 | G inserted | LOF, frameshift, Stop |
| 27  L1056insC | Mennonite (15) | C inserted | LOF, frameshift Leu to Stop in E27 |
| 30  I1224delC | 21 | C deleted | LOF, Del, Ile to Stop in E31 |
| 33  R1296S | 820 | | MS, Arg to Ser |
| 33  R1299X | 100, 531[e] | C to T | LOF, NS - Arg to Stop |
| 37  W1451X | 140 | G to A | LOF, NS - Trp to Stop |
| 41  Exon41AS | 510 | A to G | LOF, SS mutation – skip E41, Stop within E42 |

OTHER PUBLICATIONS

Boycott, et al., "Evidence for genetic heterogeneity in X–linked congenital stationary nigh Blindness", Am. J. Hum. Genet. 62:865–875 (1998).

Catterall, "Structure and function of voltage–gated ion channels". Annu. Rev. Biochem. 64,493–531(1995).

Fisherman and Sokol, "Electrophysiologic Testing in Disorders of the Retina. Optic Nerve, and Visual Pathway", (Am. Acad. Ophthal., San Francisco, 1990).

Wilkinson and Barnes, "The dihydropyridine–sensitive calcium channel subtype in Cone photoreceptors", J. en. Physiol. 107, 621–630 (1996).

Boycott, et al., "A 2–megabase physical contig incorporating 43 DNA markers on the Human X chromosome at p11.23–p11.22 from ZNF21 to DXS255", Genomics 33, 488–497 (1996).

Schindelhauer, et al., "Long–range mapping of a 3.5–MB region in Xp11.23–22 with a Sequence–ready map from a 1.1Mb gene–rich interval", Genome Res 6, 1056–1069 (1996).

Boycott, et al., "Construction of a 1.5 Mb bacterial artificial chromosome (BAC) contig In Xp11.23, a region of high gene content" Genomics, 48:369–372 (1998).

Fisher, et al., "Sequence–based exon prediction around the synaptophysin locus reveals A gene–rich area containing novel genes in human proximal Xp", Genomics 45,340–347 (1997).

Williams, et al., "Structure and functional expression of $\alpha 1$, $\alpha 2$, and $\beta$ subunits of a novel Human neuronal calcium subtype", Neuron 8, 71–84 (1992).

Schuster, et al., "The IVS6 segment of the L–type calcium channel is critical for the action Of dihydrophyridines and phenylalkylamines", EMBO J. 15, 2365–2370 (1996).

Boycott, et al., "Integration of 101 DNA markers across human Xp11 using a panel of Somatic cell hybrids", Cell Cytogenet. Enet. 76, 223–228 (1997).

Nathans and Hogness, "Isolation, sequence analysis, and intron–exon arrangement Of the gene encoding bovine rhodopsin", Cell 34, 807–814 (1983).

Bech–Hansen, et al., "Loss–of–function mutations in a calcium–channel $\alpha_1$–subunit gene in Xp11.23 cause incomplete X–linked congenial stationary night blindness". Nature Genet. 19: 264–267 (1998).

* cited by examiner

Figure 2

Human CACNAIF Primer Sets

| Primer Set | Forward Primer Name | Forward Sequence | Reverse Primer Name | Reverse Sequence | Size (bp) |
|---|---|---|---|---|---|
| Exons 1-6 | JM8-Ex1Fcod | gagaatccttccatccctgc SEQ ID NO: 29 | JM8-Ex6Rcod | attcgtccaaggaacagctc SEQ ID NO: 30 | 564 |
| Exons 3-6 | JMC8Ex3Fcod | gtggagacggtgctcaagat SEQ ID NO: 31 | JM8-Ex6Rcod | attcgtccaaggaacagctc SEQ ID NO: 32 | 371 |
| Exons 6-10 | JM8-Ex6Fcod | tcgtgctcftcgtcatcatc SEQ ID NO: 33 | JM8-Ex10Rcod | tggagtgtggagcgagta SEQ ID NO: 34 | 663 |
| Exons 10-15 | JM8-Ex10F cod | accaataggaggcgtggac SEQ ID NO: 35 | JM8-Ex15Rcod | ggtgtgggtctggtcaaagt SEQ ID NO: 36 | 738 |
| Exons 15-20 | JM8-Ex15Fcod | ttctcctcttcctcftcatcaft SEQ ID NO: 37 | JM8-Ex20rcod | ggtttggctgaggcagaag SEQ ID NO: 38 | 590 |
| Exons 20-27 | JM8-Ex20fcod | tgtaccaaggagaaggtgg SEQ ID NO: 39 | JM8-Ex27(28)Rcod | aagtgatgatgacgaagccc SEQ ID NO: 40 | 911 |
| Exons 24-32 | JM8-Ex24Fcod | ccatctcggtggtgaagatt SEQ ID NO: 41 | JM8-Ex32(33)Rcod | cggatcccttcaccftact SEQ ID NO: 42 | 1060 |
| Exons 27-36 | JM8-Ex27(28)Fcod | taccgtgtggagatctcagtgt SEQ ID NO: 43 | JM8-Ex36(38)Rcod | caacCacatccaagtgtttgat SEQ ID NO: 44 | 1126 |
| Exons 32-36 | JM8-Ex32(33)Fcod | gcatttccattaccttctttcg SEQ ID NO: 45 | JM8-Ex36(38)Rcod | caaccacatccaagtgtttgat SEQ ID NO: 46 | 765 |
| Exons 35-38 | JM8-Ex35(37)Hfcod | caccagagaftggtccatcc SEQ ID NO: 47 | JM8-Ex38(40)Rcod | ggggatgacctcatctagca SEQ ID NO: 48 | 373 |
| Exons 40-46 | JM8-Ex40(42)Fcod | tgaaaaggacftgaaactaacaa SEQ ID NO: 49 | JM8-Ex46(48)Rcod | gccatctcgtcccaagt SEQ ID NO: 50 | 954 |

Figure 4a

```
         Exon 1
   1     ATGTCGGAATCTGAAGGCGGAAAGGTGAAGAGAATCTTCATCCCTGCAGACCCTTGGAGTGAGTGAAGCCTGTCAGCATCGTCGAGTGGAAGCCTTTCATCCTGCTGACCATCTTTGCCAAC
   1     M  S  E  S  E  G  G  K  G  E  R  I  L  P  S  L  Q  T  L  G  A  S  I  V  E  W  K  P  F  D  I  L  L  T  I  F  A  N
                                                                                                               IS1

|Exon 2       |Exon 3
 121     TGGGTGGCCCTGGAGTTTACATCCCCTTCCTGAGGACGACTGGAGCTCCAACACTGCCAACACTGCCAACCTGGAGCAGGTGGAGTACGTATTCCTGGTGATTTTCACTGTGGAGACGGTGCTCAAG
  41     C  V  A  L  G  V  Y  I  P  F  F  P  E  D  D  S  N  T  A  N  H  N  L  E  Q  V  E  Y  V  F  L  V  I  F  T  V  E  T  V  L  K
                                                                                                                                  IS2

|Exon 5
 241     ATCGTGGCCTACGGCCTCGTCCTCCACCCGAGCGCCTACATCCGCAATGGCTGGAACCTACTCGACTTCATCATCGTGGTGGGCCTGTTCAGCGTTCTGTGCTGGAGCAGGGCCCGA
  81     I  V  A  Y  G  L  V  L  H  P  S  A  Y  I  R  N  G  W  N  L  L  D  F  I  I  V  V  G  L  F  S  V  L  L  E  Q  G  P  G
                                                                                                                              |Exon 6
                                                                           IS3

361     CGGCCAGGCGACGGCCCCCACACCGGGGAAAGCCAGGAGGCTTCGATGTGAAGGCATTGAAGGGCTTTGATGTGAAGGCATTGAAGCTGTCCGCCTGCACATA
 121     R  P  G  D  A  P  H  T  G  G  K  P  G  G  F  D  V  K  A  L  R  A  F  R  V  L  R  P  L  R  L  V  S  G  V  P  S  L  H  I
                                                                                           IS4

481     GTGCTCAATTCCATCATGAAGGCTCTGGTGCCTCTGCTGCACATTGGGCTCTGTCATCATCATTGGGCTCTGAGCTGTTCCTTGACGAATGCAAAG
 161     V  L  N  S  I  M  K  A  L  V  P  L  L  H  I  A  L  L  V  L  F  V  I  I  Y  A  I  I  G  L  E  L  F  L  G  R  M  H  K
                                                                    IS5

|Exon 7
 601     ACGTGCTACTTCCTGGGATCCGACATGGAAGCGGAGGAGGAGGAGGAGGACCCATCGCCTGCGCTTCCGGGATCCAGGGCGCCGACCAGAGTGACGCCGGGCCGCCTGGCGCCGAGGCGCGCTGGCCAGGG
 201     T  C  Y  F  L  G  S  D  M  E  A  E  E  E  D  P  S  P  C  A  S  S  G  S  G  R  A  C  T  L  N  Q  T  E  C  R  G  R  W  P  G

|Exon 8
 721     CCCAATGAGGAGCATCACCAACTTTGACAACTTTTTCTTTGCCATGCTGACAGTCTTCCAGTGTGTCCATGGAGAGTGGACCGATGTCCTCTACTGGCAAGATGCCATGGGTTAT
 241     P  N  G  G  I  T  N  F  D  N  F  F  F  A  M  L  T  V  F  Q  C  V  T  M  E  G  W  T  D  V  L  Y  W  Q  D  A  M  G  Y

|Exon 9
 841     GAACTGCCCTGGGTACTTTGTAGCTTGCTCATCATCTTTGGTTCATTCGTCCTCAACCTTGTCCTGGGCGCCCTCAGCGGAGAGTTCTCCAAGGAGAGGAAGCGAAAGCTCGC
 281     E  L  P  W  V  Y  F  V  S  L  V  I  F  G  S  F  F  V  L  N  L  V  L  G  V  L  S  G  E  F  S  K  E  R  E  K  A  K  A  R 961     GGGACTTCCAGAACTCCAGGAGAACGCACCGGGGAGAATGAGGAAGCAGAAGAAGACCTGCGGGCTACCTGGATCACTCAAGCTGAAGAGGAGCTGGACATGGAGGACCCCTCCGCCGATGACAACCTT
 321     G  D  F  Q  K  Q  R  E  K  Q  Q  M  E  E  D  L  R  G  Y  L  D  W  I  T  Q  A  E  E  L  D  M  E  D  P  S  A  D  D  N  L

|Exon 10
1081     GGTTCTATGGCTGAAGAGGGCCGGGCGGCGGGCAGGCCCGGGCCATGCGGCACTGGCCAATAGAGCGCGCCGCGGGCGCCTCCGTGGTTCAGTCATTCTACTCGCTCCACACTCCACCAGC
 361     G  S  M  A  E  E  G  R  A  G  H  R  P  Q  L  A  E  L  T  N  R  R  R  G  R  L  R  W  F  P  S  H  S  T  R  S  T  S

|Exon 12
1201     AGCCATGCCAGCCTCCCAGCCGTTGACACCGGTGGCAGCATGACAGAGACCCAAGGCGATGAGGAGGAGGAAGGAGCTCTGGCCAGCTGTACACGCTGCTAACAGATCATGAAAACC
 401     S  H  A  S  L  P  A  S  D  T  G  S  M  T  E  T  Q  Q  G  D  E  D  E  E  E  G  A  L  A  S  C  T  R  C  L  N  K  I  M  K  T

|Exon 13
1321     AGAGTCTGCCGCCGTCGCCGCCTGCGCCGCGCCAACAGGGTTCTGCGGGCCCGCTGTCGCCGCGCGGTGGTGAAGTCCAATGCCTGCTACTGGGCTGTGTTGCTCTGTCTCTTCACCGTTGAGATGCTTCTCAAACGTTGACC
 441     R  V  C  R  R  L  R  R  A  N  R  V  L  R  A  R  C  R  R  A  V  K  S  N  A  C  Y  W  A  V  L  L  C  L  F  T  V  E  M  L  L  K  L  Y  T
                                                                                                                                                    IIS1

|Exon 14
1441     ATCGCCCTCTGAGCACCGAGCCTGTGTGCCTCACCCAGATCCAGGAGTATGCAAACAAAGTTGTCCTCTGTCTCTTCACCGTGGAGATGCTTCTCAAATTGTACGGTCTGGGCCCC
 481     I  A  S  E  H  H  G  Q  P  V  W  L  T  Q  I  Q  E  Y  A  N  K  V  L  L  C  L  F  T  V  E  M  L  L  K  L  Y  G  L  G  P
                                IIS2
```

```
5161  GTACCACGCCGCCGTCTGCCCCCACACCTGCAGGTCGGAGAAGCCCTCTTCACCATCCAGTGTCTGCAGGGCCAGGGCAGTTGTGAGGATTTACCATCCAGGCACTTATCATCGT
1721   V  P  R  R  R  L  L  P  P  T  P  A  G  R  K  P  S  F  T  I  Q  C  L  Q  R  Q  G  S  C  E  D  L  P  I  P  G  T  Y  H  R
                                                                |Exon 46

5281  GGGCGAAATTCAGGGCGCTCAGGGTTCCTGGGCCAACACACTGGCAACCTCAGCGCGGGTCGGCTCCTGTCTTGTTGGTGAAGAGGGCCCAGCGGCCGAGGGTACCTC
1761   G  R  N  S  G  P  N  R  A  Q  G  S  W  A  T  P  P  Q  R  G  R  L  L  Y  A  P  L  L  V  E  E  G  A  A  G  E  G  Y  L
                            |Exon 47

5401  GGCAGATCCAGTGGCCCTCTCGCACCTTCACCTGTCTCCACGTCCCAGCCATGGAAGAGGGGCAGTGCCGACAGCTTGGTGAGGCTGTGCTTATCTCA
1801   G  R  S  S  G  P  L  R  T  F  T  C  L  H  V  P  G  T  H  S  D  P  S  H  G  K  R  G  S  A  D  S  L  V  E  A  V  L  I  S
                                                                                                      |Exon 48

5521  GAGGGTCTGGGCCTCTTCGCTGCAGACCCACGTTCGTGGCCAAGCAGGAGATTGCAGATGCTTGCCGTGTGCCTGATGAGATGGACAATGCCAGTGACCTGCTGGCA
1841   E  G  L  F  A  R  D  P  P  R  F  V  A  L  A  K  Q  E  I  A  D  A  C  R  L  T  L  D  E  M  D  N  A  A  S  D  L  L  A

5641  CAGGGAACCAGTCTCTCTATAGCGACGAGGAGTCCATCCTCTCCCGGTTCGATGAGGAGGACTTGGGAGACGAGATGGCCTGCGTCCACGCCCTCTGAATTCCCACCCCTCCCAACTG
1881   Q  G  T  S  S  L  Y  S  D  E  E  S  I  L  S  R  F  D  E  E  D  L  G  D  E  M  A  C  V  H  A  L  *

5761  CTCAATAAACCTCTGCCCTCCCCCTCCCCAGCAGGAGGCAGGCATGACCACA
```

```
                                                                                              |Exon 47
5401  CCCTCCTTCACCATCCAGTGTCTGCAGGGCCAGGGCAGTTTACCCATTGTGAGGATTTACCCATCATCGTGGGCGAAATTCAGGGCCCAATAGGGCTCAGGGTTCCTGGGCAACA
1801   P  S  F  T  I  Q  C  L  Q  R  Q  G  S  C  E  D  L  P  I  P  G  T  Y  H  R  G  R  N  S  G  P  N  R  A  Q  G  S  W  A  T 5521  CCACCTCAGCGGGGTCGGCTTCCTGTATGCCCCGTGTTGTTGCTGTGGAAGAGGGTACCTCGGCAGATCCAGTGCCCAGTGCCACTTCACCTGTCTGCACGTG
1841   P  P  Q  R  G  R  L  L  Y  A  P  L  L  V  E  E  G  A  A  G  E  G  Y  L  G  R  S  S  G  P  L  R  T  F  T  C  L  H  V

|Exon 48
5641  CCTGGAACCCCACTCGGACCCCAGCCATGGGAAGAGGGCAGTGCCGACAGCTTGGTGGAGGCTGTGCTTATCTCAGAGGGTCTGGGCCTCTTTGCTCGAGACCCACGTTTCGTGGCCCTG
1881   P  G  T  H  S  D  P  S  H  G  K  R  G  S  A  D  S  L  V  E  A  V  L  I  S  E  G  L  G  L  F  A  R  D  P  R  F  V  A  L 5761  GCCAAGCAGGAGATTGCAGATGCGTGCCGTGTCGCCTGAGCTGGATGAGATGGACAATGCTGCCAGTGACCTGCTGGCACAGGGAACCAGCTCTCTCTATAGCGACGAGGAGTCCATCCTCTCC
1921   A  K  Q  E  I  A  D  A  C  R  L  T  L  D  E  M  D  N  A  A  S  D  L  L  A  Q  G  T  S  S  L  Y  S  D  E  E  S  I  L  S 5881  CGCTTCGATGAGGAGGACTTGGGAGACGGAGATGGAGATGCCTGCGTCCACGCCCTCTGAATTCCACCCCTCCCCAACTGCTCAATAAACCTCCTGCCTCCCCTGCCCAGCAGGAGGCAGGCAT
1961   R  F  D  E  E  D  L  G  D  G  D  E  M  A  C  V  H  A  L  *

6001  GGACCACAAAAAAAAAAAAAAAAAAAAAAAAAAAAAAAAA
```

Figure 6A

Exon-specific PCR Primers for CACNA1F

| Exon | Forward Primer, 5'-3' | Reverse Primer, 5'-3' | bp |
|---|---|---|---|
| 1 | CCACCCTCCCATACAACACT<br>SEQ ID NO: 51 | GTGATOTGGTTCTTGTCCCC<br>SEQ ID NO: 52 | 254 |
| 2 | GATCAGGTAGGAAGCAGCCA<br>SEQ ID NO: 53 | CTCCTGGTACCCTGATGACC<br>SEQ ID NO: 54 | 374 |
| 3 | GAGGTTCCCAAGGGAGTAGG<br>SEQ ID NO: 55 | GTCTGGCTGGAAGGAGTGAG<br>SEQ ID NO: 56 | 247 |
| 4 | CTCGGTCCTGACTATGCTCC<br>SEQ ID NO: 57 | GGTAGGAAGGCGACTAGGGT<br>SEQ ID NO: 58 | 276 |
| 5 | ATCCCAAGGCCTGACCTC<br>SEQ ID NO: 59 | ACCCTCCACCTCCGACCT<br>SEQ ID NO: 60 | 226 |
| 6 | CTGACCCCGCCCTTATTTCT<br>SEQ ID NO: 61 | AGCATTGGATCTAGGAACCG<br>SEQ ID NO: 62 | 258 |
| 7 | ACTGAGAGTGGGCCTGCTT<br>SEQ ID NO: 63 | GTGCAGCCTTGAGCTCTGT<br>SEQ ID NO: 64 | 283 |
| 8 | GGATGCATGCCTTTTCTCTC<br>SEQ ID NO: 65 | GTTTGCCAGGCACAAAGAAG<br>SEQ ID NO: 66 | 197 |
| 9 | TGTGGCTGGAGTGATGAAAG<br>SEQ ID NO: 67 | GGAGGGCAGACCACATCTAA<br>SEQ ID NO: 68 | 271 |
| 10 | AATTGTCCTTCTCTCCCTGC<br>SEQ ID NO: 69 | CAGCCTGGCTGGACCCCC<br>SEQ ID NO: 70 | 236 |
| 11 | AGGTCCTGACCACTATCCCC<br>SEQ ID NO: 71 | GGACTTGAGTCAGGGTTTGG<br>SEQ ID NO: 72 | 186 |
| 12 | TTTACGACACACCTCCCA<br>SEQ ID NO: 73 | CACCTACCTAAGCCTGCCCT<br>SEQ ID NO: 74 | 181 |
| 13 | AGGGCAGGCTTAGGTAGGTG<br>SEQ ID NO: 75 | AGAAGGAATAGGAGGCTGGG<br>SEQ ID NO: 76 | 259 |
| 14 | GATCATCCCTGCCTCTCTCC<br>SEQ ID NO: 77 | CTTCCCCCTCCCCTAATACA<br>SEQ ID NO: 78 | 275 |
| 15 | AGCCTAMGAGCCCAACCT<br>SEQ ID NO: 79 | ACCCATCCCATGGTCTCC<br>SEQ ID NO: 80 | 357 |
| 16 | GAGCTCCACAGTGACTTCCC<br>SEQ ID NO: 81 | ACCCTGCCTATAGACCACCC<br>SEQ ID NO: 82 | 228 |
| 17 | GTGGTCTATAGGCAGGGTGC<br>SEQ ID NO: 83 | GACTGTGTAGGGGTGGAGC<br>SEQ ID NO: 84 | 165 |
| 18 | ATGGGACCCAAGAAAGGTCT<br>SEQ ID NO: 85 | GTGGGAOTGGGAGGTGTAGA<br>SEQ ID NO: 86 | 171 |
| 19 | CCTCACCATGATGACTCCC<br>SEQ ID NO: 87 | TGTCTGCCGAGCTCMCC<br>SEQ ID NO: 88 | 149 |
| 20 | CAAACACTGTTCTGGGTGCT<br>SEQ ID NO: 89 | CTCCTCCATGCTCCTCCAC<br>SEQ ID NO: 90 | 292 |
| 21 | TCAGGGCCAGAACTGTATCC<br>SEQ ID NO: 91 | GTCCCCTCAGCTCCTAGCTC<br>SEQ ID NO: 92 | 249 |
| 22 | CTCCCCGCTCTTTCACAC<br>SEQ ID NO: 93 | GACTGGGGTCCCAITAGTCA<br>SEQ ID NO: 94 | 106 |
| 23/24 | TCCCCAGGTCTGAGTCTAGC<br>SEQ ID NO: 95 | GTCCTGTGGGTTTGGGTG<br>SEQ ID NO: 96 | 349 |
| 25/26 | GTAGCCATATGCTTGGGTGC<br>SEQ ID NO: 97 | AGTCTTGGGAGGGGTCCT<br>SEQ ID NO: 98 | 330 |

Figure 6B

| Exon | Forward Primer, 5'-3' | Reverse Primer, 5'-3' | bp |
|---|---|---|---|
| 27 | AGTTCCTCACCCCTCCTCAC<br>SEQ ID NO: 99 | CTGCCTCATCCCCTGATAAA<br>SEQ ID NO: 100 | 234 |
| 28/29 | ATTTAGGGGTCTTGGGGTG<br>SEQ ID NO: 101 | GCAGCCTTAAATGTTCCCAA<br>SEQ ID NO: 102 | 679 |
| 30 | CAGTGCAAGAGGTTGACCA<br>SEQ ID NO: 103 | CCCAAGGAATTCATCCACTG<br>SEQ ID NO: 104 | 293 |
| 31 | GCTTT GAGAAGACAGGGCAC<br>SEQ ID NO: 105 | GAAAGCCAGTAGAGGGGGAC<br>SEQ ID NO: 106 | 318 |
| 32 | GTAATGACCCCACCATCACC<br>SEQ ID NO: 107 | CAGAGGGACATGGGAAAAGA<br>SEQ ID NO: 108 | 189 |
| 33 | AAATGCAAACTGAGCATCCC<br>SEQ ID NO: 109 | AMGGAAATGGGTATGGCA<br>SEQ ID NO: 110 | 284 |
| 34 | GACTGCATCTCCCAGTAGGC<br>SEQ ID NO: 111 | ATTCTTAACCCATCCCCTGC<br>SEQ ID NO: 112 | 242 |
| 35 | GTAGGGGTGGCAGGTAGACA<br>SEQ ID NO: 113 | GTGGCAGGGGAGTGAGTAGA<br>SEQ ID NO: 114 | 297 |
| 36 | GATGTAGCCCCTGGTGAGAA<br>SEQ ID NO: 115 | GGTGGTGTGAGGAAATGGT<br>SEQ ID NO: 116 | 304 |
| 37 | ACAGTGTTCTGCCCTTCACC<br>SEQ ID NO: 117 | AACTGGAGGGCAGTCAGAGA<br>SEQ ID NO: 118 | 339 |
| 38 | CAGTGGTACCTCCCCAACTC<br>SEQ ID NO: 119 | AGAAACCTCTGAGGATGCGA<br>SEQ ID NO: 120 | 239 |
| 39 | ACATTCGTTCCTGCATACCC<br>SEQ ID NO: 121 | ATGAGMGCTCCTTGCACC<br>SEQ ID NO: 122 | 224 |
| 40/41 | TCTTCCTATTGGCTCATGCC<br>SEQ ID NO: 123 | GGGGCCTCAGMCCTTATC<br>SEQ ID NO: 124 | 568 |
| 42 | ACCTATTTCTCCACCCCCAC<br>SEQ ID NO: 125 | GCTTCTTCCCAGAAGCAGTG<br>SEQ ID NO: 126 | 245 |
| 43 | GTGCATGCAACACTCAGTCC<br>SEQ ID NO: 127 | CTCAACTTCCTGCCTCCTGA<br>SEQ ID NO: 128 | 291 |
| 44 | ATCTGGTCTGCCTAACGTGC<br>SEQ ID NO: 129 | GAGATGGGGCACAAACAGTC<br>SEQ ID NO: 130 | 234 |
| 45 | GACTGTTTGTGCCCCATCTC<br>SEQ ID NO: 131 | TTCCCCAGATCTCTGTCCTG<br>SEQ ID NO: 132 | 265 |
| 46 | CTGACATTGCTATTTGCCCC<br>SEQ ID NO: 133 | AAAGGGCCTGATATGTGCTG<br>SEQ ID NO: 134 | 248 |
| 47 | AGCGGTGAGTCCTAGACCCT<br>SEQ ID NO: 135 | GACTCCTTTCCGTCCTCCTC<br>SEQ ID NO: 136 | 347 |
| 48 | CGTCAACACTGATCCCACCT<br>SEQ ID NO: 137 | CAAAATCCAGGGATGTGGTC<br>SEQ ID NO: 138 | 348 |

Seventeen *CACNA1F* Mutations Identified in 31 Families Diagnosed with Incomplete CSNB and Four familes with Åland Island Eye Disease[a]

| Exon | Mutation[b] | Family | Nucleotide Change | Consequence[c] |
|---|---|---|---|---|
| 2 | R50X | 590[e], 710 | C to T | LOF, NS – Arg to Stop |
| 2 | R82X | 670 | C to T | LOF, NS – Arg to Stop |
| 4 | S156(del4nt/ins34bp) | M10, HM | net 30 bp insert | MS, Del/Ins – additional 10 aa |
| 7 | delF316[d] | 600 | CTT deleted | MS, Del – Phe |
| 8 | G369A | 720 | G to A | MS, Gly to Asp |
| 9 | D406delC | 70 | C deleted | LOF, frameshift, Stop in E11 |
| 19 | E797V | 533[e] | A to T | MS, Glu to Val |
| 21 | R895X | 513, 520 | C to T | LOF, NS – Arg to Stop |
| 23 | A928N | 230 | C to A | MS, MS – Ala to Asp |
| 27 | Exon27AS | 530[e] | G to A | LOF, SS mutation, skip exon |
| 27 | G1042de G | 8003 | G inserted | LOF, frameshift, Stop |
| 27 | L1056insC | Mennonite (15) | C inserted | LOF, frameshift Leu to Stop in E27 |
| 30 | I1224delC | 21 | C deleted | LOF, Del, Ile to Stop in E31 |
| 33 | R1296S | 820 | | MS, Arg to Ser |
| 33 | R1299X | 100, 531[e] | C to T | LOF, NS – Arg to Stop |
| 37 | W1451X | 140 | G to A | LOF, NS – Trp to Stop |
| 41 | Exon41AS | 510 | A to G | LOF, SS mutation – skip E41, Stop within E42 |

Figure 8

Figure 9a aagatgggag.gactgtgtgc.atgatggtcc.ttatatctcc tgaggaggAT
GTCGGAATCT GAAGTCGGGA AAGATACAAC CCCAGAGCCC AGTCCAGCCA
ATGGGACTGG CCCTGGCCCT.GAATGGGGC TCTGTCCTGG GCCTCCAACT
GTGGGGACTG ATACCAGCGG GGCGTCAGGC CTGGGACCC CAAGAAGAAG
GACCCAGCAC AACAAACACA AGACTGTGGC GGTGGCCAGT GCTCAGAGAT
CACCTCGAGC GCTCTTCTGC CTCACCCTTA CTAATCCCAT TCGTCGGTCC
TGCATCAGCA TTGTAGAGTG GAAGCCTTTT GATATTCTCA TCCTCCTGAC
AATCTTTGCC AACTGCGTGG CATTGGGGT ATATATCCCC TTCCCTGAGG
ACGACTCCAA CACTGCTAAC CACAACTTGG AACAGGTAGA ATACGTGTTC
CTGGTGATTT TCACCGTGGA GACAGTGCTC AAGATCGTAG CCTATGGGCT
GGTGCTCCAT CCCAGCGCCT ATATTCGCAA TGGCTGGAAC CTGCTCGACT
TCATCATCGT CGTGGTCGGG CTGTTCAGCG TGCTGCTGGA ACAAGGACCT
GGGCGGCCAG GAGATGCCCC GCATACTGGA GGAAAGCCAG GAGGCTTCGA
TGTAAAGGCA CTGCGGGCAT TTAGGGTGCT ACGACCTCTA AGGCTAGTGT
CTGGGGTCCC GAGTCTGCAC ATAGTCGTCA ATTCCATCAT GAAGGCGCTT
GTGCCGCTGC TGCACATTGC CCTGTTGGTG CTCTTCGTCA TTATCATTTA
CGCCATCATC GGACTCGAGC TATTCCTCGG ACGAATGCAC AAGACATGCT
ACTTCCTGGG ATCTGATATG GAAGCAGAGG AGGACCCATC ACCTTGTGCA
TCTTCTGGCT CTGGGCGTTC ATGCACACTG AACCATACCG AGTGCCGCGG
GCGCTGGCCA GGACCCAACG GTGGCATCAC GAACTTCGAC AATTTTTTCT
TTGCCATGCT AACTGTGTTC CAGTGTATTA CCATGGAAGG CTGGACAGAC
GTCCTCTACT GGATGCAGGA TGCCATGGGG TATGAGCTGC CTTGGGTGTA
CTTTGTGAGC CTTGTCATCT TTGGGTCCTT CTTTGTCCTC AACCTTGTGC

Figure 9b

```
TTGGAGTCCT AAGCGGGAG TTCTCCAAGG AAAGAGAAAA GGCAAAAGCA

CGAGGTGACT TTCAGAAGCT TCGGGAGAAG CAGCAGATGG AAGAAGACCT

TCGGGGCTAC CTGGACTGGA TCACACAGGC TGAGGAGTTA GACCTTCATG

ACCCCTCAGT AGACGGCAAC TTGGCTTCTC TTGCTGAAGA GGGACGGGCG

GGCCATCGGC CACAACTGTC AGAGCTGACC AATAGGAGGC GCGGACGGCT

GCGATGGTTC AGCCACTCTA CTCGCTCCAC ACACTCCACC AGCAGCCACG

CCAGCCTCCC AGCCAGTGAC ACTGGCTCCA TGACAGACAC CCTGGAGAT

GAGGATGAAG AAGAGGGGAC CATGGCTAGC TGTACACGCT GCCTAAACAA

GATTATGAAA ACAAGGATCT GCCGCCACTT CCGCCGAGCC AACCGGGGTC

TCCGTGCACG CTGCCGCCGG GCCGTCAAGT CCAACGCCTG CTACTGGGCT

GTACTGTTGC TCGTCTTCCT CAACACGTTG ACCATCGCTT CAGAGCACCA

TGGGCAGCCT TTGTGGCTCA CCCAGACCCA AGAGTATGCC AACAAAGTTC

TGCTCTGCCT CTTCACTGTG GAGATGCTCC TCAAACTGTA CGGCCTGGGC

CCCTCTGTCT ACGTTGCCTC CTTTTTCAAC CGCTTTGACT GCTTCGTGGT

CTGTGGGGGC ATCCTAGAAA CCACTTTGGT GGAGGTGGGG GCCATGCAGC

CTCTTGGCAT CTCAGTGCTC CGATGTGTAC GTCTCCTCAG GATCTTCAAG

GTCACCAGGC ACTGGGCATC CCTGAGCAAT CTGGTGGCAT CTTTGCTCAA

TTCCATGAAG TCCATCGCCT CCTTGCTGCT TCTCCTCTTT CTCTTCATCA

TCATCTTCTC CCTGCTTGGC ATGCAGCTGT TTGGGGGCAA GTTCAACTTT

GACCAGACCC ACACCAAGAG GAGCACCTTT GATACCTTCC CCCAAGCCCT

CCTCACTGTC TTTCAGATCC TGACTGGTGA GGATTGGAAC GTTGTCATGT

ATGATGGTAT CATGGCCTAC GGTGGGCCCT TCTTCCCAGG GATGCTGGTG

TGTGTTTATT TCATCATCCT CTTCATCTGT GGCAACTACA TCCTGCTGAA

CGTGTTTCTT GCCATTGCCG TGGATAACCT AGCCAGCGGG GATGCAGGCA
```

Figure 9c

```
CTGCCAAAGA TAAGGGCAGA GAGAAGAGCA GTGAAGGAAA CCCTCCAAAG
GAGAACAAAG TATTGGTGCC TGGTGGAGAG AATGAGGACG CAAAGGGCGC
AAGAAGTGAA GGAGCAGCAC CAGGCATGGA GGAGGAGGAG GAGGAGGAGG
AGGAAGAAGA AGAGGAGGAG GAGGAGGAAG AGGAAAATGG TGCAGGACAT
GTGGAACTCT TGCAGGAAGT AGTACCCAAG GAGAAGGTGG TACCCATCCC
TGAAGGCAGT GCCTTCTTCT GCCTTAGCCA AACCAACCCG CTTCGGAAGG
CCTGCCACAC ACTCATACAT CACCATATCT TCACCAGTCT CATCCTAGTG
TTCATCATCC TCAGTAGTGT GTCCCTGGCT GCTGAGGACC CATCCGAGC
TCACTCCTTC CGAAACCATA TTCTGGGATA TTTTGATTAT GCCTTCACCT
CCATATTCAC TGTGGAGATT CTACTCAAGA TGACAGTGTT TGGGGCCTTC
CTGCACCGAG GCTCTTTCTG CCGTAGCTGG TTCAATCTGT TGGATCTCCT
TGTGGTCAGT GTGTCCCTCA TCTCCTTCGG CATCCACTCC AGTGCCATCT
CAGTTGTGAA GATTCTCCGA GTCCTCCGAG TCCTGCGGCC TCTCCGAGCC
ATCAACAGAG CCAAGGGACT CAAGCATGTG GTGCAGTGTG TGTTCGTGGC
CATCCGGACC ATCGGAAACA TCATGATTGT CACCACCCTC TTGCAGTTCA
TGTTCGCCTG CATTGGTGTT CAGCTGTTCA AGGGAAAATT CTACAGTTGC
ACTGATGAGG CCAAACACAC CCTGAAAGAA TCGAAGGGCT CCTTCCTCAT
CTACCCTGAT GGAGATGTGT CACGACCTTT GGTCCGGGAG CGGCTCTGGG
TCAACAGTGA TTTTAACTTT GACAACGTCC TTTCAGCCAT GATGGCCCTG
TTCACTGTCT CTACCTTTGA AGGCTGGCCT GCGCTACTAT ACAAGGCCAT
AGATGCAAAC GCAGAAGATG AGGGCCCTAT CTACAATTAC CATGTGGAGA
TATCAGTATT CTTCATTGTC TACATCATCA TCATCGCCTT CTTCATGATG
AACATCTTTG TGGGCTTTGT TATCATCACA TTCCGTGCCC AGGGAGAGCA
GGAGTACCAA AACTGTGAAC TGGACAAGAA CCAGCGCCAG TGTGTGGAAT
```

Figure 9d

```
ATGCCCTCAA AGCTCAGCCA CTCCGCCGAT ACATCCCTAA GAATCCTCAT

CAGTACCGCG TGTGGGCCAC TGTGAACTCT CGTGCCTTTG AGTACCTCAT

GTTTCTGCTC ATCCTGCTCA ACACGGTGGC CCTAGCCATG CAGCACTATG

AACAGACTGC TCCCTTTAAC TATGCCATGG ACATCCTCAA CATGGTCTTC

ACTGGCCTCT TCACCATTGA GATGGTGCTC AAAATCATCG CCTTTAAACC

CAAGCATTAC TTTGCAGATG CCTGGAATAC GTTTGATGCT CTCATTGTAG

TGGGCAGTGT AGTCGACATC GCCGTCACAG AAGTCAATAA CGGAGGCCAT

CTTGGCGAGA GTTCAGAGGA CACGTCCGC ATATCTATCA CGTTCTTTCG

CCTCTTCCGA GTCATGAGGC TGGTCAAGCT TCTGAGTAAG GGTGAAGGGA

TCCGCACACT GCTCTGGACA TTCATCAAGT CTTTCCAGGC CTTGCCCTAT

GTGGCACTTC TCATAGCAAT GATATTCTTC ATCTATGCAG TCATTGGCAT

GCAGATGTTT GGCTTGGTGG CTCTTCAGGA CGGCACGCAG ATAAATCGAA

ACAACAATTT CCAGACCTTT CCGCAGGCTG TGCTGCTTCT GTTCAGGTGT

GCCACTGGTG AGGCCTGGCA AGAGATAATG CTAGCCAGCC TTCCAGGAAA

TCGATGTGAC CCTGAGTCTG ACTTTGGCCC AGGCGAGGAA TTTACCTGTG

GTAGCAGTTT TGCCATCGTC TACTTCATCA GCTTCTTTAT GCTCTGTGCC

TTCCTGATTA TAAATCTCTT TGTGGCTGTA ATCATGGATA ACTTTGATTA

CCTAACCAGA GATTGGTCTA TCCTGGGACC CCACCACCTT GATGAATTCA

AGAGGATCTG GTCTGAATAT GACCCCGGAG CCAAGGGCCG CATCAAGCAC

TTGGATGTGG TTGCCCTGCT GAGACGCATC CAGCCCCAT TGGGATTTGG

AAAGCTATGC CCACACCGAG TGGCCTGCAA GAGACTCGTG GCAATGAATG

TGCCCCTCAA CTCAGATGGA ACAGTGACAT TCAACGCTAC ACTCTTTGCC

CTGGTGCGGA CATCCCTGAA GATCAAGACA GAAGGGAACC TGGATCAAGC

CAACCAGGAG CTTCGGATGG TCATCAAAAA GATCTGGAAG CGGATAAAGC
```

Figure 9e

```
AGAAATTGTT GGATGAGGTC ATCCCTCCTC CCGATGAGGA GGAGGTCACT
GTGGGAAAAT TCTATGCCAC ATTCCTGATC CAAGATTATT TCCGAAAATT
CCGGAGAAGG AAAGAAAAGG GGCTACTAGG AAGAGAGGCC CCAACAAGCA
CATCCTCTGC CCTCCAGGCT GGTCTAAGGA GCCTGCAGGA CTTGGGTCCT
GAGATCCGTC AAGCCCTCAC CTATGTCACT GAGGAAGAAG AGGAAGAGGA
AGAGGCAGTG GGTCAGGAGG CTGAGGAAGA GGAAGCTGAG AACAACCCAG
AACCATACAA AGACTCCATA GACTCCCAGC CCCAATCTCG ATGGAACTCT
AGGATTTCGG TGTCTCTACC TGTTAAGGAG AAACTTCCAG ATTCTCTCTC
AACTGGGCCG AGTGATGATG ATGGGCTGGC TCCCAACTCC AGGCAGCCCA
GTGTGATACA GGCTGGCTCC CAACCACACA GGAGAAGCTC TGGGGTTTTC
ATGTTCACTA TCCCGGAAGA AGGAAGTATT CAGCTCAAGG GAACTCAAGG
GCAGGACAAT CAGAATGAGG AACAGGAACT CCCTGACTGG ACTCCTGACC
TGGATCGAGC AGGCCGGGAC TCCTTCGAAC CCAGTCCTTT TACCACCTCA
CTGGTCCAGC AACACGTAAA CGGGCACATG TCGACGCCGA CGTTTGCTGC
CCCCCACGCC TGCAGGTCGG AGCCCTCCTT CACCATCCAG TGTCTGCAAC
GCCTGGGCAG TTGTGAAGAT TTACCTATCC CAGGCACCTA CCATCGTGGA
CGGACCTCAG GACCAAGCAG GGCTCAGGGT TCCTGGGCAG CCCCTCCTCA
GAAGGGTCGA CTGCTATATG CCCCCCTGTT GTTGGTGGAG GAATCTACAG
TGGGTGAAGG ATACCTTGGC AAACTTGGCG GCCCACTGCG TACCTTCACC
TGTCTGCAAG TGCCTGGAGC TCATCCGAAT CCCAGCCACC GCAAGAGGGG
CAGTGCTGAC AGTTTGGTGG AGGCTGTGCT CATCTCCGAA GGCCTAGGTC
TCTTTGCCCA AGACCCACGA TTTGTGGCCC TGGCCAAGCA GGAGATTGCA
GATGCATGTC ACCTGACCCT GGATGAGATG GACAGTGCTG CCAGTGACCT
GCTGGCACAG AGAACCATCT CCCTTTACAG TGATGAGGAG TCTATTCTTT
```

Figure 9f

CCCGCTTTGA TGAAGAGGAC CTGGGAGATG AGATGGCCTG TGTCCATGCC

CTCtaaatcc ttacccctca tctactgctc aataaactcc ctgcccttcc ttcccccaga ggaggcagqc atqqaccaca aaaaaaaaaa aaaaaaaaa aaa

Figure 10a

MSESEVGKDT TPEPSPANGT GPGPEWGLCP GPPTVGTDTS GASGLGTPRR
RTQHNKHKTV AVASAQRSPR ALFCLTLTNP IRRSCISIVE WKPFDILILL
TIFANCVALG VYIPFPEDDS NTANHNLEQV EYVFLVIFTV ETVLKIVAYG
LVLHPSAYIR NGWNLLDFII VVVGLFSVLL EQGPGRPGDA PHTGGKPGGF
DVKALRAFRV LRPLRLVSGV PSLHIVVNSI MKALVPLLHI ALLVLFVIII
YAIIGLELFL GRMHKTCYFL GSDMEAEEDP SPCASSGSGR SCTLNHTECR
GRWPGPNGGI TNFDNFFFAM LTVFQCITME GWTDVLYWMQ DAMGYELPWV
YFVSLVIFGS FFVLNLVLGV LSGEFSKERE KAKARGDFQK LREKQQMEED
LRGYLDWITQ AEELDLHDPS VDGNLASLAE EGRAGHRPQL SELTNRRRGR
LRWFSHSTRS THSTSSHASL PASDTGSMTD TPGDEDEEEG TMASCTRCLN
KIMKTRICRH FRRANRGLRA RCRRAVKSNA CYWAVLLLVF LNTLTIASEH
HGQPLWLTQT QEYANKVLLC LFTVEMLLKL YGLGPSVYVA SFFNRFDCFV
VCGGILETTL VEVGAMQPLG ISVLRCVRLL RIFKVTRHWA SLSNLVASLL
NSMKSIASLL LLLFLFIIIF SLLGMQLFGG KFNFDQTHTK RSTFDTFPQA
LLTVFQILTG EDWNVVMYDG IMAYGGPFFP GMLVCVYFII LFICGNYILL
NVFLAIAVDN LASGDAGTAK DKGREKSSEG NPPKENKVLV PGGENEDAKG
ARSEGAAPGM EEEEEEEEEE EEEEEEEEN GAGHVELLQE VVPKEKVVPI
PEGSAFFCLS QTNPLRKACH TLIHHHIFTS LILVFIILSS VSLAAEDPIR
AHSFRNHILG YFDYAFTSIF TVEILLKMTV FGAFLHRGSF CRSWFNLLDL
LVVSVSLISF GIHSSAISVV KILRVLRVLR PLRAINRAKG LKHVVQCVFV
AIRTIGNIMI VTTLLQFMFA CIGVQLFKGK FYSCTDEAKH TLKESKGSFL
IYPDGDVSRP LVRERLWVNS DFNFDNVLSA MMALFTVSTF EGWPALLYKA

Figure 10b

IDANAEDEGP IYNYHVEISV FFIVYIIIIA FFMMNIFVGF VIITFRAQGE

QEYQNCELDK NQRQCVEYAL KAQPLRRYIP KNPHQYRVWA TVNSRAFEYL

MFLLILLNTV ALAMQHYEQT APFNYAMDIL NMVFTGLFTI EMVLKIIAFK

PKHYFADAWN TFDAIVVGSV VDIAVTEVNN GGHLGESSED TSRISITFFR

LFRVMRLVKL LSKGEGIRTL LWTFIKSFQA LPYVALLIAM IFFIYAVIGM

QMFGLVALQD GTQINRNNNF QTFPQAVLLL FRCATGEAWQ EIMLASLPGN

RCDPESDFGP GEEFTCGSSF AIVYFISFFM LCAFLIINLF VAVIMDNFDY

LTRDWSILGP HHLDEFKRIW SEYDPGAKGR IKHLDVVALL RRIQPPLGFG

KLCPHRVACK RLVAMNVPLN SDGTVTFNAT LFALVRTSLK IKTEGNLDQA

NQELRMVIKK IWKRIKQKLL DEVIPPPDEE EVTVGKFYAT FLIQDYFRKF

RRRKEKGLLG REAPTSTSSA LQAGLRSLQD LGPEIRQALT YVTEEEEEE

EAVGQEAEEE EAENNPEPYK DSIDSQPQSR WNSRISVSLP VKEKLPDSLS

TGPSDDDGLA PNSRQPSVIQ AGSQPHRRSS GVFMFTIPEE GSIQLKGTQG

QDNQNEEQEL PDWTPDLDRA GRDSFEPSPF TTSLVQQHVN GHMSTPTFAA

PHACRSEPSF TIQCLQRLGS CEDLPIPGTY HRGRTSGPSR AQGSWAAPPQ

KGRLLYAPLL LVEESTVGEG YLGKLGGPLR TFTCLQVPGA HPNPSHRKRG

SADSLVEAVL ISEGLGLFAQ DPRFVALAKQ EIADACHLTL DEMDSAASDL

LAQRTISLYS DEESILSRFD EEDLGDEMAC VHAL

Figure 11a

```
  1  h  ATGTCGGAATCTGAAGGCGGGAAAGACACACCCCTGGTCTCCCGAGAGCCCCAGTCCAGCCAATGGGGCAGGCCCTGTGTGAAGGTGAAAGCAGT
     m  ATGTCGGAATCTGAAGTCGGGAAAGATACAACCCCAGAGAAAGATACAACCCCAGAGCCCCAGTCCAGCCAATGGGACTGGGCCCTCTGTCCTGGGCCTCCAACTGTGGGACTGATACCAGC 121  h  GGGGCATCAGGCCTAGGGACCCCTAAGCGAAGAAACCAGCCAAGCACACAGAGACAAGTGGCCAGTGCCAGTGGCCAGCGGTCACCTCGGCACTCTTCTCTGCCTCACCCTGGCCAATCCT
     m  GGGGCGTCAGGCCTGGGACCCCCAAGAAGAAGGAGGACCCCAGCCAGCCACACAAACACAAGACTGTGGCCAGTGCTGGCCAGTGCCAGTGGCCAGTGCCAGCAGTGCTCAGATCACCTCGAGATCACCTCGAGCGCTCTTCTGCCTCCACCCTTACTAATCCC 241  h  CTGCGACGGTCCTGCATCAGCATCGTGAGTGAAGCCCTTCGACATCTTCTGCCAACTGCGTGGCCCTGGGAGTTTACATCCCCTTCCTGAGGACGACTCC
     m  ATTCGTCGGTCCTGCATCAGCATTGTAGAGTGAAGCCCTTTTGATATTCTCATCCTCCTGACAATCTTTGCCAACTGCGTGGCATTGGGGTATATATCCCCTTCCTGAGGACGACTCC 361  h  AACACTGCCAACCACAACCTGAGACGCAGGTGAGTACGTATTCCTCGGTGATTTTCACTGTGGAGACGGTGCTCAAGATCGTGGCCTACGGCTGTCTCCACCCCAGCGCCTACATCCGC
     m  AACACTGCTAACCACACTTGGAACACAGTAGAATACGTGTTCCTGGTGATTTTCACCGTGGAGACAGTGCTCAAGATCGTCAAGATCGTAGCCTATGGGCTGGTGCTCCATCCCAGCGCCTATATTCGC 481  h  AATGGCTGGAACCTACTCGACTTCATCATCGTCGTTTCAGCGTTCTCTGTGGTCGGGCTGTTCAGCGTCTCGGCGTCCAGGCAGGGCCCCGACGGCCAGGGCCACACCGGGAAAGCCAGGAGGCTTC
     m  AATGGCTGGAACCTGCTCGACTTCATCATCGTCGTTGCGTTGGCATCTCGGCGTCTCGGCGTCTCGGCGTCTCGGCGTCTCGGCGTCTCGGCGTCTCGGCGTCTCGGCGTCTCGGCGTCGGCGTCTGTTCAGCGTCTGTTCAGCGTCTGTTCAGCGTCCATGGCGCGGCGTCCATATGGCGCGGCGCTGGAGCCCATATCCGGCGCTCGGAGCCCATATCTGGAGAAGACCTGGAGCCCATACTGGAGGAGGCTTC 601  h  GATGTGAAGGCATTGAGGGCGTTTCGGTGCTGCTGCCCACTGAGGCTGGTCTGGGGTCGAACAAGGACCTGGGCGCGGCCAGGAGATGCCCAGGAGGATGCCCAGGAGGAGATCGAAAGCCAGGAGGCTTC
     m  GATGTAAAGGCACTGCGGCGCATTTAGGGTGCTGCTACGACCTCTAAGGCTAGTGTCCCGAGTCTGCACATAGTCGTCAATCGAAGGCCGCCTTGTGCCGCTTGTGCCGCTTGTGCCGCTTGTGCCGCTTGTGCCGCTTGTGCCGCTTGTGCCGCTTGTGCCGCTTGTGCCGCTTGTGCCGCTTGTGCCGCTTGTGCCGCTTCTGCACATT 721  h  GCACTGCTCGTGCTCTTCGTCATCATCATTTATGCCATCATTGGGCTCGAGCTGTGTTCCTTGGACGAATGCACAAGACGTGCTACTTCCTGGATCCGACATGGAAGCGGAGGAGACCCA
     m  GCCCTGTTGGTGCTCTTCGTCATTCATTACATTTACGCCATCATCGGACTCGAGCTATTCCTGAGCTATTCCTGAGATGCACAAGACATGCTACTTCCTGGATCGATATGAAGCAGAGAGGAGACCCA
```

Figure 11b

```
841   h   TCGCCCTGTGCTCTTCGGGATCAGGGCGTGCTGTGCACGCTGAACCAGACTGAGTGCCGCGGGCGCTGGCCAGGGCCAATGAGGCGCATCACCAACTTTGACAACTTCTTCTTCGCCATG
      m   TCACCTTGTGCATCTTCTGCCTCTGGGCGTTCATGCACACATGACGAGTGCCGCGGGCGCTGGCCAGGACCCAAGCGTGGCATCACGAACTTCGACAATTTTTCTTTGCCATG 961   h   CTGACAGTCTTCCAGTGTGTCACCATGGAAGGCTGACCGATGTGCTCTACTGATGCAAGATGCCCTGGGTGTACTTTGTGAGCCTTGTCATCTTTGGGTCC
      m   CTAACTGTGTTCCAGTGTATTACCATGGAAGGCTGACAGACGTCCTCTACTGATGCAGGATGCCATGGGTGTATGAGCCTGCCTTGGGTGTACTTTGTGAGCCTTGTCATCTTTGGGTCC 1081  h   TTCTTCGTCCTCAACCTTGTCTTGGCCTCCCTGAGTGGGAGTTCTCCAAGGAGAGAGAAAGCGAAAGCTCGCGGGACTTCCAGAAGCAGCGGGAGAAGCAGCAGATGGAGGAAGAC
      m   TTCTTTGTCCTCAACCTTGTGCTTGGAGTCGGGAGTTCCTAAGCCTGAAGCGGGAGTCTCTCCAAGGAGAGTTCTCCAAGAAGCACGAGGTGACTTTCAGAAGCTTCGGGAGAAGAAGCAGGAAGAAGAC 1201  h   CTGCGGGGCTACCTGGACTGGATCACTCAAGCCTGAAGAGCGAAGAGCTGGACATGGAGGACCCCCTCCGCCGATGACAACCTTGGTTCTCATGCTGAAGAGGGCCGGGCGGCCATCGGCCACAGCTG
      m   CTTCGGGGCTACCTGGACTGGATCACACAGAGGTTAGACGTGAGGAGTTAGACCCTTCATGACCCTGCTGAAGAGGGACGCGGCAACTGGCTTCTCTTGCTGAAGAGGGACGCGGCGGCCATCGGCCACAACTG 1321  h   GCCGAGCTGACCAATAGGAGGCGTGGACGTCTGCGCGTCTGTGTTCAGTCATTCATTCTACTCGCTCCAGCAGCAGCTCCACACACTCCACCAGCCATGCCAGCCAGTGACAGCAGCCGGTTCCATGACAGAG
      m   TCAGAGCTGACCAATAGGAGGCGCGACGGCTGGATGGTTCGCAGTGTTCAGCGGACTGTTCAGCCACTCTACTGCTCCACACTCCACCAGCCCAGCCACCACGCCAGCCAGTGCTCCATGACAGAC 1441  h   ACCCAAGGCGATGAGGATGAGGAGGAGGGGCTTAAGCGCTGCCTGTACACGCTGCTAAACAAGATCATGAAAACAGAGTCTGCCGCCGAGCCAACCGGTGTCCTTCGGGCA
      m   ACCCCCTGGAGATGAGGATGAAGAGAGGGGACCATGGCTAGCTGCTGCTACACGCTGCCTAAACAGCTGCCTAAAACAAGATTATGAAAACAAGATCTGCCGCCACTTCCGCCGAGCCAACCGGGGTCTCCGTGCA 1561  h   CGCTGCCGTCGGGCCAGTGAAGTCCAATGCCTGCTACTGGGCTGTCCAATGCCTGCTGTTGCTCGTCTTCCTCAACACGTTGACCATCGCCTTCTCTGAGCACCACGGGCAGCCTGTGGCTCACCCAGATC
      m   CGCTGCCGGCCGGCCGTCAAGTCCAACGCCCGTCAACGCCCTGCTACTGGGCTGTCCAACGCCCGTCAACGCCCTGCTGTTGCTCGTCTTCCTCAACACGTTGACCATCGCCTTCTCTGAGCACCACGGGCAGCCTGTGGCTCACCCAGACC
```

Figure 11c

```
1681 h   CAGGAGTATGCCAACAAAGTGTGCTCTGTCTGTTCACGGTGGAGATGCTTCTCAAATTGTACGGTCTGGGCCTCTGCCTATGTGTCTTCCTTCTCAACCGCTTGACTGCTTTGTG
      :: :::::: :::::::::::: ::::::: :::::::::::::::: :::::: :::::::::::::::::::::: :::::: :: :::::::::::: :::::::::::
   m   CAAGAGTATGCCAACAAAGTTCTGCTCTGCTCCTTCACTGTGGAGATGCTCCTCAAACTGTACGGCCTGGGCCCTCTGTCTACGTTGCCTCCTTTTTCAACCGCTTGACTGCTCGTG 1801 h   GTCTGTGGGGCATCCTAGAGACCACCTTGGTGGAGGTGGGCCATCCAGCCCTTGGGCATCTCAGTGTCTCCGATGTGCGCCTCCTCAGGATCTTTAAGGTCACCAGACACTGGGCT
      :::::: ::::::::::::::::::::::::::::::::::::::::::::: :::::: :::::::::::::::::::::::::: ::::::::::::::::: :::::: ::
   m   GTCTGTGGGGCATCCTAGAAACCACCTTTGGTGGAGGTGGGCCATCCAGCCCTCTTGGCATCTCAGTGCTCCGATGTGTACGTCTCCTCAGGATCTTCAAGGTCACCAGGCACTGGGCA 1921 h   TCTCTGAGCAATCTGGTGGCATCCCTGCTCAATTCAATGAAATCCATCGCATCCTTGCTCTTCCTCCTTCATCATTATCTTCTCCCTGCTTGGCATGCAGCTGTTTGGGGC
      :: :::::::: :::::::::::::::::::::::::::: ::::::::::::::::::::::::::::: ::::: ::::::::::::::::::::::::: :::::
   m   TCCCTGAGCAATCTGGTGGCATCTTGCTCAATTCCATGAAGTCCATGTGTACGTCTCCTCAGGATCTTTCATCATCATCTTCTCCCTGCTTGGCATGCAGCTGTTTGGGGC 2041 h   AAGTTCAACTTTGACCAGACCCCACACCAAGCGAAGCACACCTTTCCCCCCAGGCCCCTCCTCCTCACTGTCTTTCAGATCCTGACAGGTGAGGACTGGAACGTGGTCATGTATGATGT
      ::::::::::::::::::::::::::::::::::: ::::::::::::::::::::::::::::::::::::::::::::::::::::::::::::::::::::::::::
   m   AAGTTCAACTTTGACCAGACCCCACACCAAGGAGCACACCTTTGATACCTTCCCCCAAGCCCTCCTCCTCACTGTCTTTCAGATCCTGACTGGTGAGGATTGGAACGTTGTCATGTATGATGT 2161 h   ATCATGGCATATGGTGTGGCCCCTTCTTCCCAGGAATGTTGGTGTGCATCTATTCATCATTCTCTTCATCTGTGGCAACTACATCCTGTTGAACGTGTTTCTTGCCATTGCTGTGGACAAC
      :::::::::::::::::::::::::::::: :::::::::::::::::::::::::::::::::::::::::::::::::::::::::::::::: :::::::::::::::::
   m   ATCATGGCCTACGGTGGGCCCCTTCTTCCCCAGGATGCTGGTGTGTTGTTTATTTCATCATCCTTTCATCTGTGGCAACTACATCCTGCTGAACGTGTTTCTTGCCATTGCCGTGGATAAC 2281 h   CTGGCCAGTGAGATGCAGGCACTGCCAAGGACAAGGGCCGGGAGAAGACAAGGCAATGAGAAGGATCTC-CCACAGGAGAATGAAGGCCTGGTGCCTGGTGTGGAGAAGAGGAAGAGGAGGG
      ::: ::::::: :::::::: :::::::::::::::::::::: :: :::::::::::::::::: :::::::::::::::: ::::::::::::::::::::: ::::::
   m   CTAGCCAGCGCGGGATGCAGGCACTGCCACTGCCAAAGATAAGGGCAGAGAGAGACAGTGA-AGGAAACCCTCCAAAGGAGAACAAAGTATTGGTGCCTGGTGGAGAGAATGAGGACGCAAAGGG 2401 h   TGCAAGGAGGAAGGAGCAGA------CATGGAGGAGGAGGAGGAGGA                    AGAAGAGAAGAAGAGGAAGAGGAAGAGGAAGAGGTGCAGGGGGTGTGGAACTCCTGCAGGA
      :::::  :::                :: :::::::::::::::                       ::::::::::::::::::::::::::::::::::: ::::::::::::::::::
   m   GCAAGAAGTGAAGAGGAGCAGCCAGGGCATGAGGAGGAGGAGGAGGAGGAGGAGGAGGAGGAGGAGGAAAGAAGAAGAAGAGGAAGAGGAAGAGGAAGAAAATGTCAGGACATGTGGAACTCTTGCAGGA
```

Figure 11d

```
2521 h  AGTTGTACCCAAGGAGAAGGTGGTACCCATCCCTGAGGGCAGCAGCGCCTTCTTCTGCCTCAGCCACACCCTCATCCACCATCATGTCTTCACCAA
      : ::: :::::::::::::::::::::::::::::::::::::::::::::::::: :::::: ::::: ::: ::: :::::::::::::::
     m  AGTAGTACCCAAGGAGAAGGTGGTACCCATCCCTGAAGGCAGTGCCTTCTTCTGCCTTAGCCACAGCAGTGCCTTCGGAAGGCTGCCACACTCTTCACCAG 2641 h  TCTTATCCTGTGTGTTCATCATCCTCAGCAGTGTGTCCCTGGCCGCTGAGGACCCCACTCCTTCCGAGCCCATCCGAGCCCAACCATATTCTGGGTTACTTCGATTATGCCTTCACCTCCATTTT
      : :::: :::: :::: ::::::::::::::::::::::::::::::::::::::::::::::::::::::::::::::::::::::::: :::: ::::::::::::::::::: :::::::::::: ::::
     m  TCTCATCCTAGTGTTCATCATCCTCAGTAGTGTGTCCCTGGCTGCTGAGGACCCCCATCCTGAGGACCTCACTCCTTCCGAAACCATATTCTGGATATTTTGATTATGCCTTCACCTCCATATT 2761 h  CACTGTGAGATTCTACTAAAGATGACAGTGTTTGGGGGCCCTTCCTGCACCGCGGCTCCTTCTGCCGTAGCTGGTTAATATGTTGATCTGTGGTGTCCCTCATCTCCTT
      : ::::::::::::::::::::: :::: ::::::::::::::::::::::::::::::::::::::::::::::::::::::::::::::::::::::::::: ::::::
     m  CACTGTGAGATTCTACTCAAGATGACAGTGTTTGGGGGCCCTTCCTGCACCGCGGCTCTTTTCTGCCGTAGCTGGTTCAATCTGTTGATCCTGTGGTGTCCCTCATCTCCTT 2881 h  TGGCATCCACTCCAGCGCCATCTCGGTGGTGAAGATTCTCGAGTACTCCGAGTGCGGCCCCTCCGAGCCATCAACAGGGCCAAGGACTCAAGCATGTGGTGCAGTGTGTATTTGT
      : ::::::::::::::::::::::: ::::::::::::::::::::::::::::::::::: :::::::::::::::::::::::::::::::::::::::::: ::: :::
     m  CGGCATCCACTCCAGTGCCATCTCCAGTGTGAAGATTCTCCGAGTCCTCCGAGTGCGGCCCCTCTCCGAGCCATCAACAGAGCCAAGGACTCAAGCATGTGGTGCAGTGTGTTCGT 3001 h  GGCCATCCGACCATCGGAGAAACATCATGATTGTCACCACACTTCTGCAATTTATGTTCGCTGCATCGGGGTGCAGCTTCAAGGGAGGAAATTCTACACCTGCACGGACGAGGCCAAACA
      : :::::::::::::::::::: :::::::::::::::::::::::::::::::: ::::::::::::::::::::::::::::: :::::::::::::::::::::::::::::::
     m  GGCCATCCGACCATCGGAAACATCATGATTGTCACCACACTTCTGCAGTTCATGTTCGCCTGCATCGGGTGCAGCTTCAAGGGAGGAAATTCTACAGTGCACTGACGTGAGGCCAAACA 3121 h  CACCCCTCAAGAATGCAAGGCTCAAGGGCTCCTTCCCTGGTATACCCAGATGGAGACGTGTCACGGCGTGTCTGGGTCAACAGTGATTTCAACTTTGACAATGTCCTTTCAGC
      : :::: :::::::: ::::::::::::::::::::::::::::::::::::::::::::::::::::::::::::::::::::::::::::::::::::::::::: :::::
     m  CACCCTGAAAGAATCGAAGGCTCCTTCCCTCATCTACCCTGATGGAGATGTGTCACAGTGTGATTTTAACTTTGACAACGTCCTTTCAGC 3241 h  CATGATGGCCCTGTTCACTGTCTCCACCTTTGAAGGCTGGCCTGCACTGCTATACAAGGCCATGCGATGCATATGCAGAGAGACCATGGCCCCATCTATAATTACCGTGTGGAGATCTCAGT
      : :::::::::::::::::::::::::::::: :::::::::::::::::::::::::::::::::::::::::::::::::: :::::::::::::::::::::::::::::::::::::
     m  CATGATGGCCCTGTTCACTGTCTCCACCTTTGAAGGCTGGCCTGCACTGCTATACAAGGCCTATCGCAGCCGCTACTATACAAGCCATGAGCAGAGAAGATGAGGGCCCATCTACAATTACCATGTGGAGATATCAGT
```

Figure 11e

```
3361 h  GTTCTTCATTGTCTACATCATCATCATTGCGTTCTTCATGATGAACATCTTCGTGGGCTTCGTGTCATCATCACTTTCCGTGCCCAGGGCGAGCAGGAGTACCAAAACTGTGAGCTGGACAA
     m  ATTCTTCATTGTCTACATCATCATCATCATGCCTTCTTCATGATGAACATCTTTGTGGGCTTTGTTATCATCACATTCCGTGCCCAGGAGAGCAGGAGTACCAAAACTGTGAACTGGACAA 3481 h  GAACCAGCGTCAATGTGTGGAATATGCCCTCAAGGCCCACTCCAGCCGTTACATCCCCAAGAACCCGATCAGTATGTGTGGGCCACTCTGTGCCTGCCTTTGAGTACCT
     m  GAACCAGCGCCAGTGTGTGGAATATGCCCTCAAAGTCCCCACTCCGCCGATACATCCTCAAGAATCTCATCAGTATCCGTGTGGGCCACTGTGAACTCTCGTGCCTTTGAGTACCT 3701 h  GATGTTCCTGCTCATCCTGCTCAACACAGTTGCCCTAGCCATGCAGCACTATGAGCAGACTGCTCCCTTCAACTATGCCATGACATCCTCAACATGGTCTTCACTGGCCTCTTCACTAT
     m  CATGTTTCTGCTCATCCTGCTCAACACGGTTGCCCTGAGAGTTCAGACGCCATGCAGCACTATGAACAGACTGCTCCCTTTAACTATGCCATGACATCCTCAACATGGTCTTCACTGGCCTCTTCACCAT 3821 h  TGAGATGTGTGCTCAAAATCATCGCCTTCAAGCCCAAGCCATTACTTCACTGATGCCTGGAACACGTTTGACGCTCTCTTATTGTGGGCAGCAGTGATATTGCCGTCACTGAAGTCAA
     m  TGAGATGTGCTCAAAATCATCGCCTTTAAACCCAAGCCATTACTTACTTTGCAGATGCCTGGAATACGTTTGATGCTCTCATTGTAGTGGGCAGTGTAGTCGACATCGCCGTCACAGAAGTCAA 3941 h  TAATGGTGGCCACCTTGGCCGAGAGCTCTGAGGACAGCTCCCGCCATTTCCATTACCTTCTTTCGCCTCTTCCGAGTTATGCGGCTGGTCAAGCTTCCAGTAAGGGTGAAGGGATCCGCAC
     m  TAACGGAGGCCATCTTGGCGAGAGTTCAGAGGACAGTTCAGAGGACTGCTCCCGCCATATCTATCACGTTCTTTCGCCTGTCAAGCTTCTGAGTAAGGGTGAAGGGATCCGCAC 4061 h  ATTGCTCTGGACATTCATCAAGTCCTTCCAGGCCTTCTCCAGGCCTCTCTCATGCCAATGATATTCTTCATCTATGCCGTCATTGGCATGCAGATGTTCGGCAAGGTGCTCTTCA
     m  ACTGCTCTGGACATTCATCAAGTCTTTCCAGGCCTCTTTCCAGGCCACTTCTCATGTGGCACTTCTCATAGCAATGATATTCTTCATCATTGGCTTGGTGCTGGCTCTTCA 4181 h  GGATGGCACACAGATAAACCGAAACAACTTCCAGACCTTTCCACAGGCTGTGCTGCTCTTCAGGTGTGCCACTGGTGAGGCATGGCAGGAGATAATGCTTGCCAGCCTTCCCGG
     m  GGACGGCACGCAGATAAATCGAAACAACAATTTCCAGAGACCTTTCCAGGCTGTGCTGCTCTTCAGGTGTGCCACTGGTGAGGCTGGCAAGAGATAATGCTAGCCAGCCTTCCAGG
```

Figure 11f

```
4301 h  AAATCGGTGTGATCCTGAGTCTGACTTCGGCCCTGGTGAAGAGTTTACCTGTGGTAGCAATTTTGCCATGCTCTTCATCAGCTTCTCATCGCCTATTTCATCAGCTTCTGTGCCTTCCTGATCATAAATCT
     m  AAATCGATGTGACCCTGAGTCTGACTTCGGCCCTGGTGAAGAGGAATTTACCTGTGGTAGCAGTTTTGCCATGCTCTACTTCATCAGCTTCTTTATGCTCTGTGCCTTCCTGATTATAAATCT 4421 h  CTTTGTGGCTGTGATCATGGACAACTTTGATTATCTCACCAGAGATTGGTCCATCCTGGGCCCCATCACCTTGATGAATTCAAGAGGATCTGGTCTGAATATGACCCTGGGCCAAGGG
     m  CTTTGTGGCTGTAATCATGGATAACTTTGATTACCTAACCAGAGATTGGTCTATCCTGGGACCCCACCACCTTGATGAATTCAAGAGGATCTGGTCTGAATATGACCCCGGAGCCAAGGG 4541 h  CCGCATCAAACACTTGGATGTGGTTGCCCTGCTGAGACGTATCCAGCCCCCTCTGGGATTTGGGAAGCTGTGCCACCGAGTGTGCCTGCAAGAGACTTGTGCAATGAACATGCCCCT
     m  CCGCATCAAGCACTTGATGTGGTTGCCCTGCTGAGACGCCATCCAGCCCCCATTGGGATTGGGATTGGAAAGCTATGCCCACCGAGTGCCAAGAGACTCGTGCAAGACTCTGCAATGAATGTGCCCCT 4661 h  CAACTCAGATGGACGGTGACATTCAACGCCACACTCTTTGCCCTGGTCCGGACATCCTGAAGATCAAAACAGAGAAGGAACCTGGAGCAAGCCAACCAGGAGCTGCGGATTGTCATCAA
     m  CAACTCAGATGAACAGTGAACATTCAACGCTACACTCTTTGCCCTGGTGCGGACATCCTGAAGATCAAGACAGAGAAGGAACCTGGATCAAGCAACCAGGAGCTTCGATGGTCATCAA 4681 h  AAAGATCTGGAAGCGGATGAAACAGAAGAGCTGCTAGATGAGGTCATCATCCCCCACCAGACGAGGAGGAGGTCACCGTGGCAAATTCTACGCCACATTTCTGATCCAGGACTATTTCCGCAA
     m  AAAGATCTGGAAGCGGATAAAGCAGAAATTGTTGATGAGGTCATCATCCCCATGAGGAGGAGGTCACTGTGGGAAAATTCTATGCCACATTCCTGATCCAAGATTATTTCCGAAA 4801 h  ATTCCGGCGGAGGAAGAAAAGGGCTACTAGGCCAACGACGCGCCGCCCTTCCCGCCTCTCAGCACCCTCTTCCGCCCCTTCAGGCTGGTCCTGCGGAGCCTGTGAGATGCGGCAGGCCCT
     m  ATTCCGGAGAAGGAAGAAAAGGGGCTACTAGGAAGAAGAGAGCCCCAACAGCACATCCTCGCCCTCTGCCCTCTAAGGAGCTGGTCCTGAGATCCGTCAAGCCCT 4921 h  CACCTGTGACAC----AGAGGAGGAGGAAGA------AGAGGGGCAGGAGGGAGTGGAGGAGGAGATGAAAAGGACTTGAAACTAACAAAGCCACGATGGTCTCCCAGCCCTCAGC
     m  CACCTATGTCACTGAGGAAGAAGAGGAAGAGGAAGAGGAAGCTGAGGAGGCTGAGGAGGTCAGGAGGTCAGGAGGCAGTGGGTCAGGAGCTGAGGAGGCTGAGGAGCAACCCAGAACTGAGAACAATCACAAAGACTCCATAGACTCCAAGCCCCAGCCCCAATC
```

Figure 11g

```
5041 h  TCGCGCGGGCTCCGGGATTTCTGTGTCTCTGCCTGTCGGGGACTTCCAGATTCACTCTCCTTTGGGCCAGTGATGATGACAGGGGACTCCCACCTCCAGTCAGCCCAGTGTGCC
        :::  :::  ::::::::  :::::               ::::::      ::     ::::::::         :::::      :::
     m  TCGATGAACTCTAGAGATTTCGGTGTCTCTACCTGTTAAGGAGAAACTTCCAGATTCTCTCTCAACTGGGCCGAGTGATGGCTGGCTGATGATGAGCCCAGTGTGAT 5161 h  CCAGGCTGGATCCAACACCCACAGGAGAGGCTCTGGGCTCTCTCATTTTCACCATCCCAGAAGAAGGAAATTCTCAGCCCAAGGAACCAAAGGGCAAAACAAGCAAGATGAGGATGAGGA
        :              :: ::::                       :::::::    ::::::::::  ::            ::          ::      :::::    :: ::::::
     m  ACAGGCTGGCTCCCAACACACAGAGAGAAGCTCTGGGGTTTTCATGTTCACTATCCCGGAAGAAGAAGTATTCAGCTCAAGGGACAATCAGAATGAGGAACAGGA 5281 h  AGTCCCTGATCGGCTTTCCTACCTAGAT-GAGCAGGCAGGGACTCCCCCGTGCTCAGTCCTTTGCCACCTCACAGAGCTCAGATACATGGACACTGTTACCACGCCGCCGTC
        :  ::::::   ::   ::     ::::::::::       ::      :: :::  :::::::::::::::::::: ::        ::       :  :::::::::::
     m  ACTCCCTGACTGGACTGAGTCGA-GCCCTCCTTCACCATCCAGTGCTCTGCAACCCAGTCCTTCGAACCCAGTCCTCCTCAGTCCCAGACCCTCACTG-GTCCAGCAACACGTAAACGGGCACATG--TCGACGCCGACGTT 5401 h  TGCTGCCCCCACACTCGAGTCGGAAGCCCTCCTTCACCATCCAGTGCTCGAGCAGCAGGGCAGTGCTCTGCGAGCGCCAGGGCAGTGTGTGAGGATTTACCCATTCATCGTCGGGCGAAATTCAGGGC
        :  :::::      :::::::: :::: ::::::                                            :::::    :: ::                ::: ::  :::::::::::
     m  TGCTGCCCCCCACGCCTGCAGTCGGA-GCCCTCCTTCACCATCCACCAGTGTCTCTGCAACGCCTGGGCAGTGTGAGATTGTGAAGATTTACCTATCCCAGGCACCATCCGGCACCATCGGGCAGCCCTCGAAACTTGGCGGCC 5521 h  CCAATAGGGCTCAGGTTCCTGGGCAACACCACCTCAGCGGGTCGGCTCCCTGTATGCCCCGCTGTTGTTGGTGGAAGAGAGGCGCAGCGGGAGGGGTACCTCGGCAGATCCAGTGGCC
         :  :::::::::::     :::::                            ::                :: ::         :::::    ::::   :::::::        ::
     m  CAAGCAGGGCTCAGGGTTCCTGGGCAGCAGCCCCCTCCTCAGAAGGGTCGACTGCTATATGCCCCCTGTTGTTGGTGGAGGAATCTACAGTGGTGAAGGATACCTTGGCAAACTTGGCGGCC 5641 h  CACTGCGCACCTTCACCTGTCTGCACGTGCCTGGAACCCACTCGGACCCCAGCCATGGGAAGAGAGGGGCAGTGCCGACAGCTTGGTGTGAGAGCTGTGCTTATCTCAGAGGGTCTGGGCCTCT
         :: ::::::  :::::::::::      :::::::      :::::::::::::::  ::::::::::::::::::::::::::::::::::: :::     :: ::::
     m  CACTGCGTACCTTCACCTGTCTGCAAGTGCCTGGAGCTGCTCATCCGAATCCCAGCACCGCCGGATCCCAGCACCGCCGGATCCCAGCACCGCCGAAGAGGGCAGTGCCTGACAGTTTGGTGCTGACAGTTGCTCATCTCCGAAGGCCTAGGTCTCT 5761 h  TTGCTCGAGACCCACGTTTCGTGGCCCTGGCCAAGCAGGAGATTGCAGATGCGTCGCCTGACGCTGGATGAGATGCTGGCACTGCTGGCACAGGGAACCAGCTCTC
        :::::        ::                                          :::::::::::::::::::::::::::          :  :::::::::
     m  TTGCCCAAGACCCACGATTTGTGGCCCTGGCCAAGCAGGAGATTGCAGATGCATGTCAGATGCATGTCACCTGACGTCGATGAGATGCTGGCACTGCTGGCACAGAGAACCATCTCCC
```

Figure 11h

```
5881 h  TCTATAGCCGACGAGGAGTCCATCCTCTCCCGCTTCGATGAGGAGGACTTGGGAGACGAGATGGCCTGCGTCCACGCCCCTCTGAATTCCCACCCCTCCCAACTGCTCAATAAACCTCCTG
        : :: ::::::::  ::   :::::::::  ::::   ::::::::  :::::: :::  ::::::::::::::::: :: :::::  : :::::::: : ::::::::::::::::::
     m  TTTACAGTGATGAGGAGTCTATTCTTTCCCGCTTTGATGAAGAGGACCTGGGAGATGAGATGGCCTGTGTCCATGCCCTGTGTCCTAAATCCTTACCCCTCCATCTACTGCTCAATAAACTCCCTG 6001 h  CCCTCCCCTCCCCAGGAGGCAGGCATGGACCACAAAAAAAAAAAAAAAA
        ::::  :: :::::::::::::::::::::::::::: ::::::::::
     m  CCCTTCCCTTCCCCCAGAGGAGGCAGGCATGACCACAAAAAAAAAAAAAAAAA
```

RETINAL CALCIUM CHANNEL (ALPHA)$_{1F}$-SUBUNIT GENE

This application is a continuation of international application number PCT/CA99/00514, filed Jun. 2, 1999 which claimed priority to U.S. Provisional Patent application No. 60/087,635, filed of Jun. 2, 1998.

FIELD OF THE INVENTION

This present invention relates to calcium channel compositions. In particular, this invention relates to a mammalian gene encoding a retinal calcium channel subunit polypeptide, herein referred to as CACNA1F, wherein mutations of CACNA1F may cause a type of X-linked congenital stationary night blindness.

REFERENCES

The following references are cited in the application as numbers in brackets ([ ]) at the relevant portion of the application. Each of these references is incorporated herein by reference.

1. Héon and Musarella, "Congenital stationary night blindness: a critical review for molecular approaches", in *Molecular Genetics of Inherited Eye Disorders* (eds. Wright, A. F. & Jay, B.) pp 277–301 (Harwood Academic Publishers, London, 1994).
2. Miyake, et al., "Congenital stationary night blindness with negative electroretinogram", *Arch. Ophthalmol.* 104, 1013–1020 (1986).
3. Weleber. et al., "Aaland Island Eye Disease (Forsius-Eriksson syndrome) associated with contiguous deletion syndrome at Xp21", *Arch. Ophthalmol* 107:1170–1179.
4. Boycott, et al., "Evidence for genetic heterogeneity in X-linked congenital stationary night blindness." *Am. J. Hum. Genet.* 62:865–875 (1998).
5. Catterall, "Structure and function of voltage-gated ion channels". *Annu. Rev. Biochem.* 64, 493–531 (1995).
6. Fishman and Sokol, "Electrophysiologic Testing in Disorders of the Retina, Optic Nerve, and Visual Pathway", (Am. Acad. Ophthal., San Francisco, 1990).
7. Wilkinson and Barnes, "The dihydropyridine-sensitive calcium channel subtype in cone photoreceptors", *J. Gen. Physiol.* 107, 621–630 (1996).
8. Boycott, et al., "A 2-megabase physical contig incorporating 43 DNA markers on the human X chromosome at p11.23-p11.22 from ZNF21 to DXS255", *Genomics* 33, 488–497 (1996).
9. Schindelhauer, et al., "Long-range mapping of a 3.5-MB region in Xp11.23-22 with a sequence-ready map from a 1.1-Mb gene-rich interval", *Genome Res* 6. 1056–1069 (1996).
10. Boycott, et al., "Construction of a 1.5 Mb bacterial artificial chromosome (BAC) contig in Xp11.23, a region of high gene content" *Genomics,* 48:369–372 (1998).
11. Fisher, et al., "Sequence-based exon prediction around the synaptophysin locus reveals a gene-rich area containing novel genes in human proximal Xp". *Genomics* 45, 340–347 (1997).
12. Williams, et al., "Structure and functional expression of a α1, α2, and β subunits of a novel human neuronal calcium channel subtype", *Neuron* 8, 71–84 (1992).
13. Schuster, et al., "The IVS6 segment of the L-type calcium channel is critical for the action of dihydropyridines and phenylalkylamine", *EMBO J.* 15.2365–2370 (1996).
14. Boycott, et al., "Integration of 101 DNA markers across human Xp11 using a panel of somatic cell hybrids", *Cell Cytogenet. Genet.* 76. 223–228 (1997).
15. Nathans and Hogness, "Isolation, sequence analysis, and intron-exon arrangement of the gene encoding bovine rhodopsin", *Cell* 34, 807–814 (1983).
16. Bech-Hansen, et al., "Loss-of-function mutations in a calcium-channel $\alpha_1$-subunit gene in Xp11.23 cause incomplete X-linked congenital stationary night blindness", *Nature Genet.* 19: 264–267 (1998).

BACKGROUND

X-linked congenital stationary night blindness (CSNB) is a non-progressive retinal disorder characterized by night blindness, decreased visual acuity, myopia, nystagmus and strabismus [1]. Two distinct clinical entities of CSNB have been proposed, complete and incomplete CSNB [2]. In patients with complete CSNB, rod function is not detectable, whereas patients with incomplete CSNB have reduced, but not extinguished rod function. Furthermore, patients with complete CSNB may show moderate to severe myopia, whereas those with incomplete CSNB may show severe myopia to hyperopia [1]. A related disorder, Aaland Island eye disease (AIED), is suggested to be clinically indistinguishable from incomplete CSNB [3].

The biochemical defects underlying complete and incomplete CSNB are not known, but may be revealed by identifying the genes involved in these disorders. The CSNB gene(s) has been localized to the short arm of the human X-chromosome to region p11 by linkage analysis. However, it was uncertain whether the phenotypic variation results from genetic heterogeneity or a single locus exhibiting a wide variation in clinical phenotype [4]. Studies of three families with AIED have localized the AIED gene between DXS7 DXS255, overlapping with the chromosomal region harbouring the gene for incomplete CSNB.

Calcium channels are membrane-spanning hetero-oligomeric protein complexes, consisting of (alpha)$_1$, (alpha)$_2$, (beta)$_1$, (beta)$_2$, delta and gamma subunits [5], that allow controlled entry of Ca$^{2+}$ ions into the cytoplasm from the extracellular space or from intracellular stores. All cells throughout the animal kingdom and some plant, bacteria and fungal cells possess one or more types of calcium channel, which play a central role in the regulation of intracellular Ca$^{2+}$ concentration. Changes in intracellular Ca$^{2+}$ concentration are implicated in a number of vital processes, such as neurotransmitter release, muscle contraction, pacemaker activity and the secretion of hormones and other substances.

Voltage-gated calcium channels (types L, N, and P) are located on the plasma membrane of all excitable animal cells, such as neurons and muscle cells. L-type voltage-gated channels are distinguished pharmacologically from the other types by, among other features, their ability to bind dihydropyridine.

The (alpha)$_1$-subunits of L-type channels function as the pore and voltage sensors in calcium ion-selective pores [5]. Several diseases are known to be the result of mutations in calcium channel (alpha)$_1$-subunit genes, including human familial hemiplegic migraine and episodic ataxia type-2, hypokalemic periodic paralysis, muscular dysgenesis (mdg) and absence epilepsy in tottering mice. Mutations in an L-type calcium channel (alpha)$_1$-subunit gene cause myotonia in *C. elegans,* and a non L-type calcium channel (alpha)$_1$-subunit gene in Drosophilia (DmcalA) is a suggested candidate gene for the night-blind-A (nbA) and cacophony (cac) mutations.

Patients with CSNB, both complete and incomplete, show a reduced b-wave response on electroretinographic testing and decreased dark adaptation. Light-induced hyperpolarization of photoreceptor cells diminishes the release of neurotransmitters at their synaptic terminals, which in turn leads to the depolarization of outer nuclear bipolar and horizontal cells. This depolarization of bipolar cells causes the subsequent depolarization of Mueller cells, which appears largely to be the origin of the corneal positive b-wave [6]. The influx of calcium through dihydropyridine-sensitive calcium channels into photoreceptor cells has been shown to mediate the release of neurotransmitter [7]. Therefore, it is reasonable to presume that one or more L-type voltage-gated channels is involved in neurotransmission in the eye.

High-density physical maps of the Xp11.23 cytogenetic region have been constructed in YACs [8], cosmids [9], and BACs [10]. Large scale DNA sequencing in the Xp11.23 region has revealed several new genes. Computer analysis (GRAIL™ and GENE-ID™) of an extended genomic DNA sequence within the Xp11.23 region, has identified potential exons with homology to calcium channel (alpha)$_1$-subunit genes [28]. There was an indication that this gene was expressed in skeletal muscle, but this assertion may not be supported by the reported data [28]. The HUGO/GDB Nomenclature Committee has assigned this putative gene the name CACNA1F. The same putative gene was identified by the GENSCAN™, in a computer search of about 1,000 Kb of genomic DNA in this region (Xp11.23) by the Genome Sequencing Centre, Jena.

The identification of the gene which is causative of incomplete CSNB may allow for development of diagnostic tests for this disorder and risk assessment in affected families. As well, identification of the gene which is causative of incomplete CSNB will provide information as to the basic defect in this retinal condition, which could lead to effective methods for treatment or cure of the disorder. Furthermore, as the associated features of myopia, nystagmus and strabismus frequently observed in patients with incomplete CSNB may possibly be caused by calcium-regulated developmental pathways, identification of the retinal calcium channel gene may help to elucidate the molecular details of eye development and which may lead to treatment for related eye disorders or diseases.

The identification of a calcium channel gene that is expressed in the human retina. will aid in the elucidation of the role of calcium channels in retinal function. Knowledge of the structure of this gene will lead to studies of the structure-function relationships of the protein in the retinal environment. This knowledge, in turn, would be useful in the design and discovery of therapeutic agents whose activities are exerted by interacting directly or indirectly with a calcium channel.

Finally, given the diversity and importance of voltage-gated calcium channels in mammalian physiology, possession of cells which express selected channel subtypes would find use in the area of pharmacology and drug design. The identification of novel channel subtypes will expand this area of the medical arts.

SUMMARY OF THE INVENTION

The region on the short arm of the human X-chromosome, Xp11, which carries the gene for incomplete CSNB (CSNB2) was refined to a distance of 1.2 Mb, between DXS722 and DXS255.

A gene, CACNA1F, with homology to voltage-gated L-type calcium channel (alpha)$_1$-subunit genes, and that mapped to the CSNB2 minimal region was identified as being retina-specific. The complete cDNA sequence of this gene has been elucidated. Mutational analysis of CACNA1F in 31 families with incomplete CSNB revealed 15 different mutations, predicted to cause premature termination of, or missense mutations in, the protein product of CACNA1F. Together, these findings establish that mutations in CACNA1F cause incomplete CSNB.

In addition, mutational analysis of CACNA1F in four families with AIED revealed four different mutations, predicted to cause premature termination of, or missense mutations in, the protein product of CACNA1F. Two mutations were found in both a family diagnosed with incomplete CSNB and another family diagnosed with AIED, suggesting that these two disorders are the same. Therefore, in total, mutational analysis of 35 families with either incomplete CSNB or AIED revealed 17 mutations in the CACNA1F gene.

The murine orthologue of the human CACNA1F has been identified and the cDNA sequence determined. There is a high degree of sequence homology between the murine and the human CACNA1F gene, which is as high as 95% in some regions.

The present invention provides a mammalian nucleic acid sequence encoding a novel calcium channel (alpha)$_{1F}$-subunit expressed in the retina. Thus, in one aspect, this invention is an isolated DNA molecule comprising a sequence of nucleotides that encodes an (alpha)$_{1F}$-subunit of a mammalian retinal calcium channel, including a human (alpha)$_{1F}$-subunit, a murine (alpha)$_{1F}$-subunit and orthologues of the human and murine (alpha)$_{1F}$-subunits.

In one embodiment, the invention comprises a DNA molecule that encodes a human retinal (alpha)$_{1F}$-subunit and has a sequence of nucleotides selected from a group consisting of:
  (a) the sequence set forth in SEQ ID NO. 1;
  (b) a sequence of nucleotides that encodes the sequence of amino acids set forth in SEQ ID NO 2;
  (c) the sequence set forth in SEQ ID NO. 3; or
  (d) a sequence of nucleotides that encodes the sequence of amino acids set forth in SEQ ID NO 4.

In another embodiment, this invention comprises a DNA molecule that encodes a murine (alpha)$_{1F}$-subunit and has a sequence of nucleotides selected from a group consisting of:
  (a) the sequence set forth in SEQ ID NO 5; or
  (b) a sequence of nucleotides that encodes the sequence of amino acids set forth in SEQ ID NO6.

In another aspect, this invention comprises a substantially pure (alpha)$_{1F}$-subunit of a mammalian retinal calcium channel, including a human (alpha)$_{1F}$-subunit represented by the sequence of amino acids set forth in SEQ ID NO. 2 or 4, a murine (alpha)$_{1F}$-subunit represented by the sequence of amino acids set forth in SEQ ID NO. 6, and orthologues of the human and murine (alpha)$_{1F}$-subunits.

In another aspect, this invention comprises an isolated RNA sequence that encodes an (alpha)$_{1F}$-subunit of a mammalian retinal calcium channel or an antisense RNA molecule having a sequence that is complementary to the mRNA encoding an (alpha)$_{1F}$-subunit of a mammalian retinal calcium channel.

In another aspect, this invention comprises an expression vector, preferably a mammalian expression vector, comprising the nucleotide sequence of an (alpha)$_{1F}$-subunit of a mammalian retinal calcium channel.

In another aspect, this invention is a cell, preferably a eukaryotic cell, comprising a heterologous DNA comprising a nucleotide sequence of (alpha)$_{1F}$-subunit of a mammalian retinal calcium channel.

In another aspect, this invention comprises an isolated nucleic acid that encodes a full-length (alpha)$_{1F}$-subunit of a mammalian retinal calcium channel, wherein the nucleic acid molecule is fully complementary to nucleic acid which is native to a mammalian retinal cell.

In another aspect, the invention comprises a method of diagnosing incomplete CSNB which method includes screening for alterations in the sequence of nucleotides disclosed herein.

BRIEF DESCRIPTION OF THE FIGURES

FIG. 2: PCR primers (SEQ ID NO:29 to SEQ ID NO:50) used to determine the nucleotide sequence of human CACNA1F, by amplifying retina cDNA and sequencing it.

Figure 4B:
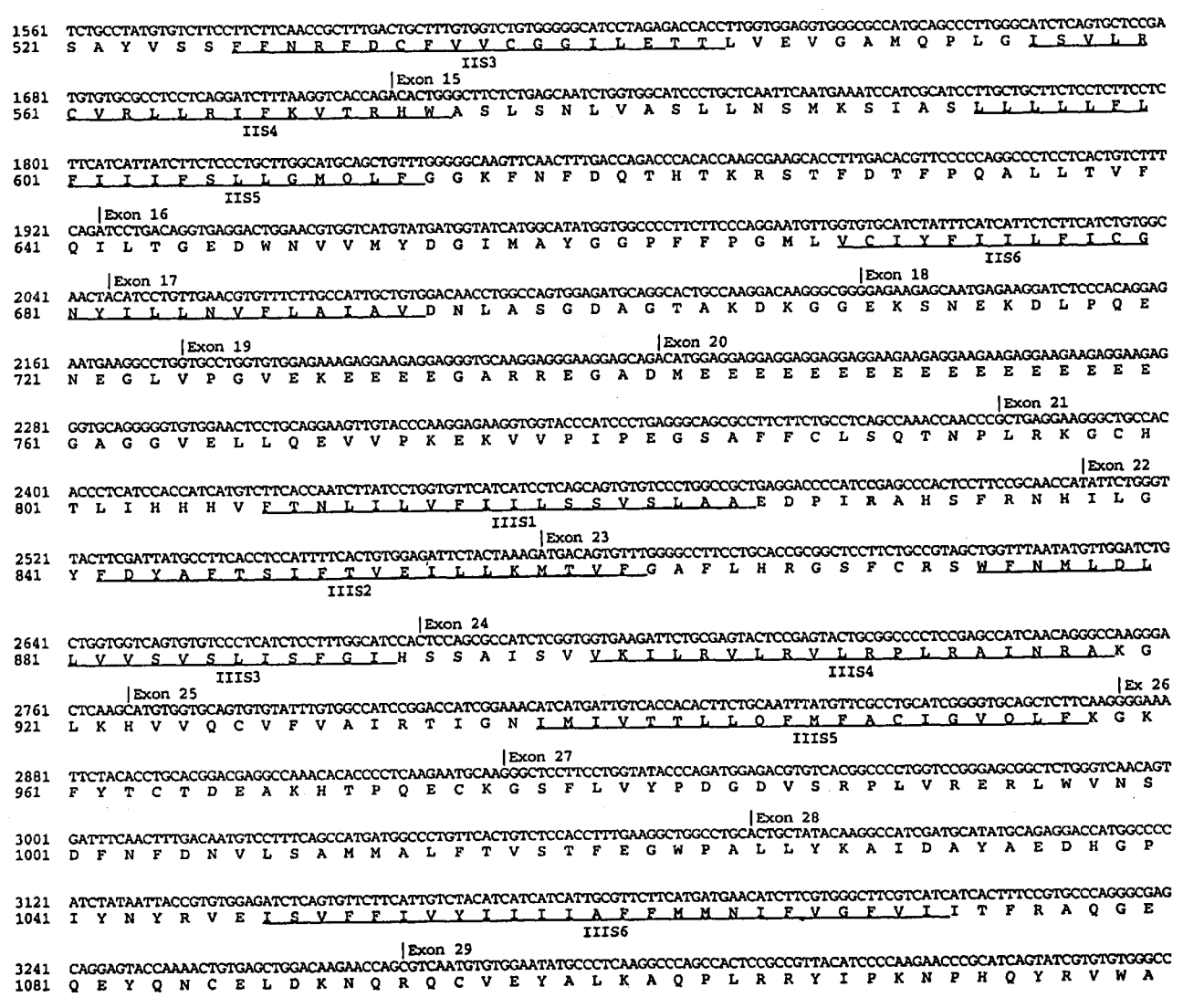
Figure 4C:
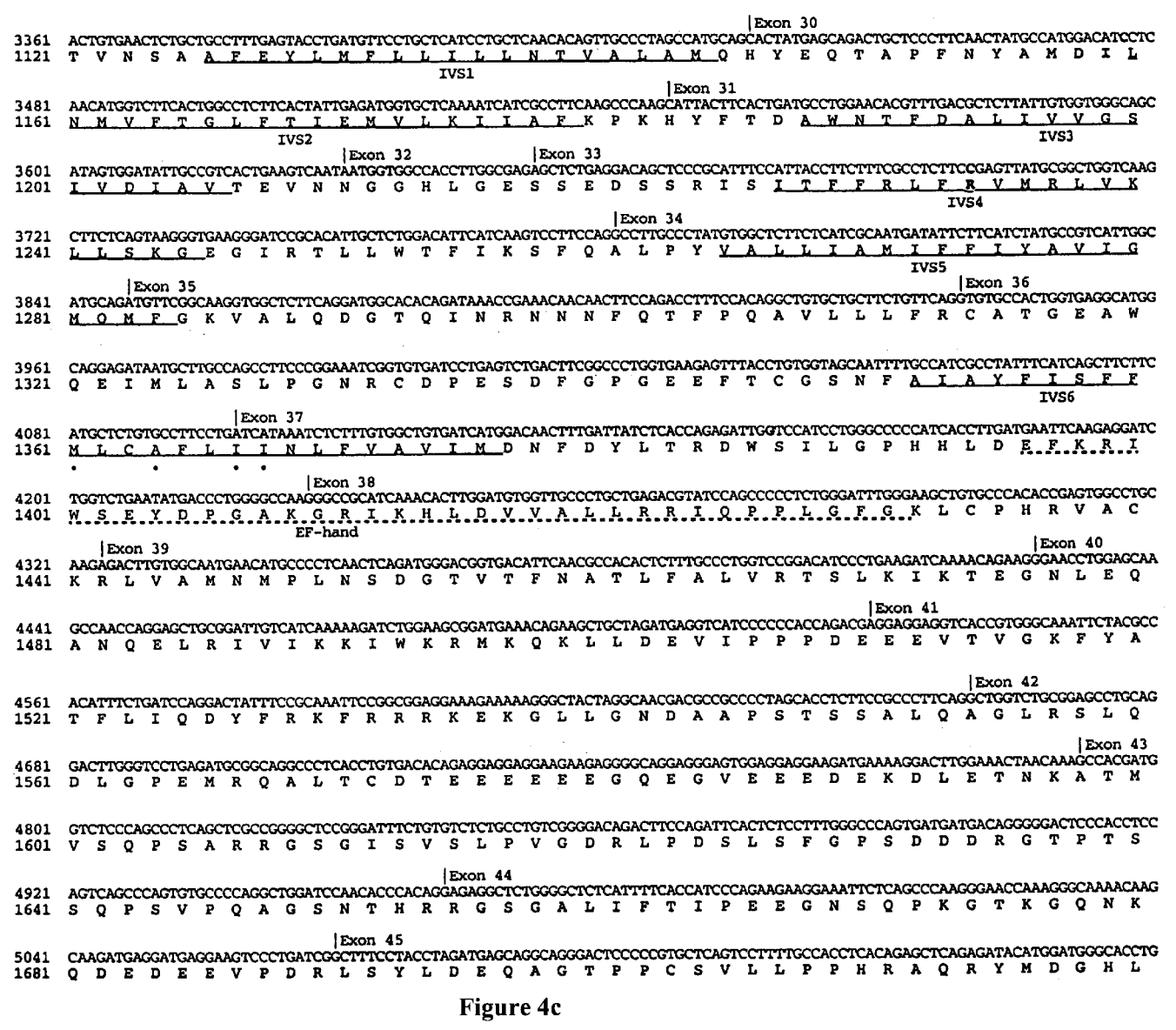

FIGS. 4A to 4D: The nucleotide sequence of a splice variant of human CACNA1F (SEQ ID NO:1). The amino acid sequence of this splice variant is indicated underneath in single letter code. (SEQ ID NO: 2). Short vertical lines show the position of exon boundaries. Predicted transmembrane segments are underlined and identified by domain and segment.

Figure 5A:
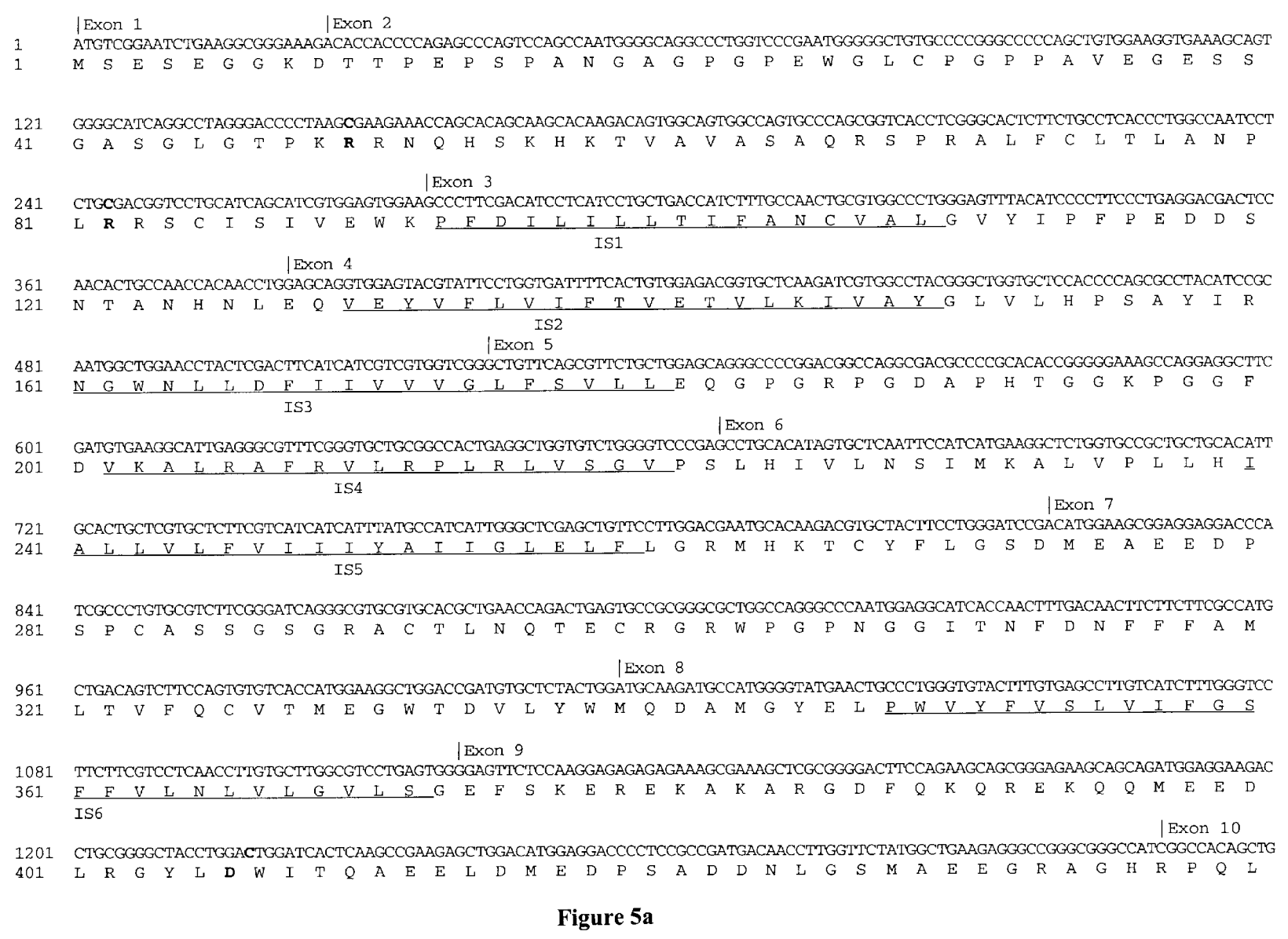
Figure 5B:
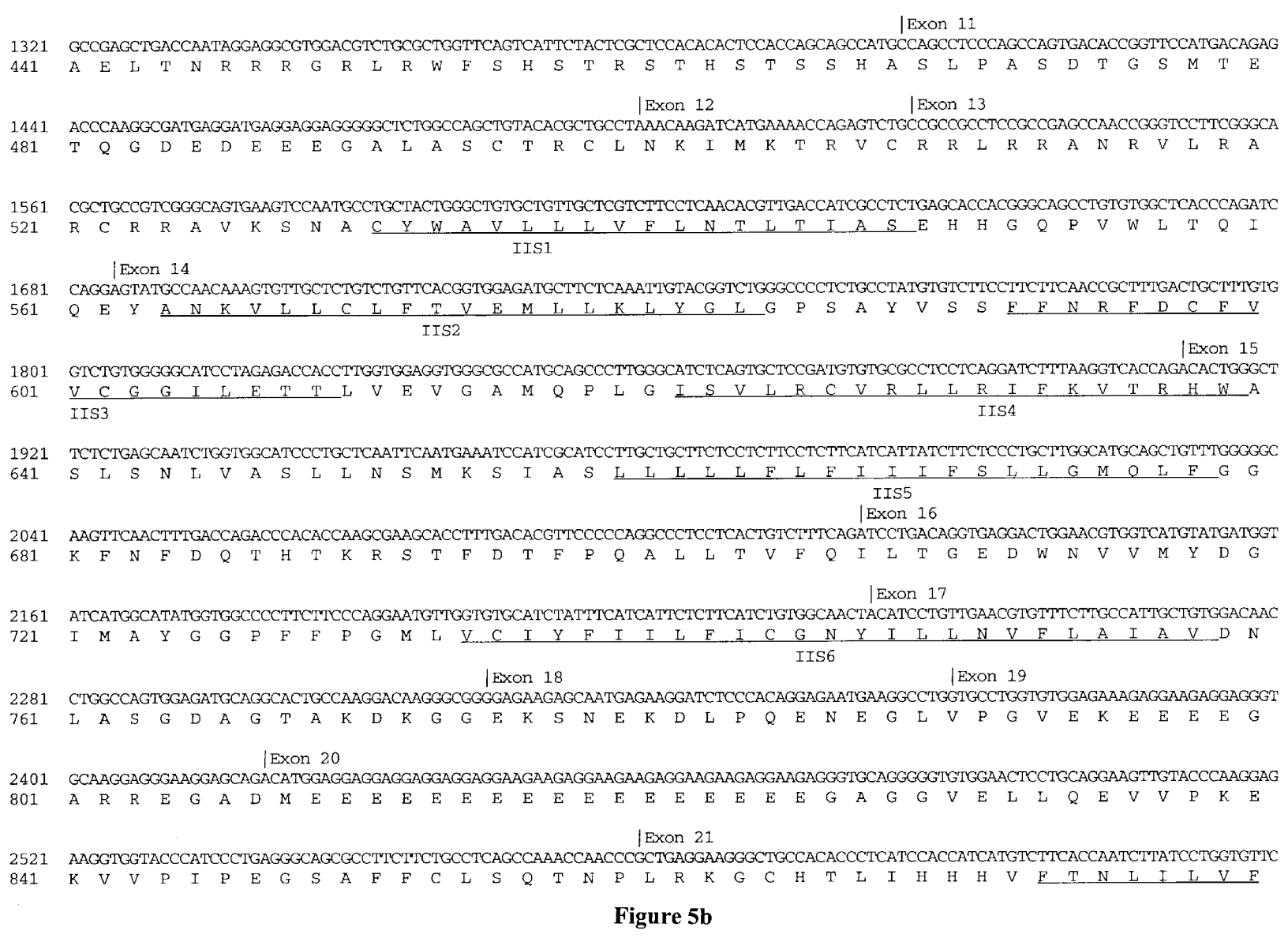
Figure 5C:
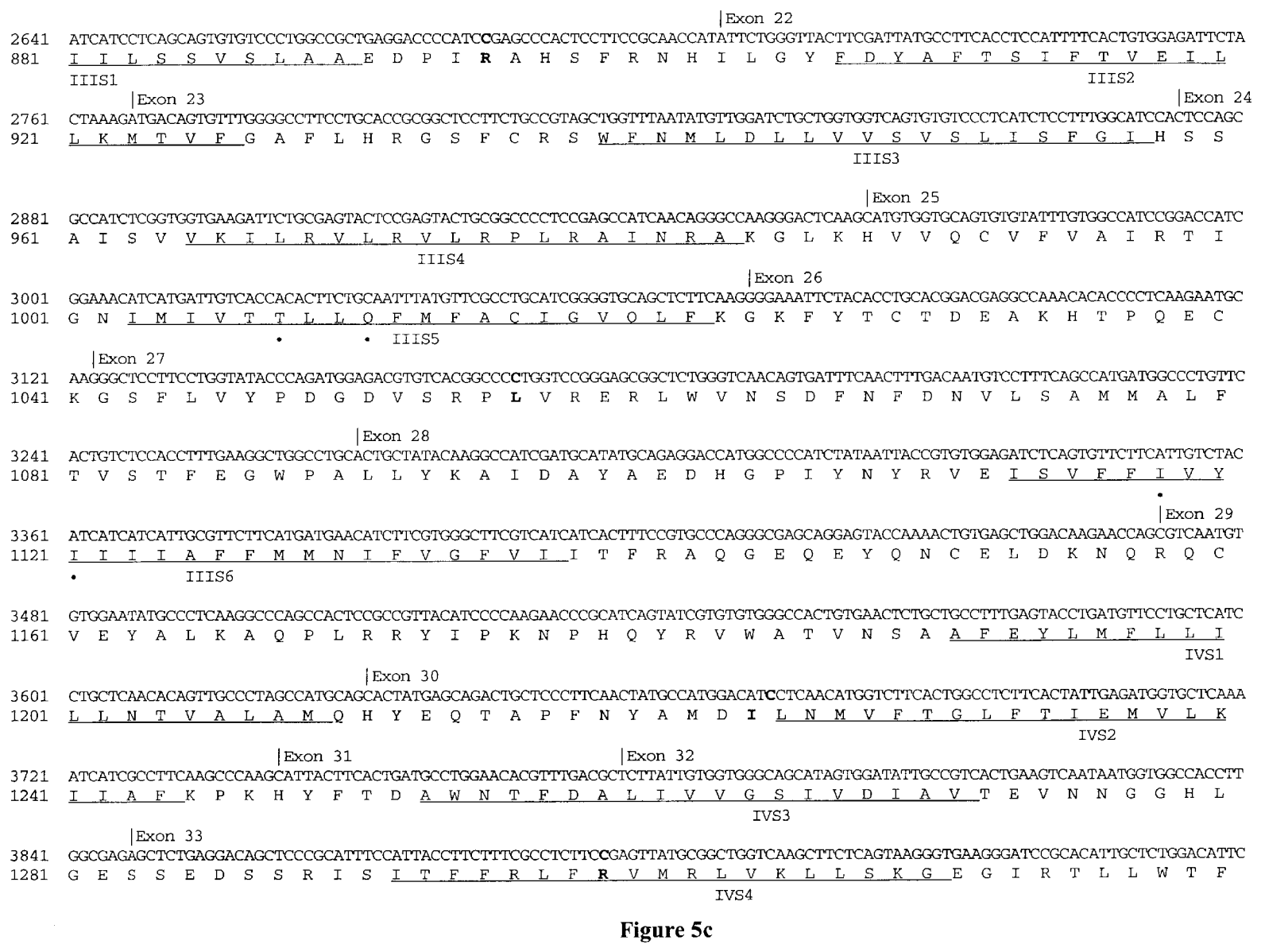
Figure 5D:
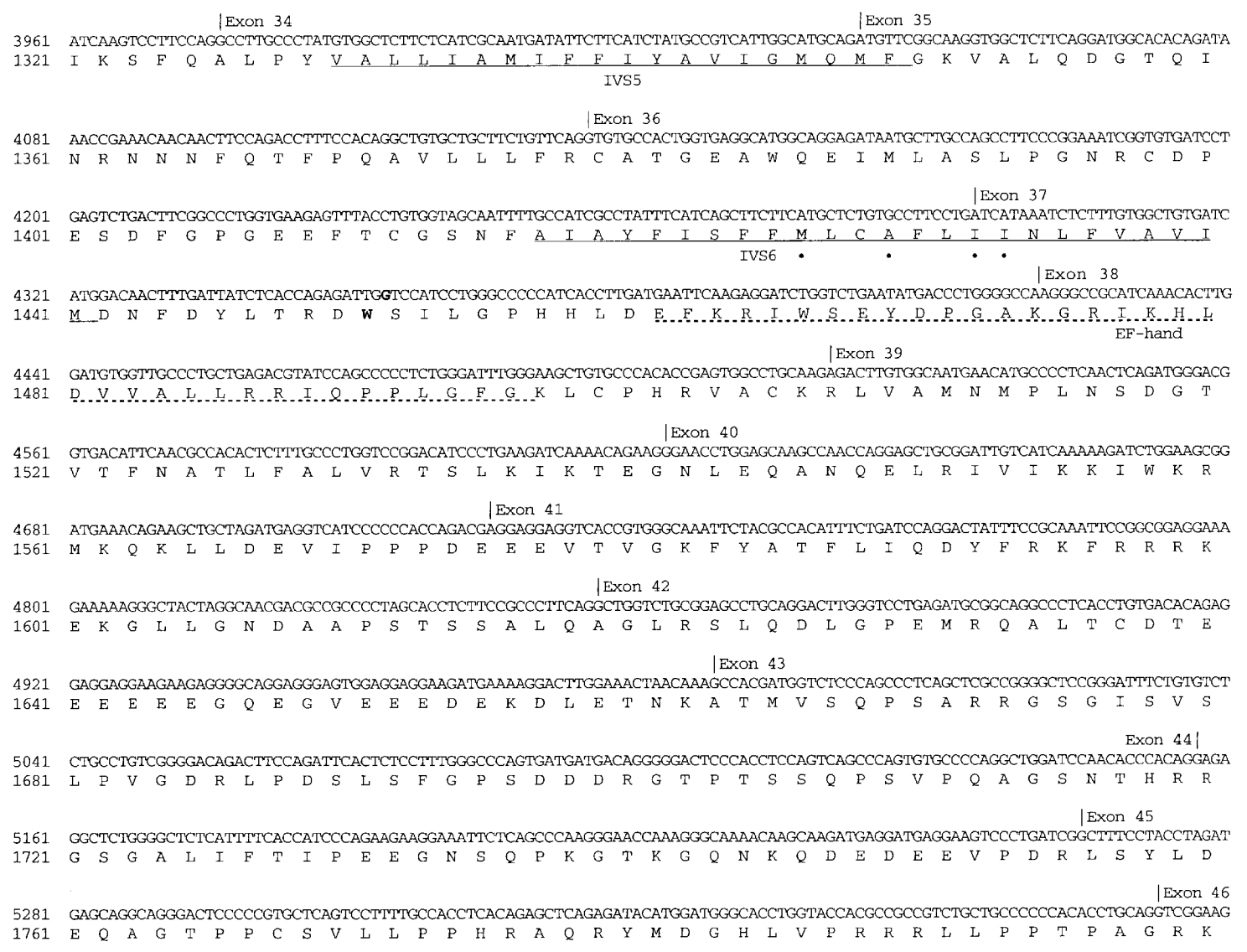

FIGS. 5A to 5D: The nucleotide sequence of a longer splice variant of human CACNA1 F (SEQ ID NO: 3). The amino acid sequence of this splice variant is indicated underneath in single letter code. (SEQ ID NO: 4). Short vertical lines show the position of exon boundaries. Predicted transmembrane segments are underlined.

FIGS. 6A–6B: CACNA1F exon specific PCR primers (SEQ ID NO. 5 to SEQ ID NO. 138) that may be used for mutation analysis in humans.

FIG. 8—Summary of the 17 mutations of CACNA1F detected in 35 families with incomplete CSNB or AIED. NS. nonsense; Del, deletion; Ins, insertion; MS, missense, simple or complex; LOF, loss of function; SS, splice site; AS, acceptor site; DS donor site. The numbers indicate the position of the mutation in the splice variant represented in SEQ ID NO: 3. Families diagnosed with AIED are indicated with an "e".

FIGS. 9A to 9F: The nucleotide sequence of murine CACNA1F (SEQ ID NO:5).

FIGS. 10A to 10B: The amino acid sequence of murine CACNA1F (SEQ ID NO: 6).

FIGS. 11A to 11H: Comparison of the nucleotide sequence of human and murine CACNA1F.

DETAILED DESCRIPTION OF THE INVENTION

Figure 1:
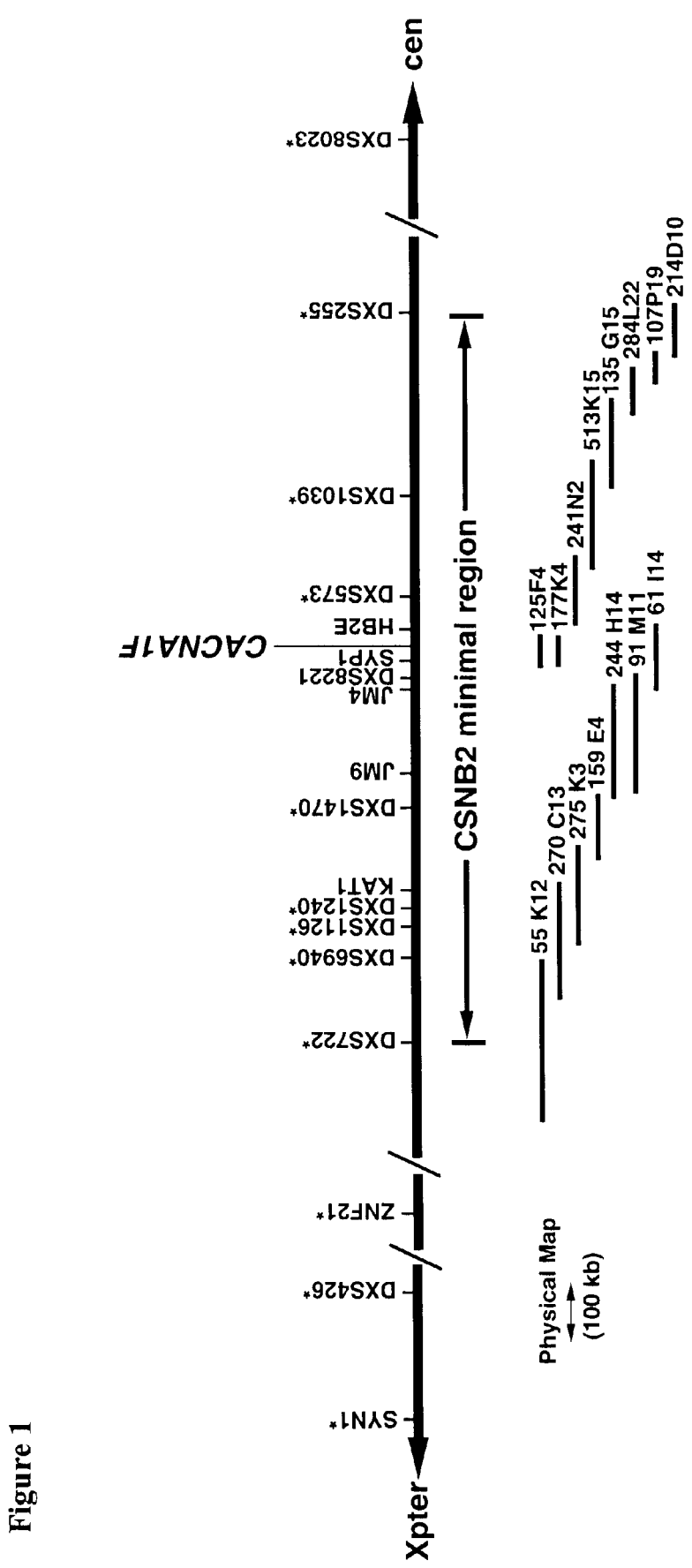
FIG. 1: Physical map of the minimal genetic region of CSNB2 in Xp11.23. The chromosomal region is indicated by the thick black line. The horizontal double-headed arrow indicates the minimal genetic region established for the CSNB2 gene. Genetic markers are indicated along the chromosome with an asterisk. Genes evaluated as candidates for CSNB2 are indicated along the chromosome (no asterisk).

The details of the preferred embodiments of the present invention are set forth in the accompanying drawings and description below. Based on the details of the invention described herein, numerous additional innovations and changes will become obvious to one skilled in art.

A. Definitions

Unless otherwise indicated, all terms used herein have the same meaning as is commonly understood by one skilled in the art of the present invention. Practitioners are particularly directed to *Current Protocols in Molecular Biology* (Ausubel) for terms of the art.

As used herein the following terms have the following meanings:

"(alpha)$_{1F}$-subunit" refers to a protein with an amino acid sequence equivalent to that depicted in FIGS. 4, 5 or 10, or in SEQ ID NOs. 2, 4 or 6 and includes a protein that is fully functional; a protein that has minor changes in amino acid sequence, such as conservative amino acid substitutions that do not affect activity; a protein resulting from the translation of a splice variant, and a protein that has a minor change in amino acid sequence which affects the function of the protein. Of particular importance, "(alpha)$_{1F}$-subunit" includes a protein which contains an amino acid change that is identified in the mutational analysis and which results in incomplete CSNB or a similar disorder designated by another name.

"CACNA1F" unless indicated otherwise, "CACNA1F" refers to human CACNA1F, murine CACNA1F or an orthologue thereof. The term "CSNB2" may also refer to CACNA1F, in the appropriate context.

"carrier" refers to a female who does not have the phenotype associated with incomplete CSNB, but one of whose copies of the gene causing incomplete CSNB has a mutation in it that may cause incomplete CSNB.

"DNA or RNA encoding an (alpha)$_{1F}$-subunit" includes any DNA or RNA which would encode a protein that is an "(alpha)$_{1F}$-subunit" as defined above.

"expression" refers to transcription of a DNA sequence into RNA, and includes transcription which would result in an antisense RNA. Expression also refers to translation of a RNA sequence into a protein.

"expression vector" refers to a recombinant DNA construct that comprises, among other elements, a DNA sequence of which expression is desired. An "expression vector" is used to introduce heterologous DNA into cells for expression of the heterologous DNA, as either an episomal element, or after incorporation into the cellular genome. An "expression vector" will contain all of the elements necessary for transcription of the DNA sequence functionally linked to the DNA sequence, including but not limited to, a transcription initiation element, a transcription termination element and elements that modulate expression of the DNA sequence, such as promoters or enhancers. These elements may be native to the DNA sequence of which expression is desired. An expression vector may contain elements that will regulate translation if translation of the resultant RNA transcript into a protein product is desired.

"functional" with respect to an $(alpha)_{1F}$-subunit of a retinal calcium channel refers to the ability of an $(alpha)_{1F}$-subunit of a retinal calcium channel, or a calcium channel comprising an $(alpha)_{1F}$-subunit, to provide for and regulate passage of calcium channel selective ions (e.g. $Ca^{2++}$ or $Ba^{2++}$). A fully functional $(alpha)_{1F}$-subunit of a retinal calcium channel refers to an $(alpha)_{1F}$-subunit of a retinal calcium channel, or a calcium channel comprising an $(alpha)_{1F}$-subunit which is able to provide for and regulate entry of calcium channel selective ions at the level of a wild type $(alpha)_{1F}$-subunit of a retinal calcium channel.

"heterologous" refers to DNA or RNA that does not occur naturally as part of the genome in which it is present, which is found in a location or locations in the genome that differ from that in which it occurs in nature, or which is present in the genome as a result of human manipulation of the genome. It is DNA or RNA that is not endogenous to the cell in which it is found, or that is endogenous to the cell but which has been manipulated in vitro, and has been artificially introduced into the cell. Heterologous DNA or RNA need not be incorporated into the host cell genome, but may be maintained episomally Examples of heterologous DNA include, but are not limited to, DNA that encodes a calcium channel $(alpha)_{1F}$-subunit and DNA that encodes RNA or proteins that mediate or alter expression of endogenous DNA by affecting transcription, translation or other regulatable biochemical processes.

"high stringency" or "conditions of high stringency" means washing at low salt concentration, less than about 0.2 and preferably about 0.1 SSPE, and at high temperature, more than about 60° C. and preferably about 65° C. It will be understood that an equivalent stringency may be achieved by using alternative buffers, salts and temperatures.

"incomplete CSNB" includes eye disorders such as AIED or AIED-like disorders, which are not clinically diagnosed as incomplete CSNB, but which are known or found to be caused by mutation in the CACNA1F coding region.

"orthologue" refers to a gene from another mammalian species that is that species' equivalent to the nucleotide sequence presented in SEQ ID NO:1, SEQ ID NO:3 or SEQ ID NO: 5.

"precursor" refers to a protein with the amino acid sequence corresponding to the sequence of the full length mRNA which, upon translation, results in a protein which may be further processed to form the $(alpha)_{1F}$-subunit of a retinal calcium channel.

"splice variant" refers to a variant produced by differential processing of a primary transcript of genomic DNA that results in more than one type of mRNA. Splice variants may occur within or between tissue types. Thus, cDNA clones that encode proteins with different amino acid sequences are "splice variants".

"substantially pure" refers to a subunit, protein or polypeptide that is sufficiently free of other polypeptide contaminants to be considered homogeneous by SDS-PAGE or to be unambiguously sequenced.

B. Mapping the Location of the Gene for Incomplete CSNB 32 families with CSNB, 11 with complete and 21 with incomplete CSNB, were characterized to identify recombination events that would refine the location of the disease gene(s). The methodology used to localize genes on human chromosomes using these and other techniques is well known to those skilled in the art.

Critical recombination events in the set of families with complete CSNB localized the disease gene to the region between DXS556 and DXS8083 in Xp11.4-p11.3. Critical recombination events in the set of families with incomplete CSNB localized the disease gene to the region between DXS722 and DXS8023 in Xp11.23 [4] (FIG. 1). FIG. 1 also indicates, as overlapping bars that lie underneath the minimal region, the name and approximate position of the BAC's that encompass the entire minimal region.

Further analysis of the families with incomplete CSNB by disease-associated haplotype construction identified 17 families of apparent Mennonite ancestry who share portions of an ancestral chromosome which refined the location of the gene for incomplete CSNB to the region between DXS722 and DXS255, a distance of approximately 1.2 Mb (FIG. 1).

C. Characterization of the Gene Encoding CACNA1F

Candidates for the CSNB2 gene were expected to be expressed in the retina and located in the CSNB2 minimal region (see FIG. 1). Five genes (KAT1, SYP1, HB2E, JM4, and JM9) that met these criteria were screened, but no mutations of these genes were found in affected males from the incomplete CSNB families studied.

Figure 3:
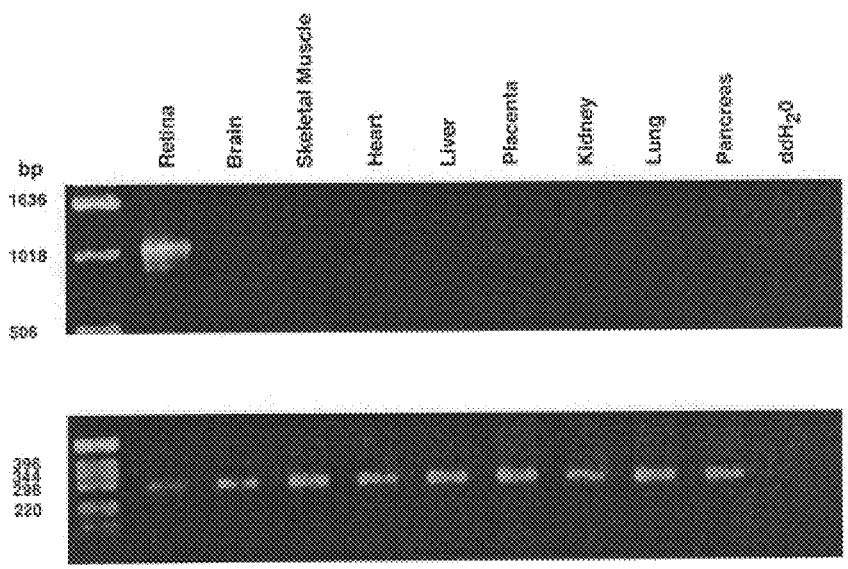
FIG. 3: cDNA expression profile in various human tissues, UPPER PANEL: CACNA1F, a 1060 bp PCR product encompassing most of exons 24–33; LOWER PANEL: ubiquitously expressed EST, JRL4A1, a 281 bp PCR product.

The expression pattern of the putative gene, CACNA1F, with homology to $(alpha)_1$-subunits of calcium channels was analysed. Nine man tissue-specific cDNA libraries (QUICK-Screen™ Human cDNA Library Panel, Clonetech) were analyzed by PCR, using primer pairs from exons 24 and 33 (FIG. 2). PCR products were electrophoresed on an agarose gel and visualized by ethidium bromide staining. The 1,060 bp PCR product was detected only in the retinal cDNA library (FIG. 3a). In contrast, the ubiquitously expressed EST (expressed sequence tag) JRL4A1, amplified by primers For-TTTCTCTCTGTCTACCTTGT (SEQ ID NO: 7) and Rev-CTGCGGGCTCCCTTACTACTG (SEQ ID NO: 8), was detected in all of the cDNA libraries as a 281 bp fragment (FIG. 3b). These results demonstrated that CACNA1F is expressed in the retina, and suggest that its expression in other tissues is unlikely.

Computer predictions as to where the introns and exons of this gene lie allowed for the design of oligonucleotides that would function as PCR primers for use with cDNA. Primers were designed by using the Primer3™ program. A list of preferred oligonucleotide PCR primers suitable for such a purpose is provided in FIG. 2.

Total human retinal RNA was transcribed into cDNA, which was then subjected to PCR analysis using the above mentioned primers. After amplification, PCR products were prepared for sequencing by agarose gel electrophoresis and purification with Qiaquick™ (Quiagen). Sequencing reactions were performed with Thermosequenase ™ and products were visualised by autoradiography after polyacrylamide gel electrophoresis. These methods are well known to those skilled in the art.

The PCR and sequencing analysis described above demonstrated that CACNA1F consists of 48 exons and encodes splice variants, one of which is a protein of 1912 amino acids (FIG. 4). Several other splice variant forms were identified by PCR analysis. Therefore, isoforms of varying amino acid lengths are expected. Alternative splicing is a feature commonly seen in the calcium channel $(alpha)_1$-subunit genes as a mechanism for forming distinct channels [5] and may be the basis for cell-specific $(alpha)_1$-subunit expression.

$(Alpha)_1$-subunits of L-type calcium channels are pore-forming proteins with cytoplasmic amino and carboxyl termini separated by four homologous domains (I–IV), each consisting of six transmembrane segments (S1–S6). CACNA1F shares these features of calcium channel (alpha)$_1$-subunits of L-type channels (see FIGS. 4 and 5). CACNA1F is most similar to the L-type C, D and S members of the voltage-gated calcium channel (alpha)$_1$-subunit gene family. In particular, CACNA1F appears to have diverged most recently from the human (alpha)$_{1D}$-subunit gene (CACNA1D), which is expressed in the brain [16]. The similarity between the human (alpha)$_{1D}$-subunit gene and CACNA1F was 70% overall and 84% between transmembrane segments. Of the five amino acids in the IVS6 transmembrane domain that are critical for conferring dihydropyridine sensitivity, four are present in the predicted CACNA1F amino acid sequences, depicted in FIGS. 4 and 5, and identified as SEQ ID NO.'s: 2 and 4.

It is understood that the amino acid sequences of CACNA1F disclosed herein may be modified by making minor variations in sequence, such as conservative amino acid substitutions or minor deletions or insertions that do not alter the activity of the subunit, and the resulting modified subunits are contemplated herein. Suitable conservative substitutions of amino acids are known to those of skill in this art, and may be made generally without altering the biological activity of the resulting molecule. Such substitutions may also be made empirically.

D. Mutation and Segregation Analysis of the Coding Region of CACNA1F

To identify which mutations in CACNA1F cause incomplete CSNB, exons of the CACNA1F gene in patients with incomplete CSNB were analyzed by direct DNA sequencing using intron-based exon-specific PCR primer pairs. In this type of analysis, PCR primers that will bind with intron sequences on either side of the exon(s) of interest are designed. Primers are ideally positioned 20–50 bp from the splice site, and will amplify one or more exons. All primer pairs were confirmed to be region-specific by PCR amplification of a panel of conventional and radiation-induced somatic cell hybrids, as described in [14]. Primers suitable for such a purpose were designed by using the Primer3™ program and are provided in FIG. 6. After exon(s) in genomic DNA are amplified by the intron-specific primers, the DNA is purified and sequenced, as described in section B above, for the CACNA1F gene analysis. All of these methods are well known to those skilled in the art.

Once a nucleotide change is identified by the sequencing analysis, segregation analysis may be accomplished by allele sizing as described in [14] and demonstrated in FIG. 7a. PCR is used to amplify the region of interest from genomic DNA of affected, non-affected and carrier individuals. The radioactively-labelled PCR products are electrophoresed through polyacrylamide gels which can distinguish between as little as a single base pair insertion or deletion.

Alternatively, segregation analysis may be accomplished by following the loss or gain of restriction sites, as demonstrated in FIG. 7b. Mutated and wild-type sequences are compared by a DNA analysis program, for example DNA Strider1.2™, looking for changes in sequence that would result in a loss or gain of a restriction site. Once found, these changes can be used to track the mutation in families of affected individuals. Firstly, PCR is used to amplify the interest from genomic DNA of affected, non-affected and carrier individuals. The PCR products are digested with the enzyme that will detect the mutation (in either a positive or negative sense). The digested products are electrophoresed through agarose and visualized to determine whether the restriction enzyme site is present or not, whichever the case may be, in the individual analysed.

Numerous additional methods for identifying mutations of the CACNA1F coding region in individuals, or tracing mutations of the CACNA1F gene through families, including but not limited to SSC and heteroduplex analysis, are obvious to one skilled in the art.

In the present invention, 31 families with incomplete CSNB were studied. Of these families, 17 shared part of a common Mennonite haplotype (families 21, 50, 70, 60, 60B, 80, 130, 150, 160, 170, 180, 190, 200, 240, 250, 330, and 340), and three did not (families 100, 140, and 520). Using intron-based exon-specific PCR primer pairs (FIG. 6), a total of 17 sequence changes were discovered in all families analyzed (FIG. 8), all of which segregated in their respective families to affected males, through carrier females. None of these were observed in 100 control chromosomes, indicating that these sequence changes are not polymorphic alterations of CACNA1F in the Caucasian population. However, there were several additional mutations detected in the CACNA1F gene which were determined to represent polymorphisms in the Caucasian population.

As well, four families with AIED were studied. Using intron-based exon-specific PCR primer pairs, a total of four sequence changes were discovered in the CACNA1F gene in these families (FIG. 8) (all of which segregated in their respective families to affected males, through carrier females). None were observed in 100 control chromosomes, indicating that these sequence changes are not polymorphic alterations of CACNA1F in the Caucasian population.

Fifteen families with common Mennonite haplotype were found to segregate the same frameshift mutation in CACNA1F, called L1056insC (FIG. 7a, FIG. 8). Segregation analysis of this mutation was performed by allele sizing of exon 27, as demonstrated in FIG. 7a. In one of these families (family 60), three females who manifest with incomplete CSNB and who were previously suggested by haplotype analysis to be homozygous for the "Mennonite" mutation showed only the L1056insC mutation and no normal allele (FIG. 7a). The other two families which previously were found to have the common Mennonite haplotype (families 21 and 70) showed different frameshift mutations (I1224delC and D406delC, respectively) (FIG. 8). In other families with incomplete CSNB (families 100, 140, and 520), unique nonsense mutations in CACNA1F were seen (R1299X; W1451X, and R895X, respectively) (FIG. 8). Two loss of function mutations are caused by different mutations in splice acceptor sites (Exon27AS and Exon41AS, FIG. 8).

In addition, six missense mutations in CACNA1F, each of which cause incomplete CSNB or AIED, have been detected. Missense mutations, which are only a minor variation in the sequence of a protein, yet which cause these disorders, are presumed to represent amino acids that have a very important role in the function of the CACNA1F protein.

Our identification of 11 different mutations of CACNA1F in families with incomplete CSNB or AIED, which would cause premature stop codons and therefore truncated translation products, strongly argues that mutations in CACNA1F cause these disorders. Further, the occurrence of the L1056insC mutation in fifteen families with the common Mennonite haplotype supports the suggestion that these families are related by a founder mutation. Consequently, it is likely that the L1056insC "Mennonite" mutation will be observed in other descendants of Mennonite immigrants who came to Western Canada in the last century, and among descendants of their Russian and European forefathers in other parts of the world. Of note, families 21 and 70 that share part of the Mennonite haplotype show different frameshift mutations.

E. Possible Consequences of CACNA1F Mutations

The 17 mutations identified in our 35 families with incomplete CSNB or AIED are distributed across CACNA1F coding region. Mutations that would result in a truncated protein are predicted to result in a loss of function. Additional characterization of the truncated proteins may reveal the specific consequences of each mutation.

Missense mutations are predicted to disrupt specific functions of the intact CACNA1F and therefore are much more informative as to the structure-function relationship of intact CACNA1F in the calcium channel.

F. Construction of Full-Length cDNA Clones

Full length cDNA clones may be constructed by a plurality of methods known to those skilled in the art. Such methods include screening a cDNA library with a labeled DNA probe of the gene of interest, identifying overlapping cDNA clones and ligating them together into one clone that contains the entire coding region. One may also obtain a full length cDNA clone in one step from a library, obviating the need to perform intermediary ligation steps. If the 5' or 3' end only of the clone is missing, methods such as RACE (rapid amplification of cDNA ends) may be used to complete the sequence, or if the full length sequence is known, PCR amplification and ligation of the fragments onto the ends of the cDNA clone may be used.

Alternatively, in another well-known method, one may use PCR to amplify regions of a gene of interest from a cDNA library or a cDNA preparation, and subsequently ligate the PCR products together into one clone that contains the entire coding region. Using this method, one skilled in the art may select from a variety of cloning vectors, including high and low copy number plasmids, such as pBluescript or pBR322 or phage and one may also select from a variety of bacterial hosts. Rather than ligating smaller PCR fragments together, it is also possible to PCR an entire cDNA sequence using a Taq Polymerase that is designed for long range PCR, such as pfu™ or Vent™ Polymerase, and then ligate that entire fragment into a suitable vector.

For ligation of PCR fragments together to create a full length cDNA clone, primer sets are designed to yield overlapping PCR fragments of manageable size, which will, when combined, represent the entire full-length cDNA. The primers are also designed such that the PCR fragments which are amplified will contain restriction sites that are unique to the cDNA and the vector in which the fragment is to be inserted. A preferred vector is PCR2.1-TOPO™ (Invitrogen). The forward primer for the most 5' fragment is designed to contain a small ribosomal binding site. The forward primer for the most 5' fragment and the reverse primer for the most 3' fragment (the extreme 5' and 3' ends, respectively) also contain recognition sites for extremely rare cutting restriction endonucleases, such as NotI.

First strand cDNA can be amplified with or without DNA polymerase of high fidelity such as Turbo Pfu™ (Strategene). PCR products are verified by DNA sequencing and restriction digestion, to ensure that they are identical in sequence to the native cDNA. Fragments are then ligated together into one complete transcription unit and again checked for accuracy by restriction analysis. A person skilled in the art may modify these methods as necessary, depending upon the exigencies presented in each particular step of the assembly.

G. Preparation of Cells Containing a Recombinant DNA Encoding an (Alpha)$_{1F}$-subunit DNA encoding an (alpha)$_{1F}$-subunit, or a portion thereof, may be introduced into a host cell for expression of the DNA using methods well known to those skilled in the art. Such methods include for example, preparation of a suitable expression vector, introduction of the expression vector into suitable cells and selection of transfected cells.

Practice of the present invention can be effectively carried out using any of a number of expression vectors. A person skilled in the art may choose the vector that is appropriate, depending upon, among other factors, the cell type and the type of expression desired. For instance, vectors include, but are not limited to, those that constitutively express a DNA sequence at high or low levels, or those that inducibly express a DNA sequence at high or low levels. Particularly preferred vectors for transfection of mammalian cells are pSV2dhfr expression vectors, and for prokaryotic cells, pBluescript™ vectors (Stratagene) or pBR322 vectors.

Practice of the present invention can be effectively carried out using any of a number of different cell types, eukaryotic or prokaryotic. A person skilled in the art will choose the cell line that is appropriate, depending upon the desired application. For example, if a large amount of substantially pure protein product is desired, a prokaryotic or yeast cell may be selected. If functional calcium channel activity is the desired objective, a mammalian cell may be selected, and depending upon the desired application, the mammalian cell may lack endogenous calcium channel activity, or may contain additional different expression vectors that encode other components of a calcium channel. One skilled in the art may choose an expression vector that will either integrate, or not integrate, into the chromosomal DNA of the cell. Preferred mammalian cells include COS cells. CHO cells, HEK cells or mouse L cells. Preferred prokaryotic cells include strains of *Escherichia coli* such as DH1α or JM109. Yeast cells such as *Saccaharomyces cerevisiae* may also be utilized.

Introduction of the expression vector into cells may be accomplished by transfection, using techniques that include calcium phosphate precipitation, electroporation or injection. A person skilled in the art will choose the method that is appropriate. The preferred method of transfecting DNA is by electroporation. The method of selection for transfected cells will depend upon the selectable marker chosen, and may include the gene for thymidine kinase or neomycin resistance in mammalian cells, and ampicillin or kanamycin resistance in prokaryotic cells.

Mammalian expression systems are particularly preferred for practicing certain aspects of this invention.

It is also within the contemplation of this embodiment that recombinant cells containing DNA encoding an (alpha)$_{1F}$-subunit may be prepared by means that do not include the use of an expression vector. This would be the case for instance, if the preparation of the recombinant cell containing DNA encoding an (alpha)$_{1F}$-subunit was for the purpose of replication of the DNA sequences themselves, as might occur if the DNA to be used in section I, below or if the DNA was to be used in intermediate steps of in vitro gene manipulation.

It is also within the contemplation of this embodiment that cells containing a recombinant expression vector comprising a gene for an (alpha)$_{1F}$-subunit may be prepared for the purpose of expressing an antisense RNA transcript of CACNA1F or a part thereof within the cell. To accomplish this, the CACNA1F insert may be ligated into the expression vector in reverse orientation, such that transcription from a promoter will result in an RNA transcript that is complementary to the mRNA in the cell.

In another embodiment, vectors that are designed to allow for integration of the DNA sequence into the genome of an organism, rather than expression of the DNA sequence, may be used to introduce the DNA sequence into the recombinant cell. Such vectors would include, for instance, phage vectors that are used in transgenic mouse technology.

H. Preparation of Cells Containing the Protein Product of CACNA1F

In most instances, the cells prepared intra section H, above, will be designed to express the protein product of CACNA1F, an (alpha)$_{1F}$-subunit. This would occur via transcription of the heterologous CACNA1F sequences after introduction into the cell.

It may be desired to express an (alpha)$_{1F}$-subunit in a cell without utilizing the intervening steps of introducing the DNA encoding an (alpha)$_{1F}$-subunit into the cell. A plasmid, such as pBluescript™, containing the DNA encoding an (alpha)$_{1F}$-subunit, or a part thereof, may be transcribed in vitro with an RNA polymerases, such as T7 RNA polymerase, to produce an abundant RNA transcript that is easily isolated. This RNA transcript is designed to include the appropriate signals for translation, including translation initiation and termination sites. When injected into cells such as oocytes from *Xenopus laevis,* the RNA is translated into the protein for which it encodes. Additional RNA transcripts, encoding other subunits of calcium channels may also be injected into the same oocyte if it is desired to create functional heterologous calcium channels in the oocyte.

Methods for in vitro transcription and injection of the resulting RNA into eukaryotic cells are well known in the art. Amphibian oocytes are particularly preferred for this aspect of the invention.

H. Identification of CACNA1F Orthologues in Other Mammalian Species cDNA's representing several mouse tissues were amplified by PCR with the primers indicated in FIG. 2, used for the human CACNA1F. The amplified PCR fragments were sequenced and compared to the human CACNA1F sequence.

Primer sets for exons 6–10, 10–15, 20–28, 24–32 and 35–38 yielded PCR products from murine retina cDNA which were approximately the same size as the human PCR products with the same primer sets. Murine CACNA1F was expected to be highly homologous to the human CACNA1F, therefore the size of the PCR fragment generated in the mouse cDNA was likewise expected to be similar to the human CACNA1F.

In other instances, more than one PCR product for a particular primer pair was observed, or the band that was amplified was not the expected size. Where primer pairs would amplify overlapping segments (i.e. 6–10 and 10–15 would both amplify region 10), then sequences of the two PCR fragments were compared and if they were identical, both fragments were presumed to come from the murine CACNA1F gene. If they were not identical, then it was presumed that the PCR fragment with higher homology to human CACNA1F contained murine CACNA1F sequence and the other fragment did not. These strategies yielded more than 1/2 of the murine CACNA1F sequence.

To obtain the much of the remainder of the murine CACNA1F sequence, three mouse specific primers sets, covering exons 15–21, 32/33–38 and 38–42 were designed from the mouse sequence that was known at that point. The sequence of these primers is provided in Example 4, below. These primers were used to amplify the additional regions of murine CACNA1F.

There was some difficulty amplifying exons 3 to 10 of the murine CACNA1F sequence. To circumvent this, amplification was performed by using a human-specific forward primer and a mouse-specific reverse primer, as shown in Example 4, below.

Finally, the 5' and 3' ends of the murine cDNA sequence for CACNA1F were obtained by 5' and 3' RACE, using the Marathon cDNA Amplification Kit (Clonetech). These methods are well known to those skilled in the art.

The murine CACNA1F gene was mapped to chromosome X of the mouse. Further, it is situated adjacent to the Syp gene in mouse, as the human CACNA1F gene is located beside the human SYP gene the X-chromosome. This similarity is additional evidence that these genes are orthologues of one another.

It is apparent to persons skilled in the art, that orthologues of CACNA1F may be identified in, and isolated from, other mammalian species using other methods, including screening of genomic or cDNA libraries with a labeled human or murine DNA probe. The examples and preferred embodiments outlined herein do not preclude the use of these other methods.

EXAMPLES

The following examples are intended to illustrate but not limit the invention. While they are typical of those that might be used, other procedures known to those skilled in the art may alternatively be utilized.

Example 1

Analysis of Genomic Structure

A retinal cDNA library (JNR. [15]) and retinal first strand cDNA from total mRNA, were used as templates for generation of detailed exon sequence of the computer predicted calcium channel (alpha)$_1$-subunit. PCR amplification was performed with AmpliTaq Gold™ polymerase (Perkin Elmer) in 1.5 mM MgCl$_2$ and the supplied buffer. An initial denaturation of 7 min at 94° C., was followed by 35 cycles of: denaturation at 94° C. for 30 s, annealing at 55° C. for 45 s. and extension at 72° C. for 45 s, followed by final extension for 7 min at 72° C. PCR products were isolated in 1% low melting point agarose gel and purified using a QIAquick™ gel extraction kit (Qiagen). Purified PCR fragments were then sequenced using the forward and/or reverse primer and ThermoSequenase™ radiolabeled terminator cycle sequencing (Amersham LIFE SCIENCE), electrophoresed on 6% polyacrylamide gels, and visualized by autoradiography.

Example 2

Mutation Analysis

Genomic DNA (300 ng) was amplified with AmpliTaq Gold™ polymerase (Perkin Elmer), in 1.5 mM MgCl$_2$ for all exons, with the exception of exons 13, 14 and 30, which were amplified in 1.0 mM MgCl$_2$, and exon 43, which was amplified in 0.5 mM MgCl$_2$. Cycling conditions were the same as used for the confirmation of exon/intron structure, described above. Purified PCR products from affected and control individuals were sequenced using ThermoSequenase™ radiolabeled terminator cycle sequencing (Amersham LIFE SCIENCE), electrophoresed on 6% polyacrylamide gels, and visualized by autoradiography.

Example 3

Segregation Analysis

Figure 7:
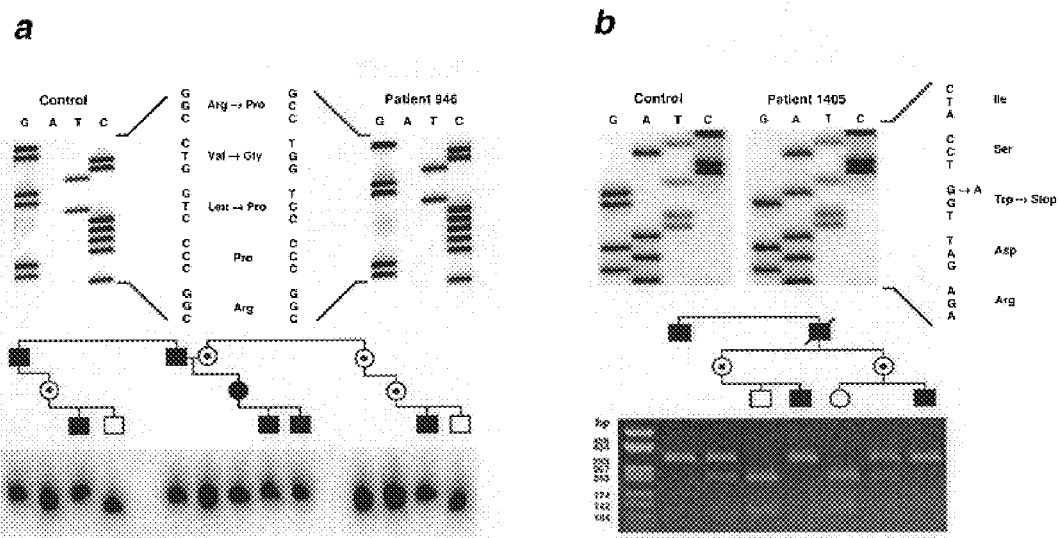
FIG. 7: Mutation analysis of the CACNA1F gene in families with incomplete CSNB. (A) Identification of a frameshift mutation caused by insertion of a C nucleotide at position 2971, in amino acid position 1056, in the splice variant depicted in FIG. 4. Segregation analysis of this mutation was performed by PCR amplification of genomic DNA and resolution of radioactively labelled PCR products by PAGE. Affected individuals and carriers have a 208 bp product while unaffected individuals have a 207 bp product. (B) Identification of a nonsense mutation caused by a G to A transition, which changes a Trp codon to a stop codon at amino acid position 1451 in exon 37, of the splice variant depicted in FIG. 5. Segregation analysis of this mutation was performed by PCR amplification of exon 37, restriction endonuclease digestion with AvaII and gel electrophoresis of the products. The G to A transition destroys the AvaII site, therefore in affected individuals and carriers the 339 bp PCR fragment is not digested with AvaII, whereas in normal individuals and carriers it is digested into 231 and 108 bp fragments.

Once a nucleotide change was identified, the loss or gain of restriction sites of the PCR fragment was analyzed using DNA Strider 1.2™. For example, the nucleotide change in exon 9 resulted in a gain of a FokI site (Normal (N)-271 bp; Mutant (M)-136 bp, 134 bp); in exon 21 the loss of a FokI site (N-94 bp, 77 bp, 42 bp, 36 bp, M-113 bp, 94 bp, 42 bp); in exon 30 the loss of a FokI site (N-159 bp, 132 bp, 2 bp;

M-290 bp, 2 bp); in exon33 the gain of a DdeI site (N-108 bp, 68 bp, 41 bp, 35bp, 22bp, 10 bp; M-108 bp, 43 bp, 41 bp, 35 bp, 25 bp, 22 bp, 10 bp), and in exon 37 the loss of an AvaII site (N-231 bp, 108 bp; M-339 bp). Segregation analysis was performed using all available family members. Genomic DNA samples were amplified by PCR, as described above and cut with the appropriate restriction enzyme (FIG. 7). The products were separated on 2% SEPARIDE/1% agarose gels and visualized by ethidium bromide staining. Segregation analysis for the one base insertion in exon 27 was based on separation of radioactively labelled PCR products (N-207 bp; M-208 bp) in 6% polyacrylamide gels. Routinely, a minimum of 100 random Caucasian control chromosomes were also evaluated for the presence of each of the nucleotide changes by the methodology described for the segregation analyses.

Example 4

Identification and Isolation of the Sequence of the Murine CACNA1F Orthologue

Murine eye mRNA was reverse-transcribed and PCR, isolation of fragments and sequencing of the DNA was carried out as described above in Example 1. Primer sets for exons 6–10, 10–15, 20–28, 24–32 and 35–38 (FIG. 2) yielded PCR products from murine retina cDNA which upon sequencing were determined to contain murine CACNA1F sequence. Mouse specific primers sets, whose products would cover exons 15–21, 32–38 and 38–42 were designed as follows:

TABLE 1

| Exons Amplified | Forward Primer | Reverse Primer |
| --- | --- | --- |
| 15–21 | atctggtggcatctttgctc (SEQ ID NO: 9) | agcagccagggacacactac (SEQ ID NO: 10) |
| 32/33–38 | ggcgagagttcagaggacag (SEQ ID NO: 11) | ccacatccaagtgttgatgc (SEQ ID NO: 12) |
| 38–42 | ggatcaagccaaccagga (SEQ ID NO: 13) | ctttggttcccttgggct (SEQ ID NO: 14) |
| 40N–48N | ttccggagaaggaaagaaaa (SEQ ID NO: 15) | cacaaatcgtgggtcttgg (SEQ ID NO: 16) |

Sequencing was performed with the primers that were used to amplify the PCR products. When sequencing did not cover the entire PCR product, new mouse-specific primers were designed as follows:

TABLE 2

| Primer Name | Primer Sequence |
| --- | --- |
| mJM8Ex20F2 | actcaagatgacagtgtttg (SEQ ID NO: 17) |
| mJM8Ex28R2 | cctggtttccagcactgtgt (SEQ ID NO: 18) |
| mJMC8Ex6-10(F2) | actgaaccataccgagtgcc (SEQ ID NO: 19) |
| mJMC8Ex6-10(R2) | tcagcctgtgtgatccagtc (SEQ ID NO: 20) |
| mJMC8Ex10-15(F2) | atgaaaacaaggatctgccg (SEQ ID NO: 21) |
| mJMC8Ex10-15(R2) | gagacgtacacatcggagca (SEQ ID NO: 22) |
| mJMC8Ex38mJMC8Ex38-46F3 | cacctcactggtcagca (SEQ ID NO: 23) |

The methods above yielded all but the 5' and 3' sequences of the murine CACNA1F gene. To determine these sequences, 5' and 3' rapid amplification of cDNA Ends (RACE) was performed using the Marathon™ cDNA Amplification kit (Clontech). Total RNA was extracted from mouse eyes, and polyA$^+$ RNA was isolated. Double stranded cDNA was synthesized, blunt ended and the Marathon™ Adaptor was ligated to the ends of the cDNA.

Primers were designed according to the specifications outlined in the CLONTECH manual for touchdown PCR. Two sets of primers, specific to the 5' and 3' ends of the murine CACNA1F gene, were used. These sets included a primer that lay closer to each end of the cDNA for nested amplification:

TABLE 3

| End of cDNA | First gene specific primer | Nested gene specific primer |
| --- | --- | --- |
| 5' end | catggcatcctgcatccagtagagg (SEQ ID NO: 24) | gtccgaggaatagctcgagtccgatg (SEQ ID NO: 25) |
| 3" end | ctcccaaccacacaggagaagctctg (SEQ ID NO: 26) | cccctgttgttggtggaggaatctac (SEQ ID NO: 27) |

What is claimed is:

1. An isolated DNA molecule comprising a sequence of nucleotides that encodes an $(alpha)_1F$-subunit of a mammalian retinal calcium channel, and selected from the group consisting of:

(a) the sequence set forth in SEQ ID NO: 1;

(b) a sequence of nucleotides that encodes the sequence of amino acids set forth in SEQ ID NO: 2;

(c) the sequence set forth in SEQ ID NO: 3;

(d) a sequence of nucleotides that encodes the sequence of amino acids set forth in SEQ ID NO: 4;

(e) the sequence set forth in SEQ ID NO: 5;

(f) a sequence of nucleotides that encodes the sequence of amino acids set forth in SEQ ID NO: 6;

(g) naturally occurring allelic variants of said sequences.

2. A DNA molecule of claim 1 wherein the DNA molecule encodes a murine retinal $(alpha)_{1F}$-subunit and has a sequence of nucleotides selected from a group consisting of:

(a) the sequence set forth in SEQ ID NO 5; or (b) a sequence of nucleotides that encodes the sequence of amino acids set forth in SEQ ID NO 6.

3. An isolated RNA sequence that encodes an $(alpha)_{1F}$-subunit of a mammalian retinal calcium channel as claimed in claim 1.

4. An expression vector comprising the nucleotide sequence of claim 1.

5. An expression vector of claim 4 wherein the expression vector is a mammalian expression vector.

6. A cell comprising a heterologous DNA comprising a nucleotide sequence of claim 1.

7. A cell of claim 6 wherein the cell is a cultured eukaryotic cell.

* * * * *

SEQUENCE LISTING

```
<160> NUMBER OF SEQ ID NOS: 138

<210> SEQ ID NO 1
<211> LENGTH: 5813
<212> TYPE: DNA
<213> ORGANISM: Homo sapiens

<400> SEQUENCE: 1
atgtcggaat ctgaaggcgg gaaaggtgag agaatccttc catccctgca gacccttgga      60
gcaagcatcg tggagtggaa gcccttcgac atcctcatcc tgctgaccat ctttgccaac     120
tgcgtggccc tgggagttta catcccttc cctgaggacg actccaacac tgccaaccac     180
aacctggagc aggtggagta cgtattcctg gtgattttca ctgtggagac ggtgctcaag     240
atcgtggcct acggctggt gctccacccc agcgcctaca tccgcaatgg ctggaaccta     300
ctcgacttca tcatcgtcgt ggtcgggctg ttcagcgttc tgctggagca gggccccgga     360
```

```
cggccaggcg acgccccgca caccgggga aagccaggag gcttcgatgt gaaggcattg    420
agggcgtttc gggtgctgcg gccactgagg ctggtgtctg gggtcccgag cctgcacata    480
gtgctcaatt ccatcatgaa ggctctggtg ccgctgctgc acattgcact gctcgtgctc    540
ttcgtcatca tcatttatgc catcattggg ctcgagctgt tccttggacg aatgcacaag    600
acgtgctact tcctgggatc cgacatgaaa gcggaggagg acccatcgcc ctgtgcgtct    660
tcgggatcag ggcgtgcgtg cacgctgaac cagactgagt gccgcgggcg ctggccaggg    720
cccaatggag gcatcaccaa cttttgacaac ttcttcttcg ccatgctgac agtcttccag    780
tgtgtcacca tggaaggctg gaccgatgtg ctctactgga tgcaagatgc catggggtat    840
gaactgccct gggtgtactt tgtgagcctt gtcatctttg ggtccttctt cgtcctcaac    900
cttgtgcttg gcgtcctgag tggggagttc tccaaggaga gagagaaagc gaaagctcgc    960
ggggacttcc agaagcagcg ggagaagcag cagatggagg aagacctgcg gggctacctg   1020
gactggatca ctcaagccga agagctggac atggaggacc cctccgccga tgacaacctt   1080
ggttctatgg ctgaagaggg ccgggcgggc catcggccac agctggccga gctgaccaat   1140
aggaggcgtg gacgtctgcg ctggttcagt cattctactc gctccacaca ctccaccagc   1200
agccatgcca gcctcccagc cagtgacacc ggttccatga cagagaccca aggcgatgag   1260
gatgaggagg aggggctct ggccagctgt acacgctgcc taaacaagat catgaaaacc   1320
agagtctgcc gccgcctccg ccgagccaac cgggtccttc gggcacgctg ccgtcgggca   1380
gtgaagtcca atgcctgcta ctgggctgtg ctgttgctcg tcttcctcaa cacgttgacc   1440
atcgcctctg agcaccacgg gcagcctgtg tggctcaccc agatccagga gtatgccaac   1500
aaagtgttgc tctgtctgtt cacggtggag atgcttctca aattgtacgg tctgggcccc   1560
tctgcctatg tgtcttcctt cttcaaccgc tttgactgct tgtggtctg tgggggcatc   1620
ctagagacca ccttggtgga ggtgggcgcc atgcagccc tgggcatctc agtgctccga   1680
tgtgtgcgcc tcctcaggat ctttaaggtc accagacact gggcttctct gagcaatctg   1740
gtggcatccc tgctcaattc aatgaaatcc atcgcatcct gctgcttct cctcttcctc   1800
ttcatcatta tcttctccct gcttggcatg cagctgtttg ggggcaagtt caactttgac   1860
cagacccaca ccaagcgaag cacctttgac acgttccccc aggccctcct cactgtcttt   1920
cagatcctga caggtgagga ctggaacgtg gtcatgtatg atggtatcat ggcatatggt   1980
ggcccttct tcccaggaat gttggtgtgc atctatttca tcattctctt catctgtggc   2040
aactacatcc tgttgaacgt gtttcttgcc attgctgtgg acaacctggc cagtggagat   2100
gcaggcactg ccaaggacaa gggcggggag aagagcaatg agaaggatct cccacaggag   2160
aatgaaggcc tggtgcctgg tgtggagaaa gaggaagagg agggtgcaag gagggaagga   2220
gcagacatgg aggaggagga ggaggaggaa gaagaggaag aagaggaaga agaggaagag   2280
ggtgcagggg gtgtggaact cctgcaggaa gttgtaccca aggagaaggt ggtacccatc   2340
cctgagggca gcgccttctt ctgcctcagc caaaccaacc cgctgaggaa gggctgccac   2400
accctcatcc accatcatgt cttcaccaat cttatcctgg tgttcatcat cctcagcagt   2460
gtgtccctgg ccgctgagga ccccatccga gcccactcct tccgcaacca tattctgggt   2520
tacttcgatt atgccttcac ctccattttc actgtggaga ttctactaaa gatgacagtg   2580
tttggggcct tcctgcaccg cggctccttc tgccgtagct ggtttaatat gttggatctg   2640
ctggtggtca gtgtgtccct catctccttt ggcatccact ccagcgccat ctcggtggtg   2700
aagattctgc gagtactccg agtactgcgg cccctccgag ccatcaacag ggccaaggga   2760
```

```
ctcaagcatg tggtgcagtg tgtatttgtg gccatccgga ccatcggaaa catcatgatt    2820
gtcaccacac ttctgcaatt tatgttcgcc tgcatcgggg tgcagctctt caagggggaaa   2880
ttctacacct gcacggacga ggccaaacac acccctcaag aatgcaaggg ctccttcctg    2940
gtatacccag atggagacgt gtcacggccc ctggtccggg agcggctctg ggtcaacagt    3000
gatttcaact ttgacaatgt cctttcagcc atgatggccc tgttcactgt ctccaccttt    3060
gaaggctggc ctgcactgct atacaaggcc atcgatgcat atgcagagga ccatggcccc    3120
atctataatt accgtgtgga gatctcagtg ttcttcattg tctacatcat catcattgcg    3180
ttcttcatga tgaacatctt cgtgggcttc gtcatcatca ctttccgtgc ccagggcgag    3240
caggagtacc aaaactgtga gctggacaag aaccagcgtc aatgtgtgga atatgccctc    3300
aaggcccagc cactccgccg ttacatcccc aagaacccgc atcagtatcg tgtgtgggcc    3360
actgtgaact ctgctgcctt tgagtacctg atgttcctgc tcatcctgct caacacagtt    3420
gctagcccca tgcagcacta tgagcagact gctcccttca actatgccat ggacatcctc    3480
aacatggtct tcactggcct cttcactatt gagatggtgc tcaaaatcat cgccttcaag    3540
cccaagcatt acttcactga tgcctggaac acgtttgacg ctcttattgt ggtgggcagc    3600
atagtggata ttgccgtcac tgaagtcaat aatggtggcc accttggcga gagctctgag    3660
gacagctccc gcatttccat taccttcttt cgcctcttcc gagttatgcg gctggtcaag    3720
cttctcagta agggtgaagg gatccgcaca ttgctctgga cattcatcaa gtccttccag    3780
gccttgccct atgtggctct tctcatcgca atgatattct tcatctatgc cgtcattggc    3840
atgcagatgt tcggcaaggt ggctcttcag gatggcacac agataaaccg aaacaacaac    3900
ttccagacct ttccacaggc tgtgctgctt ctgttcaggt gtgccactgg tgaggcatgg    3960
caggagataa tgcttgccag ccttcccgga aatcggtgtg atcctgagtc tgacttcggc    4020
cctggtgaag agtttacctg tggtagcaat tttgccatcg cctatttcat cagcttcttc    4080
atgctctgtg ccttcctgat cataaatctc tttgtggctg tgatcatgga caactttgat    4140
tatctcacca gagattggtc catcctgggc ccccatcacc ttgatgaatt caagaggatc    4200
tggtctgaat atgaccctgg ggccaagggc cgcatcaaac acttggatgt ggttgccctg    4260
ctgagacgta tccagccccc tctgggattt gggaagctgt gcccacaccg agtggcctgc    4320
aagagacttg tggcaatgaa catgcccctc aactcagatg ggacggtgac attcaacgcc    4380
acactctttg ccctggtccg gacatccctg aagatcaaaa cagaagggaa cctggagcaa    4440
gccaaccagg agctgcggat tgtcatcaaa aagatctgga agcggatgaa acagaagctg    4500
ctagatgagg tcatcccccc accagacgag gaggaggtca ccgtgggcaa attctacgcc    4560
acatttctga tccaggacta tttccgcaaa ttccggcgga ggaaagaaaa agggctacta    4620
ggcaacgacg ccgcccctag cacctcttcc gcccttcagg ctggtctgcg gagcctgcag    4680
gacttgggtc ctgagatgcg gcaggccctc acctgtgaca cagaggagga ggaagaagag    4740
gggcaggagg gagtggagga ggaagatgaa aaggacttgg aaaactaacaa agccacgatg   4800
gtctcccagc cctcagctcg ccggggctcc gggattctg tgtctctgcc tgtcggggac     4860
agacttccag attcactctc ctttgggccc agtgatgatg acaggggggac tcccacctcc   4920
agtcagccca gtgtgcccca ggctggatcc aacacccaca ggagaggctc tggggctctc   4980
attttcacca tccagaagaga aggaaattct cagcccaagg gaaccaaagg gcaaaacaag   5040
caagatgagg atgaggaagt ccctgatcgg cttcctacc tagatgagca ggcagggact    5100
```

-continued

```
cccccgtgct cagtcctttt gccacctcac agagctcaga gatacatgga tgggcacctg   5160
gtaccacgcc gccgtctgct gccccccaca cctgcaggtc ggaagccctc cttcaccatc   5220
cagtgtctgc agcgccaggg cagttgtgag gatttaccca tcccaggcac ctatcatcgt   5280
gggcgaaatt cagggcccaa tagggctcag ggttcctggg caacaccacc tcagcggggt   5340
cggctcctgt atgccccgct gttgttggtg gaagagggcg cagcggggga ggggtacctc   5400
ggcagatcca gtggcccact gcgcaccttc acctgtctgc acgtgcctgg aacccactcg   5460
gaccccagcc atgggaagag gggcagtgcc gacagcttgg tggaggctgt gcttatctca   5520
gagggtctgg gcctctttgc tcgagaccca cgtttcgtgg ccctggccaa gcaggagatt   5580
gcagatgcgt gtcgcctgac gctggatgag atggacaatg ctgccagtga cctgctggca   5640
cagggaacca gctctctcta tagcgacgag gagtccatcc tctcccgctt cgatgaggag   5700
gacttgggag acgagatggc ctgcgtccac gccctctgaa ttcccacccc tccccaactg   5760
ctcaataaac ctcctgccct cccctcccca gcaggaggca ggcatggacc aca           5813
```

<210> SEQ ID NO 2
<211> LENGTH: 1912
<212> TYPE: PRT
<213> ORGANISM: Homo sapiens

<400> SEQUENCE: 2

```
Met Ser Glu Ser Glu Gly Gly Lys Gly Glu Arg Ile Leu Pro Ser Leu
 1               5                  10                  15

Gln Thr Leu Gly Ala Ser Ile Val Glu Trp Lys Pro Phe Asp Ile Leu
                20                  25                  30

Ile Leu Leu Thr Ile Phe Ala Asn Cys Val Ala Leu Gly Val Tyr Ile
            35                  40                  45

Pro Phe Pro Glu Asp Asp Ser Asn Thr Ala Asn His Asn Leu Glu Gln
        50                  55                  60

Val Glu Tyr Val Phe Leu Val Ile Phe Thr Val Glu Thr Val Leu Lys
65                  70                  75                  80

Ile Val Ala Tyr Gly Leu Val Leu His Pro Ser Ala Tyr Ile Arg Asn
                85                  90                  95

Gly Trp Asn Leu Leu Asp Phe Ile Ile Val Val Gly Leu Phe Ser
                100                 105                 110

Val Leu Leu Glu Gln Gly Pro Gly Arg Pro Gly Asp Ala Pro His Thr
            115                 120                 125

Gly Gly Lys Pro Gly Gly Phe Asp Val Lys Ala Leu Arg Ala Phe Arg
        130                 135                 140

Val Leu Arg Pro Leu Arg Leu Val Ser Gly Val Pro Ser Leu His Ile
145                 150                 155                 160

Val Leu Asn Ser Ile Met Lys Ala Leu Val Pro Leu Leu His Ile Ala
                165                 170                 175

Leu Leu Val Leu Phe Val Ile Ile Tyr Ala Ile Ile Gly Leu Glu
            180                 185                 190

Leu Phe Leu Gly Arg Met His Lys Thr Cys Tyr Phe Leu Gly Ser Asp
        195                 200                 205

Met Glu Ala Glu Asp Pro Ser Pro Cys Ala Ser Ser Gly Ser Gly
    210                 215                 220

Arg Ala Cys Thr Leu Asn Gln Thr Glu Cys Arg Gly Arg Trp Pro Gly
225                 230                 235                 240

Pro Asn Gly Gly Ile Thr Asn Phe Asp Asn Phe Phe Ala Met Leu
                245                 250                 255
```

-continued

```
Thr Val Phe Gln Cys Val Thr Met Glu Gly Trp Thr Asp Val Leu Tyr
            260                 265                 270

Trp Met Gln Asp Ala Met Gly Tyr Glu Leu Pro Trp Val Tyr Phe Val
            275                 280                 285

Ser Leu Val Ile Phe Gly Ser Phe Val Leu Asn Leu Val Leu Gly
            290                 295                 300

Val Leu Ser Gly Glu Phe Ser Lys Glu Arg Glu Lys Ala Lys Ala Arg
305                 310                 315                 320

Gly Asp Phe Gln Lys Gln Arg Glu Lys Gln Gln Met Glu Glu Asp Leu
                    325                 330                 335

Arg Gly Tyr Leu Asp Trp Ile Thr Gln Ala Glu Glu Leu Asp Met Glu
            340                 345                 350

Asp Pro Ser Ala Asp Asp Asn Leu Gly Ser Met Ala Glu Glu Gly Arg
            355                 360                 365

Ala Gly His Arg Pro Gln Leu Ala Glu Leu Thr Asn Arg Arg Arg Gly
            370                 375                 380

Arg Leu Arg Trp Phe Ser His Ser Thr Arg Ser Thr His Ser Thr Ser
385                 390                 395                 400

Ser His Ala Ser Leu Pro Ala Ser Asp Thr Gly Ser Met Thr Glu Thr
            405                 410                 415

Gln Gly Asp Glu Asp Glu Glu Gly Ala Leu Ala Ser Cys Thr Arg
            420                 425                 430

Cys Leu Asn Lys Ile Met Lys Thr Arg Val Cys Arg Arg Leu Arg Arg
            435                 440                 445

Ala Asn Arg Val Leu Arg Ala Arg Cys Arg Arg Ala Val Lys Ser Asn
450                 455                 460

Ala Cys Tyr Trp Ala Val Leu Leu Val Phe Leu Asn Thr Leu Thr
465                 470                 475                 480

Ile Ala Ser Glu His His Gly Gln Pro Val Trp Leu Thr Gln Ile Gln
                    485                 490                 495

Glu Tyr Ala Asn Lys Val Leu Leu Cys Leu Phe Thr Val Glu Met Leu
            500                 505                 510

Leu Lys Leu Tyr Gly Leu Gly Pro Ser Ala Tyr Val Ser Ser Phe Phe
            515                 520                 525

Asn Arg Phe Asp Cys Phe Val Val Cys Gly Gly Ile Leu Glu Thr Thr
            530                 535                 540

Leu Val Glu Val Gly Ala Met Gln Pro Leu Gly Ile Ser Val Leu Arg
545                 550                 555                 560

Cys Val Arg Leu Leu Arg Ile Phe Lys Val Thr Arg His Trp Ala Ser
                    565                 570                 575

Leu Ser Asn Leu Val Ala Ser Leu Leu Asn Ser Met Lys Ser Ile Ala
            580                 585                 590

Ser Leu Leu Leu Leu Leu Phe Leu Phe Ile Ile Ile Phe Ser Leu Leu
            595                 600                 605

Gly Met Gln Leu Phe Gly Gly Lys Phe Asn Phe Asp Gln Thr His Thr
            610                 615                 620

Lys Arg Ser Thr Phe Asp Thr Phe Pro Gln Ala Leu Leu Thr Val Phe
625                 630                 635                 640

Gln Ile Leu Thr Gly Glu Asp Trp Asn Val Val Met Tyr Asp Gly Ile
            645                 650                 655

Met Ala Tyr Gly Gly Pro Phe Pro Gly Met Leu Val Cys Ile Tyr
            660                 665                 670
```

```
-continued

Phe Ile Ile Leu Phe Ile Cys Gly Asn Tyr Ile Leu Leu Asn Val Phe
            675                 680                 685

Leu Ala Ile Ala Val Asp Asn Leu Ala Ser Gly Asp Ala Gly Thr Ala
    690                 695                 700

Lys Asp Lys Gly Gly Glu Lys Ser Asn Glu Lys Asp Leu Pro Gln Glu
705                 710                 715                 720

Asn Glu Gly Leu Val Pro Gly Val Glu Lys Glu Glu Glu Gly Ala
            725                 730                 735

Arg Arg Glu Gly Ala Asp Met Glu Glu Glu Glu Glu Glu Glu
        740                 745                 750

Glu Glu Glu Glu Glu Glu Glu Gly Ala Gly Gly Val Glu Leu Leu
        755                 760                 765

Gln Glu Val Val Pro Lys Glu Lys Val Val Pro Ile Pro Glu Gly Ser
    770                 775                 780

Ala Phe Phe Cys Leu Ser Gln Thr Asn Pro Leu Arg Lys Gly Cys His
785                 790                 795                 800

Thr Leu Ile His His Val Phe Thr Asn Leu Ile Leu Val Phe Ile
            805                 810                 815

Ile Leu Ser Ser Val Ser Leu Ala Ala Glu Asp Pro Ile Arg Ala His
            820                 825                 830

Ser Phe Arg Asn His Ile Leu Gly Tyr Phe Asp Tyr Ala Phe Thr Ser
        835                 840                 845

Ile Phe Thr Val Glu Ile Leu Leu Lys Met Thr Val Phe Gly Ala Phe
    850                 855                 860

Leu His Arg Gly Ser Phe Cys Arg Ser Trp Phe Asn Met Leu Asp Leu
865                 870                 875                 880

Leu Val Val Ser Val Ser Leu Ile Ser Phe Gly Ile His Ser Ser Ala
            885                 890                 895

Ile Ser Val Val Lys Ile Leu Arg Val Leu Arg Val Leu Arg Pro Leu
        900                 905                 910

Arg Ala Ile Asn Arg Ala Lys Gly Leu Lys His Val Val Gln Cys Val
            915                 920                 925

Phe Val Ala Ile Arg Thr Ile Gly Asn Ile Met Ile Val Thr Thr Leu
    930                 935                 940

Leu Gln Phe Met Phe Ala Cys Ile Gly Val Gln Leu Phe Lys Gly Lys
945                 950                 955                 960

Phe Tyr Thr Cys Thr Asp Glu Ala Lys His Thr Pro Gln Glu Cys Lys
            965                 970                 975

Gly Ser Phe Leu Val Tyr Pro Asp Gly Asp Val Ser Arg Pro Leu Val
            980                 985                 990

Arg Glu Arg Leu Trp Val Asn Ser Asp Phe Asn Phe Asp Asn Val Leu
        995                 1000                1005

Ser Ala Met Met Ala Leu Phe Thr Val Ser Thr Phe Glu Gly Trp
    1010                1015                1020

Pro Ala Leu Leu Tyr Lys Ala Ile Asp Ala Tyr Ala Glu Asp His
    1025                1030                1035

Gly Pro Ile Tyr Asn Tyr Arg Val Glu Ile Ser Val Phe Phe Ile
    1040                1045                1050

Val Tyr Ile Ile Ile Ile Ala Phe Phe Met Met Asn Ile Phe Val
    1055                1060                1065

Gly Phe Val Ile Ile Thr Phe Arg Ala Gln Gly Glu Gln Glu Tyr
    1070                1075                1080

Gln Asn Cys Glu Leu Asp Lys Asn Gln Arg Gln Cys Val Glu Tyr
```

-continued

```
              1085                1090                1095

Ala Leu Lys Ala Gln Pro Leu Arg Arg Tyr Ile Pro Lys Asn Pro
              1100                1105                1110

His Gln Tyr Arg Val Trp Ala Thr Val Asn Ser Ala Ala Phe Glu
              1115                1120                1125

Tyr Leu Met Phe Leu Leu Ile Leu Leu Asn Thr Val Ala Leu Ala
              1130                1135                1140

Met Gln His Tyr Glu Gln Thr Ala Pro Phe Asn Tyr Ala Met Asp
              1145                1150                1155

Ile Leu Asn Met Val Phe Thr Gly Leu Phe Thr Ile Glu Met Val
              1160                1165                1170

Leu Lys Ile Ile Ala Phe Lys Pro Lys His Tyr Phe Thr Asp Ala
              1175                1180                1185

Trp Asn Thr Phe Asp Ala Leu Ile Val Val Gly Ser Ile Val Asp
              1190                1195                1200

Ile Ala Val Thr Glu Val Asn Asn Gly Gly His Leu Gly Glu Ser
              1205                1210                1215

Ser Glu Asp Ser Ser Arg Ile Ser Ile Thr Phe Phe Arg Leu Phe
              1220                1225                1230

Arg Val Met Arg Leu Val Lys Leu Leu Ser Lys Gly Glu Gly Ile
              1235                1240                1245

Arg Thr Leu Leu Trp Thr Phe Ile Lys Ser Phe Gln Ala Leu Pro
              1250                1255                1260

Tyr Val Ala Leu Leu Ile Ala Met Ile Phe Phe Ile Tyr Ala Val
              1265                1270                1275

Ile Gly Met Gln Met Phe Gly Lys Val Ala Leu Gln Asp Gly Thr
              1280                1285                1290

Gln Ile Asn Arg Asn Asn Asn Phe Gln Thr Phe Pro Gln Ala Val
              1295                1300                1305

Leu Leu Leu Phe Arg Cys Ala Thr Gly Glu Ala Trp Gln Glu Ile
              1310                1315                1320

Met Leu Ala Ser Leu Pro Gly Asn Arg Cys Asp Pro Glu Ser Asp
              1325                1330                1335

Phe Gly Pro Gly Glu Glu Phe Thr Cys Gly Ser Asn Phe Ala Ile
              1340                1345                1350

Ala Tyr Phe Ile Ser Phe Phe Met Leu Cys Ala Phe Leu Ile Ile
              1355                1360                1365

Asn Leu Phe Val Ala Val Ile Met Asp Asn Phe Asp Tyr Leu Thr
              1370                1375                1380

Arg Asp Trp Ser Ile Leu Gly Pro His His Leu Asp Glu Phe Lys
              1385                1390                1395

Arg Ile Trp Ser Glu Tyr Asp Pro Gly Ala Lys Gly Arg Ile Lys
              1400                1405                1410

His Leu Asp Val Val Ala Leu Leu Arg Arg Ile Gln Pro Pro Leu
              1415                1420                1425

Gly Phe Gly Lys Leu Cys Pro His Arg Val Ala Cys Lys Arg Leu
              1430                1435                1440

Val Ala Met Asn Met Pro Leu Asn Ser Asp Gly Thr Val Thr Phe
              1445                1450                1455

Asn Ala Thr Leu Phe Ala Leu Val Arg Thr Ser Leu Lys Ile Lys
              1460                1465                1470

Thr Glu Gly Asn Leu Glu Gln Ala Asn Gln Glu Leu Arg Ile Val
              1475                1480                1485
```

```
Ile Lys Lys Ile Trp Lys Arg Met Lys Gln Lys Leu Leu Asp Glu
    1490                1495                1500

Val Ile Pro Pro Asp Glu Glu Val Thr Val Gly Lys Phe
    1505                1510                1515

Tyr Ala Thr Phe Leu Ile Gln Asp Tyr Phe Arg Lys Phe Arg Arg
    1520                1525                1530

Arg Lys Glu Lys Gly Leu Leu Gly Asn Asp Ala Ala Pro Ser Thr
    1535                1540                1545

Ser Ser Ala Leu Gln Ala Gly Leu Arg Ser Leu Gln Asp Leu Gly
    1550                1555                1560

Pro Glu Met Arg Gln Ala Leu Thr Cys Asp Thr Glu Glu Glu Glu
    1565                1570                1575

Glu Glu Gly Gln Glu Gly Val Glu Glu Asp Glu Lys Asp Leu
    1580                1585                1590

Glu Thr Asn Lys Ala Thr Met Val Ser Gln Pro Ser Ala Arg Arg
    1595                1600                1605

Gly Ser Gly Ile Ser Val Ser Leu Pro Val Gly Asp Arg Leu Pro
    1610                1615                1620

Asp Ser Leu Ser Phe Gly Pro Ser Asp Asp Arg Gly Thr Pro
    1625                1630                1635

Thr Ser Ser Gln Pro Ser Val Pro Gln Ala Gly Ser Asn Thr His
    1640                1645                1650

Arg Arg Gly Ser Gly Ala Leu Ile Phe Thr Ile Pro Glu Glu Gly
    1655                1660                1665

Asn Ser Gln Pro Lys Gly Thr Lys Gly Gln Asn Lys Gln Asp Glu
    1670                1675                1680

Asp Glu Glu Val Pro Asp Arg Leu Ser Tyr Leu Asp Glu Gln Ala
    1685                1690                1695

Gly Thr Pro Pro Cys Ser Val Leu Leu Pro Pro His Arg Ala Gln
    1700                1705                1710

Arg Tyr Met Asp Gly His Leu Val Pro Arg Arg Leu Leu Pro
    1715                1720                1725

Pro Thr Pro Ala Gly Arg Lys Pro Ser Phe Thr Ile Gln Cys Leu
    1730                1735                1740

Gln Arg Gln Gly Ser Cys Glu Asp Leu Pro Ile Pro Gly Thr Tyr
    1745                1750                1755

His Arg Gly Arg Asn Ser Gly Pro Asn Arg Ala Gln Gly Ser Trp
    1760                1765                1770

Ala Thr Pro Pro Gln Arg Gly Arg Leu Leu Tyr Ala Pro Leu Leu
    1775                1780                1785

Leu Val Glu Glu Gly Ala Ala Gly Glu Gly Tyr Leu Gly Arg Ser
    1790                1795                1800

Ser Gly Pro Leu Arg Thr Phe Thr Cys Leu His Val Pro Gly Thr
    1805                1810                1815

His Ser Asp Pro Ser His Gly Lys Arg Gly Ser Ala Asp Ser Leu
    1820                1825                1830

Val Glu Ala Val Leu Ile Ser Glu Gly Leu Gly Leu Phe Ala Arg
    1835                1840                1845

Asp Pro Arg Phe Val Ala Leu Ala Lys Gln Glu Ile Ala Asp Ala
    1850                1855                1860

Cys Arg Leu Thr Leu Asp Glu Met Asp Asn Ala Ala Ser Asp Leu
    1865                1870                1875
```

Leu Ala Gln Gly Thr Ser Ser Leu Tyr Ser Asp Glu Glu Ser Ile
    1880                1885                1890

Leu Ser Arg Phe Asp Glu Glu Asp Leu Gly Asp Glu Met Ala Cys
    1895                1900                1905

Val His  Ala Leu
    1910

<210> SEQ ID NO 3
<211> LENGTH: 6112
<212> TYPE: DNA
<213> ORGANISM: homo sapiens

<400> SEQUENCE: 3

| | | | | | |
|---|---|---|---|---|---|
| ctccaaagct | gggggaagag | agggggggttg | tgtgcagatg | gcccttcaat | ctcgaaagaa    60 |
| agatgtcgga | atctgaaggc | gggaaagaca | ccaccccaga | gcccagtcca | gccaatgggg   120 |
| caggccctgg | tcccgaatgg | gggctgtgcc | ccgggccccc | agctgtggaa | ggtgaaagca   180 |
| gtgggcatc | aggcctaggg | accctaagc | gaagaaacca | gcacagcaag | cacaagacag   240 |
| tggcagtggc | cagtgcccag | cggtcacctc | gggcactctt | ctgcctcacc | ctggccaatc   300 |
| ctctgcgacg | gtcctgcatc | agcatcgtgg | agtggaagcc | cttcgacatc | ctcatcctgc   360 |
| tgaccatctt | tgccaactgc | gtgggccctgg | gagtttacat | cccccttccct | gaggacgact   420 |
| ccaacactgc | caaccacaac | ctggagcagg | tggagtacgt | attcctggtg | attttcactg   480 |
| tggagacggt | gctcaagatc | gtggcctacg | gctggtgct | ccaccccagc | gcctacatcc   540 |
| gcaatggctg | gaacctactc | gacttcatca | tcgtcgtggt | cgggctgttc | agcgttctgc   600 |
| tggagcaggg | ccccggacgg | ccaggcgacg | ccccgcacac | cggggggaaag | ccaggaggct   660 |
| tcgatgtgaa | ggcattgagg | gcgtttcggg | tgctgcggcc | actgaggctg | gtgtctgggg   720 |
| tcccgagcct | gcacatagtg | ctcaattcca | tcatgaaggc | tctggtgccg | ctgctgcaca   780 |
| ttgcactgct | cgtgctcttc | gtcatcatca | tttatgccat | cattgggctc | gagctgttcc   840 |
| ttggacgaat | gcacaagacg | tgctacttcc | tgggatccga | catggaagcg | gaggaggacc   900 |
| catcgccctg | tgcgtcttcg | ggatcaggc | gtgcgtgcac | gctgaaccag | actgagtgcc   960 |
| gcgggcgctg | gccagggccc | aatggaggca | tcaccaactt | tgacaacttc | ttcttcgcca  1020 |
| tgctgacagt | cttccagtgt | gtcaccatgg | aaggctggac | cgatgtgctc | tactggatgc  1080 |
| aagatgccat | ggggtatgaa | ctgccctggg | tgtactttgt | gagccttgtc | atctttgggt  1140 |
| ccttcttcgt | cctcaacctt | gtgcttggcg | tcctgagtgg | ggagttctcc | aaggagagag  1200 |
| agaaagcgaa | agctcgcggg | gacttccaga | agcagcggga | gaagcagcag | atggaggaag  1260 |
| acctgcgggg | ctacctggac | tggatcactc | aagccgaaga | gctggacatg | gaggacccct  1320 |
| ccgccgatga | caaccttggt | tctatggctg | aagagggccg | ggcgggccat | cggccacagc  1380 |
| tggccgagct | gaccaatagg | aggcgtggac | gtctgcgctg | gttcagtcat | tctactcgct  1440 |
| ccacacactc | caccagcagc | catgccagcc | tcccagccag | tgacaccggt | tccatgacag  1500 |
| agacccaagg | cgatgaggat | gaggaggagg | gggctctggc | cagctgtaca | cgctgcctaa  1560 |
| acaagatcat | gaaaaccaga | gtctgccgcc | gcctccgccg | agccaaccgg | tccttcgggg  1620 |
| cacgctgccg | tcgggcagtg | aagtccaatg | cctgctactg | ggctgtgctg | ttgctcgtct  1680 |
| tcctcaacac | gttgaccatc | gcctctgagc | accacgggca | gcctgtgtgg | ctcacccaga  1740 |
| tccaggagta | tgccaacaaa | gtgttgctct | gtctgttcac | ggtggagatg | cttctcaaat  1800 |
| tgtacggtct | gggcccctct | gcctatgtgt | cttccttctt | caaccgcttt | gactgctttg  1860 |

-continued

```
tggtctgtgg gggcatccta gagaccacct tggtggaggt gggcgccatg cagcccttgg    1920
gcatctcagt gctccgatgt gtgcgcctcc tcaggatctt aaggtcacc agacactggg     1980
cttctctgag caatcggtg gcatccctgc tcaattcaat gaaatccatc gcatccttgc     2040
tgcttctcct cttcctcttc atcattatct tctccctgct tggcatgcag ctgtttgggg    2100
gcaagttcaa ctttgaccag acccacacca agcgaagcac ctttgacacg ttcccccagg    2160
ccctcctcac tgtctttcag atcctgacag gtgaggactg gaacgtggtc atgtatgatg    2220
gtatcatggc atatggtggc cccttcttcc caggaatgtt ggtgtgcatc tatttcatca    2280
ttctcttcat ctgtggcaac tacatcctgt tgaacgtgtt tcttgccatt gctgtggaca    2340
acctggccag tggagatgca ggcactgcca aggacaaggg cggggagaag agcaatgaga    2400
aggatctccc acaggagaat aaggcctggt gcctggtgt ggagaaagag gaagaggagg    2460
gtgcaaggag ggaaggagca gacatggagg aggaggagga ggaggaagaa gaggaagaag    2520
aggaagaaga ggaagagggt gcaggggtg tggaactcct gcaggaagtt gtacccaagg    2580
agaaggtggt acccatccct gagggcagcg ccttcttctg cctcagccaa ccaacccgc    2640
tgaggaaggg ctgccacacc ctcatccacc atcatgtctt caccaatctt atcctggtgt    2700
tcatcatcct cagcagtgtg tccctggccg ctgaggaccc catccgagcc cactccttcc    2760
gcaaccatat tctgggttac ttcgattatg ccttcacctc cattttcact gtggagattc    2820
tactaaagat gacagtgttt ggggccttcc tgcaccgcgg ctccttctgc cgtagctggt    2880
ttaatatgtt ggatctgctg gtggtcagtg tgtccctcat ctcctttggc atccactcca    2940
gcgccatctc ggtggtgaag attctgcgag tactccgagt actgcggccc ctccgagcca    3000
tcaacagggc caagggactc aagcatgtgg tgcagtgtgt atttgtggcc atccggacca    3060
tcggaaacat catgattgtc accacacttc tgcaatttat gttcgcctgc atcggggtgc    3120
agctcttcaa ggggaaattc tacacctgca cggacgaggc caaacacacc cctcaagaat    3180
gcaagggctc cttcctggta tacccagatg agacgtgtc acggcccctg gtccgggagc    3240
ggctctgggt caacagtgat ttcaactttg acaatgtcct ttcagccatg atggccctgt    3300
tcactgtctc cacctttgaa ggctggcctg cactgctata caaggccatc gatgcatatg    3360
cagaggacca tggccccatc tataattacc gtgtgggagat ctcagtgttc ttcattgtct    3420
aczcatcat cattgcgttc ttcatgatga acatcttcgt gggcttcgtc atcatcactt     3480
tccgtgccca gggcgagcag gagtaccaaa actgtgagct ggacaagaac cagcgtcaat    3540
gtgtggaata tgccctcaag gcccagccac tccgccgtta catccccaag aacccgcatc    3600
atgtggaata gtgggccact gtgaactctg ctgcctttga gtacctgatg ttcctgctca    3660
tcctgctcaa cacagttgcc ctagccatgc agcactatga gcagactgct cccttcaact    3720
atgccatgga catcctcaac atggtcttca ctggcctctt cactattgag atggtgctca    3780
aaatcatcgc cttcaagccc aagcattact tcactgatgc ctggaacacg tttgacgctc    3840
ttattgtggt gggcagcata gtggatattg ccgtcactga agtcaataat ggtgccacc     3900
ttggcgagag ctctgaggac agctcccgca tttccattac cttctttcgc ctcttccgag    3960
ttatgcggct ggtcaagctt ctcagtaagg gtgaagggat ccgcacattg ctctggacat    4020
tcatcaagtc cttccaggcc ttgccctatg tggctcttct catcgcaatg atattcttca    4080
tctatgccgt cattggcatg cagatgttcg gcaaggtggc tcttcaggat ggcacacaga    4140
taaaccgaaa caacaacttc cagaccttc cacaggctgt gctgcttctg ttcaggtgtg    4200
ccaacggtga ggcatggcag gagataatgc ttgccagcct tccgggaaat cggtgtgatc    4260
```

```
ctgagtctga cttcggccct ggtgaagagt ttacctgtgg tagcaatttt gccatcgcct    4320
attcattcag cttcttcatg ctctgtgcct tcctgatcat aaatctcttt gtggctgtga    4380
tcatggacaa ctttgattat ctcaccagag attggtccat cctgggcccc catcaccttg    4440
atgaattcaa gaggatctgg tctgaatatg accctggggc caagggccgc atcaaacact    4500
tggatgtggt tgccctgctg agacgtatcc agccccctct gggatttggg aagctgtgcc    4560
cacaccgagt ggcctgcaag agacttgtgg caatgaacat gcccctcaac tcagatggga    4620
cggtgacatt caacgccaca ctctttgccc tggtccggac atccctgaag atcaaaacag    4680
aagggaacct ggagcaagcc aaccaggagc tgcggattgt catcaaaaag atctggaagc    4740
ggatgaaaca gaagctgcta gatgaggtca tcccccacc agacgaggag gaggtcaccg    4800
tgggcaaatt ctacgccaca tttctgatcc aggactattt ccgcaaattc cggcggagga    4860
aagaaaaagg gctactaggc aacgacgccg cccctagcac ctcttccgcc ttcaggctg    4920
gtctgcggag cctgcaggac ttgggtcctg agatgcggca ggccctcacc tgtgacacag    4980
aggaggagga agaagagggg caggagggag tggaggagga agatgaaaag gacttggaaa    5040
ctaacaaagc cacgatggtc tcccagccct cagctcgccg gggctccggg atttctgtgt    5100
ctctgcctgt cggggacaga cttccagatt cactctcctt tgggcccagt gatgatgaca    5160
gggggactcc cacctccagt cagcccagtg tgccccaggc tggatccaac acccacagga    5220
gaggctctgg ggctctcatt ttcaccatcc agaagaagg aaattctcag cccaagggaa    5280
ccaaagggca aaacaagcaa gatgaggatg aggaagtccc tgatcggctt tcctacctag    5340
algagcaggc agggactccc ccgtgctcag tccttttgcc acctcacaga gctcagagat    5400
acatggatgg gcacctggta ccacgccgcc gtctgctgcc ccccacacct gcaggtcgga    5460
agccctctt caccatccag tgtctgcagc gccagggcag ttgtgaggat ttacccatcc    5520
caggcaccta tcatcgtggg cgaaattcag ggcccaatag ggctcagggt tcctgggcaa    5580
caccacctca gcgggtcgg ctcctgtatg ccccgctgtt gttggtggaa gagggcgcag    5640
cgggggaggg gtacctcggc agatccagtg gcccactgcg caccttcacc tgtctgcacg    5700
tgcctggaac ccactcggac cccagccatg ggaagagggg cagtgccgac agcttggtgg    5760
aggctgtgct tatctcagag ggtctgggcc tctttgctcg agacccacgt ttcgtggccc    5820
tggccaagca ggagattgca gatgcgtgtc gcctgacgct ggatgagatg gacaatgctg    5880
ccagtgacct gctggcacag gaaccagct ctctctatag cgacgaggag tccatcctct    5940
cccgcttcga tgaggaggac ttgggagacg agatggcctg cgtccacgcc ctctgaattc    6000
ccaccctcc ccaactgctc aataaacctc ctgccctccc ctcccagca ggaggcaggc    6060
atggaccaca aaaaaaaaa aaaaaaaaa aaaaaaaaa aaaaaaaaa aa                6112
```

<210> SEQ ID NO 4
<211> LENGTH: 1977
<212> TYPE: PRT
<213> ORGANISM: Homo sapiens

<400> SEQUENCE: 4

Met Ser Glu Ser Glu Gly Gly Lys Asp Thr Thr Pro Glu Pro Ser Pro
1               5                   10                  15

Ala Asn Gly Ala Gly Pro Gly Pro Glu Trp Gly Leu Cys Pro Gly Pro
            20                  25                  30

Pro Ala Val Glu Gly Glu Ser Ser Gly Ala Ser Gly Leu Gly Thr Pro
        35                  40                  45

```
Lys Arg Arg Asn Gln His Ser Lys His Lys Thr Val Ala Val Ala Ser
 50                  55                  60
Ala Gln Arg Ser Pro Arg Ala Leu Phe Cys Leu Thr Leu Ala Asn Pro
 65                  70                  75                  80
Leu Arg Arg Ser Cys Ile Ser Ile Val Glu Trp Lys Pro Phe Asp Ile
                 85                  90                  95
Leu Ile Leu Leu Thr Ile Phe Ala Asn Cys Val Ala Leu Gly Val Tyr
                100                 105                 110
Ile Pro Phe Pro Glu Asp Ser Asn Thr Ala Asn His Asn Leu Glu
        115                 120                 125
Gln Val Glu Tyr Val Phe Leu Val Ile Phe Thr Val Glu Thr Val Leu
130                 135                 140
Lys Ile Val Ala Tyr Gly Leu Val Leu His Pro Ser Ala Tyr Ile Arg
145                 150                 155                 160
Asn Gly Trp Asn Leu Leu Asp Phe Ile Ile Val Val Gly Leu Phe
                165                 170                 175
Ser Val Leu Leu Glu Gln Gly Pro Gly Arg Pro Gly Asp Ala Pro His
                180                 185                 190
Thr Gly Gly Lys Pro Gly Gly Phe Asp Val Lys Ala Leu Arg Ala Phe
                195                 200                 205
Arg Val Leu Arg Pro Leu Arg Leu Val Ser Gly Val Pro Ser Leu His
210                 215                 220
Ile Val Leu Asn Ser Ile Met Lys Ala Leu Val Pro Leu Leu His Ile
225                 230                 235                 240
Ala Leu Leu Val Leu Phe Val Ile Ile Tyr Ala Ile Ile Gly Leu
                245                 250                 255
Glu Leu Phe Leu Gly Arg Met His Lys Thr Cys Tyr Phe Leu Gly Ser
                260                 265                 270
Asp Met Glu Ala Glu Asp Pro Ser Pro Cys Ala Ser Ser Gly Ser
        275                 280                 285
Gly Arg Ala Cys Thr Leu Asn Gln Thr Glu Cys Arg Gly Arg Trp Pro
290                 295                 300
Gly Pro Asn Gly Gly Ile Thr Asn Phe Asp Asn Phe Phe Ala Met
305                 310                 315                 320
Leu Thr Val Phe Gln Cys Val Thr Met Glu Gly Trp Thr Asp Val Leu
                325                 330                 335
Tyr Trp Met Gln Asp Ala Met Gly Tyr Glu Leu Pro Trp Val Tyr Phe
                340                 345                 350
Val Ser Leu Val Ile Phe Gly Ser Phe Phe Val Leu Asn Leu Val Leu
                355                 360                 365
Gly Val Leu Ser Gly Glu Phe Ser Lys Glu Arg Glu Lys Ala Lys Ala
                370                 375                 380
Arg Gly Asp Phe Gln Lys Gln Arg Glu Lys Gln Gln Met Glu Glu Asp
385                 390                 395                 400
Leu Arg Gly Tyr Leu Asp Trp Ile Thr Gln Ala Glu Glu Leu Asp Met
                405                 410                 415
Glu Asp Pro Ser Ala Asp Asp Asn Leu Gly Ser Met Ala Glu Glu Gly
                420                 425                 430
Arg Ala Gly His Arg Pro Gln Leu Ala Glu Leu Thr Asn Arg Arg Arg
                435                 440                 445
Gly Arg Leu Arg Trp Phe Ser His Ser Thr Arg Ser Thr His Ser Thr
                450                 455                 460
```

-continued

```
Ser Ser His Ala Ser Leu Pro Ala Ser Asp Thr Gly Ser Met Thr Glu
465                 470                 475                 480

Thr Gln Gly Asp Glu Asp Glu Glu Gly Ala Leu Ala Ser Cys Thr
            485                 490                 495

Arg Cys Leu Asn Lys Ile Met Lys Thr Arg Val Cys Arg Arg Leu Arg
                500                 505                 510

Arg Ala Asn Arg Val Leu Arg Ala Arg Cys Arg Arg Ala Val Lys Ser
            515                 520                 525

Asn Ala Cys Tyr Trp Ala Val Leu Leu Val Phe Leu Asn Thr Leu
            530                 535                 540

Thr Ile Ala Ser Glu His His Gly Gln Pro Val Trp Leu Thr Gln Ile
545                 550                 555                 560

Gln Glu Tyr Ala Asn Lys Val Leu Leu Cys Leu Phe Thr Val Glu Met
                565                 570                 575

Leu Leu Lys Leu Tyr Gly Leu Gly Pro Ser Ala Tyr Val Ser Ser Phe
            580                 585                 590

Phe Asn Arg Phe Asp Cys Phe Val Val Cys Gly Gly Ile Leu Glu Thr
            595                 600                 605

Thr Leu Val Glu Val Gly Ala Met Gln Pro Leu Gly Ile Ser Val Leu
610                 615                 620

Arg Cys Val Arg Leu Leu Arg Ile Phe Lys Val Thr Arg His Trp Ala
625                 630                 635                 640

Ser Leu Ser Asn Leu Val Ala Ser Leu Leu Asn Ser Met Lys Ser Ile
                645                 650                 655

Ala Ser Leu Leu Leu Leu Leu Phe Leu Phe Ile Ile Ile Phe Ser Leu
            660                 665                 670

Leu Gly Met Gln Leu Phe Gly Gly Lys Phe Asn Phe Asp Gln Thr His
            675                 680                 685

Thr Lys Arg Ser Thr Phe Asp Thr Phe Pro Gln Ala Leu Leu Thr Val
690                 695                 700

Phe Gln Ile Leu Thr Gly Glu Asp Trp Asn Val Val Met Tyr Asp Gly
705                 710                 715                 720

Ile Met Ala Tyr Gly Gly Pro Phe Phe Pro Gly Met Leu Val Cys Ile
                725                 730                 735

Tyr Phe Ile Ile Leu Phe Ile Cys Gly Asn Tyr Ile Leu Leu Asn Val
            740                 745                 750

Phe Leu Ala Ile Ala Val Asp Asn Leu Ala Ser Gly Asp Ala Gly Thr
            755                 760                 765

Ala Lys Asp Lys Gly Gly Glu Lys Ser Asn Glu Lys Asp Leu Pro Gln
770                 775                 780

Glu Asn Glu Gly Leu Val Pro Gly Val Glu Lys Glu Glu Glu Glu Gly
785                 790                 795                 800

Ala Arg Arg Glu Gly Ala Asp Met Glu Glu Glu Glu Glu Glu Glu Glu
            805                 810                 815

Glu Glu Glu Glu Glu Glu Glu Glu Gly Ala Gly Gly Val Glu Leu
            820                 825                 830

Leu Gln Glu Val Val Pro Lys Glu Lys Val Val Pro Ile Pro Glu Gly
            835                 840                 845

Ser Ala Phe Phe Cys Leu Ser Gln Thr Asn Pro Leu Arg Lys Gly Cys
            850                 855                 860

His Thr Leu Ile His His Val Phe Thr Asn Leu Ile Leu Val Phe
865                 870                 875                 880

Ile Ile Leu Ser Ser Val Ser Leu Ala Ala Glu Asp Pro Ile Arg Ala
```

-continued

```
                885                 890                 895
His Ser Phe Arg Asn His Ile Leu Gly Tyr Phe Asp Tyr Ala Phe Thr
            900                 905                 910
Ser Ile Phe Thr Val Glu Ile Leu Leu Lys Met Thr Val Phe Gly Ala
        915                 920                 925
Phe Leu His Arg Gly Ser Phe Cys Arg Ser Trp Phe Asn Met Leu Asp
    930                 935                 940
Leu Leu Val Val Ser Val Ser Leu Ile Ser Phe Gly Ile His Ser Ser
945                 950                 955                 960
Ala Ile Ser Val Val Lys Ile Leu Arg Val Leu Arg Val Leu Arg Pro
                965                 970                 975
Leu Arg Ala Ile Asn Arg Ala Lys Gly Leu Lys His Val Val Gln Cys
            980                 985                 990
Val Phe Val Ala Ile Arg Thr Ile Gly Asn Ile Met Ile Val Thr Thr
        995                 1000                1005
Leu Leu Gln Phe Met Phe Ala Cys Ile Gly Val Gln Leu Phe Lys
    1010                1015                1020
Gly Lys Phe Tyr Thr Cys Thr Asp Glu Ala Lys His Thr Pro Gln
    1025                1030                1035
Glu Cys Lys Gly Ser Phe Leu Val Tyr Pro Asp Gly Asp Val Ser
    1040                1045                1050
Arg Pro Leu Val Arg Glu Arg Leu Trp Val Asn Ser Asp Phe Asn
    1055                1060                1065
Phe Asp Asn Val Leu Ser Ala Met Met Ala Leu Phe Thr Val Ser
    1070                1075                1080
Thr Phe Glu Gly Trp Pro Ala Leu Leu Tyr Lys Ala Ile Asp Ala
    1085                1090                1095
Tyr Ala Glu Asp His Gly Pro Ile Tyr Asn Tyr Arg Val Glu Ile
    1100                1105                1110
Ser Val Phe Phe Ile Val Tyr Ile Ile Ile Ala Phe Phe Met
    1115                1120                1125
Met Asn Ile Phe Val Gly Phe Val Ile Ile Thr Phe Arg Ala Gln
    1130                1135                1140
Gly Glu Gln Glu Tyr Gln Asn Cys Glu Leu Asp Lys Asn Gln Arg
    1145                1150                1155
Gln Cys Val Glu Tyr Ala Leu Lys Ala Gln Pro Leu Arg Arg Tyr
    1160                1165                1170
Ile Pro Lys Asn Pro His Gln Tyr Arg Val Trp Ala Thr Val Asn
    1175                1180                1185
Ser Ala Ala Phe Glu Tyr Leu Met Phe Leu Leu Ile Leu Leu Asn
    1190                1195                1200
Thr Val Ala Leu Ala Met Gln His Tyr Glu Gln Thr Ala Pro Phe
    1205                1210                1215
Asn Tyr Ala Met Asp Ile Leu Asn Met Val Phe Thr Gly Leu Phe
    1220                1225                1230
Thr Ile Glu Met Val Leu Lys Ile Ile Ala Phe Lys Pro Lys His
    1235                1240                1245
Tyr Phe Thr Asp Ala Trp Asn Thr Phe Asp Ala Leu Ile Val Val
    1250                1255                1260
Gly Ser Ile Val Asp Ile Ala Val Thr Glu Val Asn Asn Gly Gly
    1265                1270                1275
His Leu Gly Glu Ser Ser Glu Asp Ser Ser Arg Ile Ser Ile Thr
    1280                1285                1290
```

-continued

```
Phe Phe Arg Leu Phe Arg Val Met Arg Leu Val Lys Leu Leu Ser
    1295                1300                1305
Lys Gly Glu Gly Ile Arg Thr Leu Leu Trp Thr Phe Ile Lys Ser
    1310                1315                1320
Phe Gln Ala Leu Pro Tyr Val Ala Leu Leu Ile Ala Met Ile Phe
    1325                1330                1335
Phe Ile Tyr Ala Val Ile Gly Met Gln Met Phe Gly Lys Val Ala
    1340                1345                1350
Leu Gln Asp Gly Thr Gln Ile Asn Arg Asn Asn Asn Phe Gln Thr
    1355                1360                1365
Phe Pro Gln Ala Val Leu Leu Leu Phe Arg Cys Ala Thr Gly Glu
    1370                1375                1380
Ala Trp Gln Glu Ile Met Leu Ala Ser Leu Pro Gly Asn Arg Cys
    1385                1390                1395
Asp Pro Glu Ser Asp Phe Gly Pro Gly Glu Glu Phe Thr Cys Gly
    1400                1405                1410
Ser Asn Phe Ala Ile Ala Tyr Phe Ile Ser Phe Phe Met Leu Cys
    1415                1420                1425
Ala Phe Leu Ile Ile Asn Leu Phe Val Ala Val Ile Met Asp Asn
    1430                1435                1440
Phe Asp Tyr Leu Thr Arg Asp Trp Ser Ile Leu Gly Pro His His
    1445                1450                1455
Leu Asp Glu Phe Lys Arg Ile Trp Ser Glu Tyr Asp Pro Gly Ala
    1460                1465                1470
Lys Gly Arg Ile Lys His Leu Asp Val Val Ala Leu Leu Arg Arg
    1475                1480                1485
Ile Gln Pro Pro Leu Gly Phe Gly Lys Leu Cys Pro His Arg Val
    1490                1495                1500
Ala Cys Lys Arg Leu Val Ala Met Asn Met Pro Leu Asn Ser Asp
    1505                1510                1515
Gly Thr Val Thr Phe Asn Ala Thr Leu Phe Ala Leu Val Arg Thr
    1520                1525                1530
Ser Leu Lys Ile Lys Thr Glu Gly Asn Leu Glu Gln Ala Asn Gln
    1535                1540                1545
Glu Leu Arg Ile Val Ile Lys Lys Ile Trp Lys Arg Met Lys Gln
    1550                1555                1560
Lys Leu Leu Asp Glu Val Ile Pro Pro Pro Asp Glu Glu Glu Val
    1565                1570                1575
Thr Val Gly Lys Phe Tyr Ala Thr Phe Leu Ile Gln Asp Tyr Phe
    1580                1585                1590
Arg Lys Phe Arg Arg Arg Lys Glu Lys Gly Leu Leu Gly Asn Asp
    1595                1600                1605
Ala Ala Pro Ser Thr Ser Ser Ala Leu Gln Ala Gly Leu Arg Ser
    1610                1615                1620
Leu Gln Asp Leu Gly Pro Glu Met Arg Gln Ala Leu Thr Cys Asp
    1625                1630                1635
Thr Glu Glu Glu Glu Glu Gly Gln Glu Gly Val Glu Glu Glu
    1640                1645                1650
Asp Glu Lys Asp Leu Glu Thr Asn Lys Ala Thr Met Val Ser Gln
    1655                1660                1665
Pro Ser Ala Arg Arg Gly Ser Gly Ile Ser Val Ser Leu Pro Val
    1670                1675                1680
```

```
Gly Asp Arg Leu Pro Asp Ser Leu Ser Phe Gly Pro Ser Asp Asp
    1685               1690               1695

Asp Arg Gly Thr Pro Thr Ser Ser Gln Pro Ser Val Pro Gln Ala
1700               1705               1710

Gly Ser Asn Thr His Arg Arg Gly Ser Gly Ala Leu Ile Phe Thr
    1715               1720               1725

Ile Pro Glu Glu Gly Asn Ser Gln Pro Lys Gly Thr Lys Gly Gln
    1730               1735               1740

Asn Lys Gln Asp Glu Asp Glu Val Pro Asp Arg Leu Ser Tyr
    1745               1750               1755

Leu Asp Glu Gln Ala Gly Thr Pro Pro Cys Ser Val Leu Leu Pro
    1760               1765               1770

Pro His Arg Ala Gln Arg Tyr Met Asp Gly His Leu Val Pro Arg
    1775               1780               1785

Arg Arg Leu Leu Pro Pro Thr Pro Ala Gly Arg Lys Pro Ser Phe
    1790               1795               1800

Thr Ile Gln Cys Leu Gln Arg Gln Gly Ser Cys Glu Asp Leu Pro
    1805               1810               1815

Ile Pro Gly Thr Tyr His Arg Gly Arg Asn Ser Gly Pro Asn Arg
    1820               1825               1830

Ala Gln Gly Ser Trp Ala Thr Pro Pro Gln Arg Gly Arg Leu Leu
    1835               1840               1845

Tyr Ala Pro Leu Leu Leu Val Glu Glu Gly Ala Ala Gly Glu Gly
    1850               1855               1860

Tyr Leu Gly Arg Ser Ser Gly Pro Leu Arg Thr Phe Thr Cys Leu
    1865               1870               1875

His Val Pro Gly Thr His Ser Asp Pro Ser His Gly Lys Arg Gly
    1880               1885               1890

Ser Ala Asp Ser Leu Val Glu Ala Val Leu Ile Ser Glu Gly Leu
    1895               1900               1905

Gly Leu Phe Ala Arg Asp Pro Arg Phe Val Ala Leu Ala Lys Gln
    1910               1915               1920

Glu Ile Ala Asp Ala Cys Arg Leu Thr Leu Asp Glu Met Asp Asn
    1925               1930               1935

Ala Ala Ser Asp Leu Leu Ala Gln Gly Thr Ser Ser Leu Tyr Ser
    1940               1945               1950

Asp Glu Glu Ser Ile Leu Ser Arg Phe Asp Glu Glu Asp Leu Gly
    1955               1960               1965

Asp Glu Met Ala Cys Val His Ala Leu
    1970               1975

<210> SEQ ID NO 5
<211> LENGTH: 6114
<212> TYPE: DNA
<213> ORGANISM: Mus musculus

<400> SEQUENCE: 5
aagatgggag gactgtgtgc atgatggtcc ttatatctcc tgaggaggat gtcggaatct      60
gaagtcggga aagatacaac cccagagccc agtccagcca atgggactgg ccctggccct     120 gaatggggc tctgtcctgg gcctccaact gtggggactg ataccagcgg ggcgtcaggc      180
ctggggaccc caagaagaag gacccagcac aacaaacaca agactgtggc ggtggccagt     240
gctcagagat cacctcgagc gctcttctgc ctcacccta ctaatcccat tcgtcggtcc      300
tgcatcagca ttgtagagtg gaagcctttt gatattctca tcctcctgac aatctttgcc     360
```

```
aactgcgtgg cattgggggt atatatcccc ttccctgagg acgactccaa cactgctaac    420
cacaacttgg aacaggtaga atacgtgttc ctggtgattt tcaccgtgga gacagtgctc    480
aagatcgtag cctatgggct ggtgctccat cccagcgcct atattcgcaa tggctggaac    540
ctgctcgact tcatcatcgt cgtggtcggg ctgttcagcg tgctgctgga acaaggacct    600
gggcggccag gagatgcccc gcatactgga ggaaagccag gaggcttcga tgtaaaggca    660
ctgcgggcat ttagggtgct acgacctcta aggctagtgt ctgggtccc gagtctgcac     720 atagtcgtca attccatcat gaaggcgctt gtgccgctgc tgcacattgc cctgttggtg    780
ctcttcgtca ttatcattta cgccatcatc ggactcgagc tattcctcgg acgaatgcac    840
aagacatgct acttcctggg atctgatatg gaagcagagg aggacccatc accttgtgca    900
tcttctggct ctgggcgttc atgcacactg aaccataccg agtgccgcgg gcgctggcca    960
ggacccaacg gtggcatcac gaacttcgac aattttttct ttgccatgct aactgtgttc   1020
cagtgtatta ccatggaagg ctggacagac gtcctctact ggatgcagga tgccatgggg   1080
tatgagctgc cttgggtgta ctttgtgagc cttgtcatct ttgggtcctt ctttgtcctc   1140
aaccttgtgc ttggagtcct aagcggggag ttctccaagg aaagagaaaa ggcaaaagca   1200
cgaggtgact tcagaagct tcgggagaag cagcagatgg aagaagacct tcggggctac    1260
ctggactgga tcacacaggc tgaggagtta gaccttcatg acccctcagt agacggcaac   1320
ttggcttctc ttgctgaaga gggacgggcg ggccatcggc cacaactgtc agagctgacc   1380
aataggaggc gcggacggct gcgatggttc agccactcta ctcgctccac acactccacc   1440
agcagccacg ccagcctccc agccagtgac actggctcca tgacagacac ccctggagat   1500
gaggatgaag aagaggggac catggctagc tgtacacgct gcctaaacaa gattatgaaa   1560
acaaggatct gccgccactt ccgccgagcc aaccggggtc tccgtgcacg ctgccgccgg   1620
gccgtcaagt ccaacgcctg ctactgggct gtactgttgc tcgtcttcct caacacgttg   1680
accatcgctt cagagcacca tgggcagcct tgtggctca cccagaccca agagtatgcc    1740
aacaaagttc tgctctgcct cttcactgtg gagatgctcc tcaaactgta cggcctgggc   1800
ccctctgtct acgttgcctc ctttttcaac cgctttgact gcttcgtggt ctgtgggggc   1860
atcctagaaa ccactttggt ggaggtgggg gccatgcagc tcttggcat ctcagtgctc    1920 cgatgtgtac gtctcctcag gatcttcaag gtcaccaggc actgggcatc cctgagcaat   1980
ctggtggcat ctttgctcaa ttccatgaag tccatcgcct ccttgctgct tctcctcttt   2040
ctcttcatca tcatcttctc cctgcttggc atgcagctgt ttgggggcaa gttcaacttt   2100
gaccagaccc acaccaagag gagcaccttt gataccttcc cccaagccct cctcactgtc   2160
tttcagatcc tgactggtga ggattggaac gttgtcatgt atgatggtat catggcctac   2220
ggtgggccct tcttcccagg gatgctggtg tgtgtttatt tcatcatcct cttcatctgt   2280
ggcaactaca tcctgctgaa cgtgtttctt gccattgccg tggataacct agccagcggg   2340
gatgcaggca ctgccaaaga taagggcaga gagaagagca gtgaaggaaa ccctccaaag   2400
gagaacaaag tattggtgcc tggtggagag aatgaggacg caagggcgc aagaagtgaa    2460 ggagcagcac caggcatgga ggaggaggag gaggaggagg aggaagaaga agaggaggag   2520
gaggaggaag aggaaaatgg tgcaggacat gtggaactct gcaggaagt agtacccaag    2580 gagaaggtgg tacccatccc tgaaggcagt gccttcttct gccttagcca aaccaacccg   2640
cttcggaagg cctgccacac actcatacat caccatatct tcaccagtct catcctagtg   2700
```

```
ttcatcatcc tcagtagtgt gtccctggct gctgaggacc ccatccgagc tcactccttc    2760
cgaaaccata ttctgggata ttttgattat gccttcacct ccatattcac tgtggagatt    2820
ctactcaaga tgacagtgtt tggggccttc ctgcaccgag gctctttctg ccgtagctgg    2880
ttcaatctgt tggatctcct tgtggtcagt gtgtccctca tctccttcgg catccactcc    2940
agtgccatct cagttgtgaa gattctccga gtcctccgag tcctgcggcc tctccgagcc    3000
atcaacagag ccaagggact caagcatgtg gtgcagtgtg tgttcgtggc catccggacc    3060
atcggaaaca tcatgattgt caccaccctc ttgcagttca tgttcgcctg cattggtgtt    3120
cagctgttca agggaaaatt ctacagttgc actgatgagg ccaaacacac cctgaaagaa    3180
tcgaagggct ccttcctcat ctaccctgat ggagatgtgt cacgaccttt ggtccgggag    3240
cggctctggg tcaacagtga ttttaacttt gacaacgtcc tttcagccat gatggccctg    3300
ttcactgtct ctacctttga aggctggcct gcgctactat acaaggccat agatgcaaac    3360
gcagaagatg agggccctat ctacaattac catgtggaga tatcagtatt cttcattgtc    3420
tacatcatca tcatcgcctt cttcatgatg aacatctttg tgggctttgt tatcatcaca    3480
ttccgtgccc agggagagca ggagtaccaa aactgtgaac tggacaagaa ccagcgccag    3540
tgtgtggaat atgccctcaa agctcagcca ctccgccgat acatccctaa gaatcctcat    3600
cagtaccgcg tgtgggccac tgtgaactct cgtgccttg agtacctcat gtttctgctc    3660
atcctgctca acacggtggc cctagccatg cagcactatg aacagactgc tcccttaac    3720 tatgccatgg acatcctcaa catggtcttc actggcctct tcaccattga gatggtgctc    3780
aaaatcatcg cctttaaacc caagcattac tttgcagatg cctggaatac gtttgatgct    3840
ctcattgtag tgggcagtgt agtcgacatc gccgtcacag aagtcaataa cggaggccat    3900
cttggcgaga gttcagagga cacgtcccgc atatctatca cgttctttcg cctcttccga    3960
gtcatgaggc tggtcaagct tctgagtaag ggtgaaggga tccgcacact gctctggaca    4020
ttcatcaagt cttttccaggc cttgccctat gtggcacttc tcatagcaat gatattcttc    4080
atctatgcag tcattggcat gcagatgttt ggcttggtgg ctcttcagga cggcacgcag    4140
ataaatcgaa acaacaattt ccagaccttt ccgcaggctg tgctgcttct gttcaggtgt    4200
gccactggtg aggcctggca agagataatg ctagccagcc ttccaggaaa tcgatgtgac    4260
cctgagtctg actttggccc aggcgaggaa tttacctgtg gtagcagttt tgccatcgtc    4320
tacttcatca gcttctttat gctctgtgcc ttcctgatta taaatctctt tgtggctgta    4380
atcatggata actttgatta cctaaccaga gattggtcta tcctgggacc ccaccacctt    4440
gatgaattca gaggatctg gtctgaatat gaccccggag ccaagggccg catcaagcac    4500
ttggatgtgg ttgccctgct gagacgcatc cagcccccat tgggatttgg aaagctatgc    4560
ccacaccgag tggcctgcaa gagactcgtg gcaatgaatg tgcccctcaa ctcagatgga    4620
acagtgacat tcaacgctac actctttgcc ctggtgcgga catccctgaa gatcaagaca    4680
gaagggaacc tggatcaagc caaccaggag cttcggatgg tcatcaaaaa gatctggaag    4740
cggataaagc agaaattgtt ggatgaggtc atccctcctc ccgatgagga ggaggtcact    4800
gtgggaaaat tctatgccac attcctgatc caagattatt tccgaaaatt ccggagaagg    4860
aaagaaaagg ggctactagg aagagaggcc ccaacaagca catcctctgc cctccaggct    4920
ggtctaagga gcctgcagga cttgggtcct gagatccgtc aagccctcac ctatgtcact    4980
gaggaagaag aggaagagga gaggcagtgg ggtcaggagg ctgaggaaga ggaagctgag    5040
aacaacccag aaccatacaa agactccata gactcccagc cccaatctcg atggaactct    5100
```

-continued

```
aggatttcgg tgtctctacc tgttaaggag aaacttccag attctctctc aactgggccg    5160
agtgatgatg atgggctggc tcccaactcc aggcagccca gtgtgataca ggctggctcc    5220
caaccacaca ggagaagctc tggggttttc atgttcacta tcccggaaga aggaagtatt    5280
cagctcaagg gaactcaagg gcaggacaat cagaatgagg aacaggaact ccctgactgg    5340
actcctgacc tggatcgagc aggccgggac tccttcgaac ccagtccttt taccacctca    5400
ctggtccagc aacacgtaaa cgggcacatg tcgacgccga cgtttgctgc ccccacgcc    5460 tgcaggtcgg agccctcctt caccatccag tgtctgcaac gctgggcag ttgtgaagat    5520 ttacctatcc caggcaccta ccatcgtgga cggacctcag gaccaagcag ggctcagggt    5580
tcctgggcag cccctcctca gaagggtcga ctgctatatg ccccctgtt gttggtggag    5640 gaatctacag tgggtgaagg ataccttggc aaacttggcg gcccactgcg taccttcacc    5700
tgtctgcaag tgcctggagc tcatccgaat cccagccacc gcaagagggg cagtgctgac    5760
agtttggtgg aggctgtgct catctccgaa ggcctaggtc tctttgccca agacccacga    5820
tttgtggccc tggccaagca ggagattgca gatgcatgtc acctgaccct ggatgagatg    5880
gacagtgctg ccagtgacct gctggcacag agaaccatct cccttttacag tgatgaggag    5940 tctattcttt cccgctttga tgaagaggac ctggagatg agatggcctg tgtccatgcc    6000
ctctaaatcc ttacccctca tctactgctc aataaactcc ctgcccttcc ttcccccaga    6060
ggaggcaggc atggaccaca aaaaaaaaaa aaaaaaaaa aaaaaaaaaa aaaa           6114
```

<210> SEQ ID NO 6
<211> LENGTH: 1985
<212> TYPE: PRT
<213> ORGANISM: Mus musculus

<400> SEQUENCE: 6

```
Met Ser Glu Ser Glu Val Gly Lys Asp Thr Thr Pro Glu Pro Ser Pro
1               5                   10                  15

Ala Asn Gly Thr Gly Pro Gly Pro Glu Trp Gly Leu Cys Pro Gly Pro
                20                  25                  30

Pro Thr Val Gly Thr Asp Thr Ser Gly Ala Ser Gly Leu Gly Thr Pro
            35                  40                  45

Arg Arg Arg Thr Gln His Asn Lys His Lys Thr Val Ala Val Ala Ser
        50                  55                  60

Ala Gln Arg Ser Pro Arg Ala Leu Phe Cys Leu Thr Leu Thr Asn Pro
65                  70                  75                  80

Ile Arg Arg Ser Cys Ile Ser Ile Val Glu Trp Lys Pro Phe Asp Ile
                85                  90                  95

Leu Ile Leu Leu Thr Ile Phe Ala Asn Cys Val Ala Leu Gly Val Tyr
            100                 105                 110

Ile Pro Phe Pro Glu Asp Asp Ser Asn Thr Ala Asn His Asn Leu Glu
        115                 120                 125

Gln Val Glu Tyr Val Phe Leu Val Ile Phe Thr Val Glu Thr Val Leu
    130                 135                 140

Lys Ile Val Ala Tyr Gly Leu Val Leu His Pro Ser Ala Tyr Ile Arg
145                 150                 155                 160

Asn Gly Trp Asn Leu Leu Asp Phe Ile Ile Val Val Gly Leu Phe
                165                 170                 175

Ser Val Leu Leu Glu Gln Gly Pro Gly Arg Pro Gly Asp Ala Pro His
            180                 185                 190
```

```
Thr Gly Gly Lys Pro Gly Gly Phe Asp Val Lys Ala Leu Arg Ala Phe
            195                 200                 205
Arg Val Leu Arg Pro Leu Arg Leu Val Ser Gly Val Pro Ser Leu His
    210                 215                 220
Ile Val Val Asn Ser Ile Met Lys Ala Leu Val Pro Leu Leu His Ile
225                 230                 235                 240
Ala Leu Leu Val Leu Phe Val Ile Ile Tyr Ala Ile Ile Gly Leu
            245                 250                 255
Glu Leu Phe Leu Gly Arg Met His Lys Thr Cys Tyr Phe Leu Gly Ser
            260                 265                 270
Asp Met Glu Ala Glu Asp Pro Ser Pro Cys Ala Ser Ser Gly Ser
            275                 280                 285
Gly Arg Ser Cys Thr Leu Asn His Thr Glu Cys Arg Gly Arg Trp Pro
            290                 295                 300
Gly Pro Asn Gly Gly Ile Thr Asn Phe Asp Asn Phe Phe Ala Met
305                 310                 315                 320
Leu Thr Val Phe Gln Cys Ile Thr Met Glu Gly Trp Thr Asp Val Leu
            325                 330                 335
Tyr Trp Met Gln Asp Ala Met Gly Tyr Glu Leu Pro Trp Val Tyr Phe
            340                 345                 350
Val Ser Leu Val Ile Phe Gly Ser Phe Val Leu Asn Leu Val Leu
            355                 360                 365
Gly Val Leu Ser Gly Glu Phe Ser Lys Glu Arg Glu Lys Ala Lys Ala
            370                 375                 380
Arg Gly Asp Phe Gln Lys Leu Arg Glu Lys Gln Gln Met Glu Glu Asp
385                 390                 395                 400
Leu Arg Gly Tyr Leu Asp Trp Ile Thr Gln Ala Glu Glu Leu Asp Leu
            405                 410                 415
His Asp Pro Ser Val Asp Gly Asn Leu Ala Ser Leu Ala Glu Glu Gly
            420                 425                 430
Arg Ala Gly His Arg Pro Gln Leu Ser Glu Leu Thr Asn Arg Arg Arg
            435                 440                 445
Gly Arg Leu Arg Trp Phe Ser His Ser Thr Arg Ser Thr His Ser Thr
            450                 455                 460
Ser Ser His Ala Ser Leu Pro Ala Ser Asp Thr Gly Ser Met Thr Asp
465                 470                 475                 480
Thr Pro Gly Asp Glu Asp Glu Glu Gly Thr Met Ala Ser Cys Thr
            485                 490                 495
Arg Cys Leu Asn Lys Ile Met Lys Thr Arg Ile Cys Arg His Phe Arg
            500                 505                 510
Arg Ala Asn Arg Gly Leu Arg Ala Arg Cys Arg Arg Ala Val Lys Ser
            515                 520                 525
Asn Ala Cys Tyr Trp Ala Val Leu Leu Leu Val Phe Leu Asn Thr Leu
            530                 535                 540
Thr Ile Ala Ser Glu His His Gly Gln Pro Leu Trp Leu Thr Gln Thr
545                 550                 555                 560
Gln Glu Tyr Ala Asn Lys Val Leu Leu Cys Leu Phe Thr Val Glu Met
            565                 570                 575
Leu Leu Lys Leu Tyr Gly Leu Gly Pro Ser Val Tyr Val Ala Ser Phe
            580                 585                 590
Phe Asn Arg Phe Asp Cys Phe Val Val Cys Gly Gly Ile Leu Glu Thr
            595                 600                 605
Thr Leu Val Glu Val Gly Ala Met Gln Pro Leu Gly Ile Ser Val Leu
```

```
            610             615             620
Arg Cys Val Arg Leu Leu Arg Ile Phe Lys Val Thr Arg His Trp Ala
625             630             635             640

Ser Leu Ser Asn Leu Val Ala Ser Leu Leu Asn Ser Met Lys Ser Ile
                645             650             655

Ala Ser Leu Leu Leu Leu Leu Phe Leu Phe Ile Ile Ile Phe Ser Leu
            660             665             670

Leu Gly Met Gln Leu Phe Gly Gly Lys Phe Asn Phe Asp Gln Thr His
            675             680             685

Thr Lys Arg Ser Thr Phe Asp Thr Phe Pro Gln Ala Leu Leu Thr Val
690             695             700

Phe Gln Ile Leu Thr Gly Glu Asp Trp Asn Val Val Met Tyr Asp Gly
705             710             715             720

Ile Met Ala Tyr Gly Gly Pro Phe Phe Pro Gly Met Leu Val Cys Val
            725             730             735

Tyr Phe Ile Ile Leu Phe Ile Cys Gly Asn Tyr Ile Leu Leu Asn Val
            740             745             750

Phe Leu Ala Ile Ala Val Asp Asn Leu Ala Ser Gly Asp Ala Gly Thr
            755             760             765

Ala Lys Asp Lys Gly Arg Glu Lys Ser Ser Glu Gly Asn Pro Pro Lys
770             775             780

Glu Asn Lys Val Leu Val Pro Gly Gly Glu Asn Glu Asp Ala Lys Gly
785             790             795             800

Ala Arg Ser Glu Gly Ala Ala Pro Gly Met Glu Glu Glu Glu Glu
            805             810             815

Glu Glu Glu Glu Glu Glu Glu Glu Glu Glu Glu Glu Asn Gly Ala
            820             825             830

Gly His Val Glu Leu Leu Gln Glu Val Val Pro Lys Glu Lys Val Val
            835             840             845

Pro Ile Pro Glu Gly Ser Ala Phe Phe Cys Leu Ser Gln Thr Asn Pro
850             855             860

Leu Arg Lys Ala Cys His Thr Leu Ile His His Ile Phe Thr Ser
865             870             875             880

Leu Ile Leu Val Phe Ile Ile Leu Ser Ser Val Ser Leu Ala Ala Glu
            885             890             895

Asp Pro Ile Arg Ala His Ser Phe Arg Asn His Ile Leu Gly Tyr Phe
            900             905             910

Asp Tyr Ala Phe Thr Ser Ile Phe Thr Val Glu Ile Leu Leu Lys Met
            915             920             925

Thr Val Phe Gly Ala Phe Leu His Arg Gly Ser Phe Cys Arg Ser Trp
930             935             940

Phe Asn Leu Leu Asp Leu Leu Val Val Ser Val Ser Leu Ile Ser Phe
945             950             955             960

Gly Ile His Ser Ser Ala Ile Ser Val Val Lys Ile Leu Arg Val Leu
            965             970             975

Arg Val Leu Arg Pro Leu Arg Ala Ile Asn Arg Ala Lys Gly Leu Lys
            980             985             990

His Val Val Gln Cys Val Phe Val Ala Ile Arg Thr Ile Gly Asn Ile
            995             1000            1005

Met Ile Val Thr Thr Leu Leu Gln Phe Met Phe Ala Cys Ile Gly
            1010            1015            1020

Val Gln Leu Phe Lys Gly Lys Phe Tyr Ser Cys Thr Asp Glu Ala
            1025            1030            1035
```

-continued

```
Lys His Thr Leu Lys Glu Ser Lys Gly Ser Phe Leu Ile Tyr Pro
    1040                1045                1050

Asp Gly Asp Val Ser Arg Pro Leu Val Arg Glu Arg Leu Trp Val
    1055                1060                1065

Asn Ser Asp Phe Asn Phe Asp Asn Val Leu Ser Ala Met Met Ala
    1070                1075                1080

Leu Phe Thr Val Ser Thr Phe Glu Gly Trp Pro Ala Leu Leu Tyr
    1085                1090                1095

Lys Ala Ile Asp Ala Asn Ala Glu Asp Glu Gly Pro Ile Tyr Asn
    1100                1105                1110

Tyr His Val Glu Ile Ser Val Phe Phe Ile Val Tyr Ile Ile Ile
    1115                1120                1125

Ile Ala Phe Phe Met Met Asn Ile Phe Val Gly Phe Val Ile Ile
    1130                1135                1140

Thr Phe Arg Ala Gln Gly Gln Glu Tyr Gln Asn Cys Glu Leu
    1145                1150                1155

Asp Lys Asn Gln Arg Gln Cys Val Glu Tyr Ala Leu Lys Ala Gln
    1160                1165                1170

Pro Leu Arg Arg Tyr Ile Pro Lys Asn Pro His Gln Tyr Arg Val
    1175                1180                1185

Trp Ala Thr Val Asn Ser Arg Ala Phe Glu Tyr Leu Met Phe Leu
    1190                1195                1200

Leu Ile Leu Leu Asn Thr Val Ala Leu Ala Met Gln His Tyr Glu
    1205                1210                1215

Gln Thr Ala Pro Phe Asn Tyr Ala Met Asp Ile Leu Asn Met Val
    1220                1225                1230

Phe Thr Gly Leu Phe Thr Ile Glu Met Val Leu Lys Ile Ile Ala
    1235                1240                1245

Phe Lys Pro Lys His Tyr Phe Ala Asp Ala Trp Asn Thr Phe Asp
    1250                1255                1260

Ala Leu Ile Val Val Gly Ser Val Val Asp Ile Ala Val Thr Glu
    1265                1270                1275

Val Asn Asn Gly Gly His Leu Gly Glu Ser Ser Glu Asp Thr Ser
    1280                1285                1290

Arg Ile Ser Ile Thr Phe Phe Arg Leu Phe Arg Val Met Arg Leu
    1295                1300                1305

Val Lys Leu Leu Ser Lys Gly Glu Gly Ile Arg Thr Leu Leu Trp
    1310                1315                1320

Thr Phe Ile Lys Ser Phe Gln Ala Leu Pro Tyr Val Ala Leu Leu
    1325                1330                1335

Ile Ala Met Ile Phe Phe Ile Tyr Ala Val Ile Gly Met Gln Met
    1340                1345                1350

Phe Gly Leu Val Ala Leu Gln Asp Gly Thr Gln Ile Asn Arg Asn
    1355                1360                1365

Asn Asn Phe Gln Thr Phe Pro Gln Ala Val Leu Leu Leu Phe Arg
    1370                1375                1380

Cys Ala Thr Gly Glu Ala Trp Gln Glu Ile Met Leu Ala Ser Leu
    1385                1390                1395

Pro Gly Asn Arg Cys Asp Pro Glu Ser Asp Phe Gly Pro Gly Glu
    1400                1405                1410

Glu Phe Thr Cys Gly Ser Ser Phe Ala Ile Val Tyr Phe Ile Ser
    1415                1420                1425
```

```
Phe Phe Met Leu Cys Ala Phe Leu Ile Ile Asn Leu Phe Val Ala
        1430                1435                1440

Val Ile Met Asp Asn Phe Asp Tyr Leu Thr Arg Asp Trp Ser Ile
        1445                1450                1455

Leu Gly Pro His His Leu Asp Glu Phe Lys Arg Ile Trp Ser Glu
        1460                1465                1470

Tyr Asp Pro Gly Ala Lys Gly Arg Ile Lys His Leu Asp Val Val
        1475                1480                1485

Ala Leu Leu Arg Arg Ile Gln Pro Pro Leu Gly Phe Gly Lys Leu
        1490                1495                1500

Cys Pro His Arg Val Ala Cys Lys Arg Leu Val Ala Met Asn Val
        1505                1510                1515

Pro Leu Asn Ser Asp Gly Thr Val Thr Phe Asn Ala Thr Leu Phe
        1520                1525                1530

Ala Leu Val Arg Thr Ser Leu Lys Ile Lys Thr Glu Gly Asn Leu
        1535                1540                1545

Asp Gln Ala Asn Gln Glu Leu Arg Met Val Ile Lys Lys Ile Trp
        1550                1555                1560

Lys Arg Ile Lys Gln Lys Leu Leu Asp Glu Val Ile Pro Pro Pro
        1565                1570                1575

Asp Glu Glu Glu Val Thr Val Gly Lys Phe Tyr Ala Thr Phe Leu
        1580                1585                1590

Ile Gln Asp Tyr Phe Arg Lys Phe Arg Arg Arg Lys Glu Lys Gly
        1595                1600                1605

Leu Leu Gly Arg Glu Ala Pro Thr Ser Thr Ser Ser Ala Leu Gln
        1610                1615                1620

Ala Gly Leu Arg Ser Leu Gln Asp Leu Gly Pro Glu Ile Arg Gln
        1625                1630                1635

Ala Leu Thr Tyr Val Thr Glu Glu Glu Glu Glu Glu Glu Glu Ala
        1640                1645                1650

Val Gly Gln Glu Ala Glu Glu Glu Ala Glu Asn Asn Pro Glu
        1655                1660                1665

Pro Tyr Lys Asp Ser Ile Asp Ser Gln Pro Gln Ser Arg Trp Asn
        1670                1675                1680

Ser Arg Ile Ser Val Ser Leu Pro Val Lys Glu Lys Leu Pro Asp
        1685                1690                1695

Ser Leu Ser Thr Gly Pro Ser Asp Asp Asp Gly Leu Ala Pro Asn
        1700                1705                1710

Ser Arg Gln Pro Ser Val Ile Gln Ala Gly Ser Gln Pro His Arg
        1715                1720                1725

Arg Ser Ser Gly Val Phe Met Phe Thr Ile Pro Glu Glu Gly Ser
        1730                1735                1740

Ile Gln Leu Lys Gly Thr Gln Gly Gln Asp Asn Gln Asn Glu Glu
        1745                1750                1755

Gln Glu Leu Pro Asp Trp Thr Pro Asp Leu Asp Arg Ala Gly Arg
        1760                1765                1770

Asp Ser Phe Glu Pro Ser Pro Phe Thr Thr Ser Leu Val Gln Gln
        1775                1780                1785

His Val Asn Gly His Met Ser Thr Pro Thr Phe Ala Ala Pro His
        1790                1795                1800

Ala Cys Arg Ser Glu Pro Ser Phe Thr Ile Gln Cys Leu Gln Arg
        1805                1810                1815

Leu Gly Ser Cys Glu Asp Leu Pro Ile Pro Gly Thr Tyr His Arg
```

```
         1820               1825                1830
Gly Arg Thr Ser Gly Pro Ser Arg Ala Gln Gly Ser Trp Ala Ala
    1835               1840                1845

Pro Pro Gln Lys Gly Arg Leu Leu Tyr Ala Pro Leu Leu Leu Val
    1850               1855                1860

Glu Glu Ser Thr Val Gly Glu Gly Tyr Leu Gly Lys Leu Gly Gly
    1865               1870                1875

Pro Leu Arg Thr Phe Thr Cys Leu Gln Val Pro Gly Ala His Pro
    1880               1885                1890

Asn Pro Ser His Arg Lys Arg Gly Ser Ala Asp Ser Leu Val Glu
    1895               1900                1905

Ala Val Leu Ile Ser Glu Gly Leu Gly Leu Phe Ala Gln Asp Pro
    1910               1915                1920

Arg Phe Val Ala Leu Ala Lys Gln Glu Ile Ala Asp Ala Cys His
    1925               1930                1935

Leu Thr Leu Asp Glu Met Asp Ser Ala Ala Ser Asp Leu Leu Ala
    1940               1945                1950

Gln Arg Thr Ile Ser Leu Tyr Ser Asp Glu Glu Ser Ile Leu Ser
    1955               1960                1965

Arg Phe Asp Glu Glu Asp Leu Gly Asp Glu Met Ala Cys Val His
    1970               1975                1980

Ala Leu
    1985

<210> SEQ ID NO 7
<211> LENGTH: 20
<212> TYPE: DNA
<213> ORGANISM: homo sapiens

<400> SEQUENCE: 7
tttctctctg tctaccttgt                                           20

<210> SEQ ID NO 8
<211> LENGTH: 21
<212> TYPE: DNA
<213> ORGANISM: homo sapiens

<400> SEQUENCE: 8
ctgcgggctc ccttactact g                                         21

<210> SEQ ID NO 9
<211> LENGTH: 20
<212> TYPE: DNA
<213> ORGANISM: Mus musculus

<400> SEQUENCE: 9
atctggtggc atctttgctc                                           20

<210> SEQ ID NO 10
<211> LENGTH: 20
<212> TYPE: DNA
<213> ORGANISM: Mus musculus

<400> SEQUENCE: 10
agcagccagg gacacactac                                           20

<210> SEQ ID NO 11
<211> LENGTH: 20
<212> TYPE: DNA
```

-continued

<213> ORGANISM: Mus musculus

<400> SEQUENCE: 11
ggcgagagtt cagaggacag                                              20

<210> SEQ ID NO 12
<211> LENGTH: 20
<212> TYPE: DNA
<213> ORGANISM: Mus musculus

<400> SEQUENCE: 12
ccacatccaa gtgttgatgc                                              20

<210> SEQ ID NO 13
<211> LENGTH: 18
<212> TYPE: DNA
<213> ORGANISM: Mus musculus

<400> SEQUENCE: 13
ggatcaagcc aaccagga                                                18

<210> SEQ ID NO 14
<211> LENGTH: 18
<212> TYPE: DNA
<213> ORGANISM: Mus musculus

<400> SEQUENCE: 14
ctttggttcc cttgggct                                                18

<210> SEQ ID NO 15
<211> LENGTH: 20
<212> TYPE: DNA
<213> ORGANISM: Mus musculus

<400> SEQUENCE: 15
ttccggagaa ggaaagaaaa                                              20

<210> SEQ ID NO 16
<211> LENGTH: 19
<212> TYPE: DNA
<213> ORGANISM: Mus musculus

<400> SEQUENCE: 16
cacaaatcgt gggtcttgg                                               19

<210> SEQ ID NO 17
<211> LENGTH: 20
<212> TYPE: DNA
<213> ORGANISM: Mus musculus

<400> SEQUENCE: 17
actcaagatg acagtgtttg                                              20

<210> SEQ ID NO 18
<211> LENGTH: 20
<212> TYPE: DNA
<213> ORGANISM: Mus musculus

<400> SEQUENCE: 18
cctggtttcc agcactgtgt                                              20

<210> SEQ ID NO 19
<211> LENGTH: 20

```
<212> TYPE: DNA
<213> ORGANISM: Mus musculus

<400> SEQUENCE: 19
actgaaccat accgagtgcc                                              20

<210> SEQ ID NO 20
<211> LENGTH: 20
<212> TYPE: DNA
<213> ORGANISM: Mus musculus

<400> SEQUENCE: 20
tcagcctgtg tgatccagtc                                              20

<210> SEQ ID NO 21
<211> LENGTH: 20
<212> TYPE: DNA
<213> ORGANISM: Mus musculus

<400> SEQUENCE: 21
atgaaaacaa ggatctgccg                                              20

<210> SEQ ID NO 22
<211> LENGTH: 20
<212> TYPE: DNA
<213> ORGANISM: Mus musculus

<400> SEQUENCE: 22
gagacgtaca catcggagca                                              20

<210> SEQ ID NO 23
<211> LENGTH: 18
<212> TYPE: DNA
<213> ORGANISM: Mus musculus

<400> SEQUENCE: 23
acacaggaga agctctgg                                                18

<210> SEQ ID NO 24
<211> LENGTH: 17
<212> TYPE: DNA
<213> ORGANISM: Mus musculus

<400> SEQUENCE: 24
cacctcactg gtcagca                                                 17

<210> SEQ ID NO 25
<211> LENGTH: 25
<212> TYPE: DNA
<213> ORGANISM: Mus musculus

<400> SEQUENCE: 25
catggcatcc tgcatccagt agagg                                        25

<210> SEQ ID NO 26
<211> LENGTH: 26
<212> TYPE: DNA
<213> ORGANISM: Mus musculus

<400> SEQUENCE: 26
gtccgaggaa tagctcgagt ccgatg                                       26

<210> SEQ ID NO 27
```

```
<211> LENGTH: 26
<212> TYPE: DNA
<213> ORGANISM: Mus musculus

<400> SEQUENCE: 27
ctcccaacca cacaggagaa gctctg                                          26

<210> SEQ ID NO 28
<211> LENGTH: 26
<212> TYPE: DNA
<213> ORGANISM: Mus musculus

<400> SEQUENCE: 28
cccctgttgt tggtggagga atctac                                          26

<210> SEQ ID NO 29
<211> LENGTH: 20
<212> TYPE: DNA
<213> ORGANISM: homo sapiens

<400> SEQUENCE: 29
gagaatcctt ccatccctgc                                                 20

<210> SEQ ID NO 30
<211> LENGTH: 20
<212> TYPE: DNA
<213> ORGANISM: Homo sapiens

<400> SEQUENCE: 30
attcgtccaa ggaacagctc                                                 20

<210> SEQ ID NO 31
<211> LENGTH: 20
<212> TYPE: DNA
<213> ORGANISM: Homo sapiens

<400> SEQUENCE: 31
gtggagacgg tgctcaagat                                                 20

<210> SEQ ID NO 32
<211> LENGTH: 20
<212> TYPE: DNA
<213> ORGANISM: Homo sapiens

<400> SEQUENCE: 32
attcgtccaa ggaacagctc                                                 20

<210> SEQ ID NO 33
<211> LENGTH: 19
<212> TYPE: DNA
<213> ORGANISM: Homo sapiens

<400> SEQUENCE: 33
tcgtgctctc gtcatcatc                                                  19

<210> SEQ ID NO 34
<211> LENGTH: 20
<212> TYPE: DNA
<213> ORGANISM: Homo sapiens

<400> SEQUENCE: 34
tggagtgtgt ggagcgagta                                                 20
```

-continued

```
<210> SEQ ID NO 35
<211> LENGTH: 19
<212> TYPE: DNA
<213> ORGANISM: Homo sapiens

<400> SEQUENCE: 35
accaatagga ggcgtggac                                                 19

<210> SEQ ID NO 36
<211> LENGTH: 20
<212> TYPE: DNA
<213> ORGANISM: Homo sapiens

<400> SEQUENCE: 36
ggtgtgggtc tggtcaaagt                                                20

<210> SEQ ID NO 37
<211> LENGTH: 21
<212> TYPE: DNA
<213> ORGANISM: Homo sapiens

<400> SEQUENCE: 37
ttctcctctt cctctcatca t                                              21

<210> SEQ ID NO 38
<211> LENGTH: 19
<212> TYPE: DNA
<213> ORGANISM: Homo sapiens

<400> SEQUENCE: 38
ggtttggctg aggcagaag                                                 19

<210> SEQ ID NO 39
<211> LENGTH: 20
<212> TYPE: DNA
<213> ORGANISM: Homo sapiens

<400> SEQUENCE: 39
tgtacccaag gagaaggtgg                                                20

<210> SEQ ID NO 40
<211> LENGTH: 20
<212> TYPE: DNA
<213> ORGANISM: Homo sapiens

<400> SEQUENCE: 40
aagtgatgat gacgaagccc                                                20

<210> SEQ ID NO 41
<211> LENGTH: 20
<212> TYPE: DNA
<213> ORGANISM: Homo sapiens

<400> SEQUENCE: 41
ccatctcggt ggtgaagatt                                                20

<210> SEQ ID NO 42
<211> LENGTH: 19
<212> TYPE: DNA
<213> ORGANISM: Homo sapiens

<400> SEQUENCE: 42
cggatccctt caccctact                                                 19
```

-continued

<210> SEQ ID NO 43
<211> LENGTH: 22
<212> TYPE: DNA
<213> ORGANISM: Homo sapiens

<400> SEQUENCE: 43
taccgtgtgg agatctcagt gt                                              22

<210> SEQ ID NO 44
<211> LENGTH: 22
<212> TYPE: DNA
<213> ORGANISM: Homo sapiens

<400> SEQUENCE: 44
caaccacatc caagtgtttg at                                              22

<210> SEQ ID NO 45
<211> LENGTH: 22
<212> TYPE: DNA
<213> ORGANISM: Homo sapiens

<400> SEQUENCE: 45
gcatttccat taccttcttt cg                                              22

<210> SEQ ID NO 46
<211> LENGTH: 22
<212> TYPE: DNA
<213> ORGANISM: Homo sapiens

<400> SEQUENCE: 46
caaccacatc caagtgtttg at                                              22

<210> SEQ ID NO 47
<211> LENGTH: 19
<212> TYPE: DNA
<213> ORGANISM: Homo sapiens

<400> SEQUENCE: 47
caccagagat ggtccatcc                                                  19

<210> SEQ ID NO 48
<211> LENGTH: 20
<212> TYPE: DNA
<213> ORGANISM: Homo sapiens

<400> SEQUENCE: 48
ggggatgacc tcatctagca                                                 20

<210> SEQ ID NO 49
<211> LENGTH: 23
<212> TYPE: DNA
<213> ORGANISM: Homo sapiens

<400> SEQUENCE: 49
tgaaaaggac tggaaactaa caa                                             23

<210> SEQ ID NO 50
<211> LENGTH: 19
<212> TYPE: DNA
<213> ORGANISM: Homo sapiens

<400> SEQUENCE: 50
gccatctcgt ctcccaagt                                                  19

<210> SEQ ID NO 51
<211> LENGTH: 20
<212> TYPE: DNA
<213> ORGANISM: Homo sapiens

<400> SEQUENCE: 51
ccaccctccc atacaacact                                               20

<210> SEQ ID NO 52
<211> LENGTH: 19
<212> TYPE: DNA
<213> ORGANISM: Homo sapiens

<400> SEQUENCE: 52
gtgattggtt cttgtcccc                                                19

<210> SEQ ID NO 53
<211> LENGTH: 20
<212> TYPE: DNA
<213> ORGANISM: Homo sapiens

<400> SEQUENCE: 53
gatcaggtag gaagcagcca                                               20

<210> SEQ ID NO 54
<211> LENGTH: 20
<212> TYPE: DNA
<213> ORGANISM: Homo sapiens

<400> SEQUENCE: 54
ctcctggtac cctgatgacc                                               20

<210> SEQ ID NO 55
<211> LENGTH: 20
<212> TYPE: DNA
<213> ORGANISM: Homo sapiens

<400> SEQUENCE: 55
gaggttccca agggagtagg                                               20

<210> SEQ ID NO 56
<211> LENGTH: 20
<212> TYPE: DNA
<213> ORGANISM: Homo sapiens

<400> SEQUENCE: 56
gtctggctgg aaggagtgag                                               20

<210> SEQ ID NO 57
<211> LENGTH: 20
<212> TYPE: DNA
<213> ORGANISM: Homo sapiens

<400> SEQUENCE: 57
ctcggtcctg actatgctcc                                               20

<210> SEQ ID NO 58
<211> LENGTH: 20
<212> TYPE: DNA
<213> ORGANISM: Homo sapiens

<400> SEQUENCE: 58
ggtaggaagg cgactagggt                                              20

<210> SEQ ID NO 59
<211> LENGTH: 18
<212> TYPE: DNA
<213> ORGANISM: Homo sapiens

<400> SEQUENCE: 59
atcccaaggc ctgacctc                                                18

<210> SEQ ID NO 60
<211> LENGTH: 18
<212> TYPE: DNA
<213> ORGANISM: Homo sapiens

<400> SEQUENCE: 60
accctccacc tccgacct                                                18

<210> SEQ ID NO 61
<211> LENGTH: 20
<212> TYPE: DNA
<213> ORGANISM: Homo sapiens

<400> SEQUENCE: 61
ctgaccccgc ccttatttct                                              20

<210> SEQ ID NO 62
<211> LENGTH: 20
<212> TYPE: DNA
<213> ORGANISM: Homo sapiens

<400> SEQUENCE: 62
agcattggat ctaggaaccg                                              20

<210> SEQ ID NO 63
<211> LENGTH: 19
<212> TYPE: DNA
<213> ORGANISM: Homo sapiens

<400> SEQUENCE: 63
actgagagtg ggcctgctt                                               19

<210> SEQ ID NO 64
<211> LENGTH: 19
<212> TYPE: DNA
<213> ORGANISM: Homo sapiens

<400> SEQUENCE: 64
gtgcagcctt gagctctgt                                               19

<210> SEQ ID NO 65
<211> LENGTH: 20
<212> TYPE: DNA
<213> ORGANISM: Homo sapiens

<400> SEQUENCE: 65
ggatgcatgc cttttctctc                                              20

<210> SEQ ID NO 66
<211> LENGTH: 20
<212> TYPE: DNA
<213> ORGANISM: Homo sapiens

<400> SEQUENCE: 66
gtttgccagg cacaaagaag 20

<210> SEQ ID NO 67
<211> LENGTH: 20
<212> TYPE: DNA
<213> ORGANISM: Homo sapiens

<400> SEQUENCE: 67
tgtggctgga gtgatgaaag 20

<210> SEQ ID NO 68
<211> LENGTH: 20
<212> TYPE: DNA
<213> ORGANISM: Homo sapiens

<400> SEQUENCE: 68
ggagggcaga ccacatctaa 20

<210> SEQ ID NO 69
<211> LENGTH: 20
<212> TYPE: DNA
<213> ORGANISM: Homo sapiens

<400> SEQUENCE: 69
aattgtcctt ctctccctgc 20

<210> SEQ ID NO 70
<211> LENGTH: 18
<212> TYPE: DNA
<213> ORGANISM: Homo sapiens

<400> SEQUENCE: 70
cagcctggct ggacccccc 18

<210> SEQ ID NO 71
<211> LENGTH: 20
<212> TYPE: DNA
<213> ORGANISM: Homo sapiens

<400> SEQUENCE: 71
aggtcctgac cactatcccc 20

<210> SEQ ID NO 72
<211> LENGTH: 20
<212> TYPE: DNA
<213> ORGANISM: Homo sapiens

<400> SEQUENCE: 72
ggacttgagt cagggtttgg 20

<210> SEQ ID NO 73
<211> LENGTH: 20
<212> TYPE: DNA
<213> ORGANISM: Homo sapiens

<400> SEQUENCE: 73
tttacgacac acacctccca 20

<210> SEQ ID NO 74
<211> LENGTH: 20
<212> TYPE: DNA
<213> ORGANISM: Homo sapiens -continued

```
<400> SEQUENCE: 74
cacctaccta agcctgccct                                                   20

<210> SEQ ID NO 75
<211> LENGTH: 20
<212> TYPE: DNA
<213> ORGANISM: Homo sapiens

<400> SEQUENCE: 75
agggcaggct taggtaggtg                                                   20

<210> SEQ ID NO 76
<211> LENGTH: 20
<212> TYPE: DNA
<213> ORGANISM: Homo sapiens

<400> SEQUENCE: 76
agaaggaata ggaggctggg                                                   20

<210> SEQ ID NO 77
<211> LENGTH: 20
<212> TYPE: DNA
<213> ORGANISM: Homo sapiens

<400> SEQUENCE: 77
gatcatccct gcctctctcc                                                   20

<210> SEQ ID NO 78
<211> LENGTH: 20
<212> TYPE: DNA
<213> ORGANISM: Homo sapiens

<400> SEQUENCE: 78
cttccccctc ccctaataca                                                   20

<210> SEQ ID NO 79
<211> LENGTH: 18
<212> TYPE: DNA
<213> ORGANISM: Homo sapiens

<400> SEQUENCE: 79
agcctamgag cccaacct                                                     18

<210> SEQ ID NO 80
<211> LENGTH: 18
<212> TYPE: DNA
<213> ORGANISM: Homo sapiens

<400> SEQUENCE: 80
acccatccca tggtctcc                                                     18

<210> SEQ ID NO 81
<211> LENGTH: 20
<212> TYPE: DNA
<213> ORGANISM: Homo sapiens

<400> SEQUENCE: 81
gagctccaca gtgacttccc                                                   20

<210> SEQ ID NO 82
<211> LENGTH: 20
<212> TYPE: DNA
<213> ORGANISM: Homo sapiens
```

<400> SEQUENCE: 82
accctgccta tagaccaccc                    20

<210> SEQ ID NO 83
<211> LENGTH: 20
<212> TYPE: DNA
<213> ORGANISM: Homo sapiens

<400> SEQUENCE: 83
gtggtctata ggcagggtgc                    20

<210> SEQ ID NO 84
<211> LENGTH: 19
<212> TYPE: DNA
<213> ORGANISM: Homo sapiens

<400> SEQUENCE: 84
gactgtgtag gggtggagc                     19

<210> SEQ ID NO 85
<211> LENGTH: 20
<212> TYPE: DNA
<213> ORGANISM: Homo sapiens

<400> SEQUENCE: 85
atgggaccca agaaaggtct                    20

<210> SEQ ID NO 86
<211> LENGTH: 19
<212> TYPE: DNA
<213> ORGANISM: Homo sapiens

<400> SEQUENCE: 86
gtgggatggg aggtgtaga                     19

<210> SEQ ID NO 87
<211> LENGTH: 19
<212> TYPE: DNA
<213> ORGANISM: Homo sapiens

<400> SEQUENCE: 87
cctcaccatg atgactccc                     19

<210> SEQ ID NO 88
<211> LENGTH: 17
<212> TYPE: DNA
<213> ORGANISM: Homo sapiens

<400> SEQUENCE: 88
tgtctgccga gctcmcc                       17

<210> SEQ ID NO 89
<211> LENGTH: 20
<212> TYPE: DNA
<213> ORGANISM: Homo sapiens

<400> SEQUENCE: 89
caaacactgt tctgggtgct                    20

<210> SEQ ID NO 90
<211> LENGTH: 19
<212> TYPE: DNA

<213> ORGANISM: Homo sapiens

<400> SEQUENCE: 90
ctcctccatg ctcctccac                                                     19

<210> SEQ ID NO 91
<211> LENGTH: 20
<212> TYPE: DNA
<213> ORGANISM: Homo sapiens

<400> SEQUENCE: 91
tcagggccag aactgtatcc                                                    20

<210> SEQ ID NO 92
<211> LENGTH: 20
<212> TYPE: DNA
<213> ORGANISM: Homo sapiens

<400> SEQUENCE: 92
gtcccctcag ctcctagctc                                                    20

<210> SEQ ID NO 93
<211> LENGTH: 18
<212> TYPE: DNA
<213> ORGANISM: Homo sapiens

<400> SEQUENCE: 93
ctccccgctc tttcacac                                                      18

<210> SEQ ID NO 94
<211> LENGTH: 19
<212> TYPE: DNA
<213> ORGANISM: Homo sapiens

<400> SEQUENCE: 94
gactggggtc ccatagtca                                                     19

<210> SEQ ID NO 95
<211> LENGTH: 20
<212> TYPE: DNA
<213> ORGANISM: Homo sapiens

<400> SEQUENCE: 95
tccccaggtc tgagtctagc                                                    20

<210> SEQ ID NO 96
<211> LENGTH: 18
<212> TYPE: DNA
<213> ORGANISM: Homo sapiens

<400> SEQUENCE: 96
gtcctgtggg tttgggtg                                                      18

<210> SEQ ID NO 97
<211> LENGTH: 20
<212> TYPE: DNA
<213> ORGANISM: Homo sapiens

<400> SEQUENCE: 97
gtagccatat gcttgggtgc                                                    20

<210> SEQ ID NO 98
<211> LENGTH: 18

```
<212> TYPE: DNA
<213> ORGANISM: Homo sapiens

<400> SEQUENCE: 98
agtcttggga ggggtcct                                               18

<210> SEQ ID NO 99
<211> LENGTH: 20
<212> TYPE: DNA
<213> ORGANISM: Homo sapiens

<400> SEQUENCE: 99
agttcctcac ccctcctcac                                             20

<210> SEQ ID NO 100
<211> LENGTH: 20
<212> TYPE: DNA
<213> ORGANISM: Homo sapiens

<400> SEQUENCE: 100
ctgcctcatc ccctgataaa                                             20

<210> SEQ ID NO 101
<211> LENGTH: 19
<212> TYPE: DNA
<213> ORGANISM: Homo sapiens

<400> SEQUENCE: 101
atttaggggt cttggggtg                                              19

<210> SEQ ID NO 102
<211> LENGTH: 20
<212> TYPE: DNA
<213> ORGANISM: Homo sapiens

<400> SEQUENCE: 102
gcagccttaa atgttcccaa                                             20

<210> SEQ ID NO 103
<211> LENGTH: 19
<212> TYPE: DNA
<213> ORGANISM: Homo sapiens

<400> SEQUENCE: 103
cagtgcaaga ggttgacca                                              19

<210> SEQ ID NO 104
<211> LENGTH: 20
<212> TYPE: DNA
<213> ORGANISM: Homo sapiens

<400> SEQUENCE: 104
cccaaggaat tcatccactg                                             20

<210> SEQ ID NO 105
<211> LENGTH: 20
<212> TYPE: DNA
<213> ORGANISM: Homo sapiens

<400> SEQUENCE: 105
gctttgagaa gacagggcac                                             20

<210> SEQ ID NO 106
```

```
<211> LENGTH: 20
<212> TYPE: DNA
<213> ORGANISM: Homo sapiens

<400> SEQUENCE: 106
gaaagccagt agaggggac                                              20

<210> SEQ ID NO 107
<211> LENGTH: 20
<212> TYPE: DNA
<213> ORGANISM: Homo sapiens

<400> SEQUENCE: 107
gtaatgaccc caccatcacc                                             20

<210> SEQ ID NO 108
<211> LENGTH: 20
<212> TYPE: DNA
<213> ORGANISM: Homo sapiens

<400> SEQUENCE: 108
cagagggaca tgggaaaaga                                             20

<210> SEQ ID NO 109
<211> LENGTH: 20
<212> TYPE: DNA
<213> ORGANISM: Homo sapiens

<400> SEQUENCE: 109
aaatgcaaac tgagcatccc                                             20

<210> SEQ ID NO 110
<211> LENGTH: 18
<212> TYPE: DNA
<213> ORGANISM: Homo sapiens

<400> SEQUENCE: 110
amggaaatgg gtatggca                                               18

<210> SEQ ID NO 111
<211> LENGTH: 20
<212> TYPE: DNA
<213> ORGANISM: Homo sapiens

<400> SEQUENCE: 111
gactgcatct cccagtaggc                                             20

<210> SEQ ID NO 112
<211> LENGTH: 20
<212> TYPE: DNA
<213> ORGANISM: Homo sapiens

<400> SEQUENCE: 112
attcttaacc catcccctgc                                             20

<210> SEQ ID NO 113
<211> LENGTH: 20
<212> TYPE: DNA
<213> ORGANISM: Homo sapiens

<400> SEQUENCE: 113 gtagggtgg caggtagaca                                              20
```

```
<210> SEQ ID NO 114
<211> LENGTH: 20
<212> TYPE: DNA
<213> ORGANISM: Homo sapiens

<400> SEQUENCE: 114
gtggcagggg agtgagtaga                                              20

<210> SEQ ID NO 115
<211> LENGTH: 20
<212> TYPE: DNA
<213> ORGANISM: Homo sapiens

<400> SEQUENCE: 115
gatgtagccc ctggtgagaa                                              20

<210> SEQ ID NO 116
<211> LENGTH: 19
<212> TYPE: DNA
<213> ORGANISM: Homo sapiens

<400> SEQUENCE: 116
ggtggtgtga ggaaatggt                                               19

<210> SEQ ID NO 117
<211> LENGTH: 20
<212> TYPE: DNA
<213> ORGANISM: Homo sapiens

<400> SEQUENCE: 117
acagtgttct gcccttcacc                                              20

<210> SEQ ID NO 118
<211> LENGTH: 20
<212> TYPE: DNA
<213> ORGANISM: Homo sapiens

<400> SEQUENCE: 118
aactggaggg cagtcagaga                                              20

<210> SEQ ID NO 119
<211> LENGTH: 20
<212> TYPE: DNA
<213> ORGANISM: Homo sapiens

<400> SEQUENCE: 119
cagtggtacc tccccaactc                                              20

<210> SEQ ID NO 120
<211> LENGTH: 20
<212> TYPE: DNA
<213> ORGANISM: Homo sapiens

<400> SEQUENCE: 120
agaaacctct gaggatgcga                                              20

<210> SEQ ID NO 121
<211> LENGTH: 20
<212> TYPE: DNA
<213> ORGANISM: Homo sapiens

<400> SEQUENCE: 121
acattcgttc ctgcataccc                                              20
```

```
<210> SEQ ID NO 122
<211> LENGTH: 18
<212> TYPE: DNA
<213> ORGANISM: Homo sapiens

<400> SEQUENCE: 122
atgagmgctc cttgcacc                                                 18

<210> SEQ ID NO 123
<211> LENGTH: 20
<212> TYPE: DNA
<213> ORGANISM: Homo sapiens

<400> SEQUENCE: 123
tcttcctatt ggctcatgcc                                               20

<210> SEQ ID NO 124
<211> LENGTH: 18
<212> TYPE: DNA
<213> ORGANISM: Homo sapiens

<400> SEQUENCE: 124
ggggcctcag mccttatc                                                 18

<210> SEQ ID NO 125
<211> LENGTH: 20
<212> TYPE: DNA
<213> ORGANISM: Homo sapiens

<400> SEQUENCE: 125
acctatttct ccaccccac                                                20

<210> SEQ ID NO 126
<211> LENGTH: 20
<212> TYPE: DNA
<213> ORGANISM: Homo sapiens

<400> SEQUENCE: 126
gcttcttccc agaagcagtg                                               20

<210> SEQ ID NO 127
<211> LENGTH: 20
<212> TYPE: DNA
<213> ORGANISM: Homo sapiens

<400> SEQUENCE: 127
gtgcatgcaa cactcagtcc                                               20

<210> SEQ ID NO 128
<211> LENGTH: 20
<212> TYPE: DNA
<213> ORGANISM: Homo sapiens

<400> SEQUENCE: 128
ctcaacttcc tgcctcctga                                               20

<210> SEQ ID NO 129
<211> LENGTH: 20
<212> TYPE: DNA
<213> ORGANISM: Homo sapiens

<400> SEQUENCE: 129
atctggtctg cctaacgtgc                                               20
```

<210> SEQ ID NO 130
<211> LENGTH: 20
<212> TYPE: DNA
<213> ORGANISM: Homo sapiens

<400> SEQUENCE: 130
gagatggggc acaaacagtc                                            20

<210> SEQ ID NO 131
<211> LENGTH: 20
<212> TYPE: DNA
<213> ORGANISM: Homo sapiens

<400> SEQUENCE: 131
gactgtttgt gccccatctc                                            20

<210> SEQ ID NO 132
<211> LENGTH: 20
<212> TYPE: DNA
<213> ORGANISM: Homo sapiens

<400> SEQUENCE: 132
ttccccagat ctctgtcctg                                            20

<210> SEQ ID NO 133
<211> LENGTH: 20
<212> TYPE: DNA
<213> ORGANISM: Homo sapiens

<400> SEQUENCE: 133
ctgacattgc tatttgcccc                                            20

<210> SEQ ID NO 134
<211> LENGTH: 20
<212> TYPE: DNA
<213> ORGANISM: Homo sapiens

<400> SEQUENCE: 134
aaagggcctg atatgtgctg                                            20

<210> SEQ ID NO 135
<211> LENGTH: 20
<212> TYPE: DNA
<213> ORGANISM: Homo sapiens

<400> SEQUENCE: 135
agcggtgagt cctagaccct                                            20

<210> SEQ ID NO 136
<211> LENGTH: 20
<212> TYPE: DNA
<213> ORGANISM: Homo sapiens

<400> SEQUENCE: 136
gactcctttc cgtcctcctc                                            20

<210> SEQ ID NO 137
<211> LENGTH: 20
<212> TYPE: DNA
<213> ORGANISM: Homo sapiens

<400> SEQUENCE: 137

-continued

```
cgtcaacact gatcccacct                                    20

<210> SEQ ID NO 138
<211> LENGTH: 20
<212> TYPE: DNA
<213> ORGANISM: Homo sapiens

<400> SEQUENCE: 138
caaaatccag ggatgtggtc                                    20
```